(12) United States Patent
Manku et al.

(10) Patent No.: US 11,478,442 B2
(45) Date of Patent: *Oct. 25, 2022

(54) PHARMACEUTICAL COMPOSITIONS COMPRISING DGLA AND USE OF SAME

(71) Applicant: DS Biopharma Limited, Dublin (IE)

(72) Inventors: Mehar Manku, Birmingham (GB); John Climax, Dublin (IE); David Coughlan, Dublin (IE); James Dunne, Dublin (IE)

(73) Assignee: DS Biopharma Limited

( * ) Notice: Subject to any disclaimer, the term of this patent is extended or adjusted under 35 U.S.C. 154(b) by 0 days.

This patent is subject to a terminal disclaimer.

(21) Appl. No.: 16/910,770

(22) Filed: Jun. 24, 2020

(65) Prior Publication Data

US 2020/0323807 A1    Oct. 15, 2020

Related U.S. Application Data

(63) Continuation of application No. 16/678,431, filed on Nov. 8, 2019, now Pat. No. 10,849,870, which is a continuation of application No. 16/279,819, filed on Feb. 19, 2019, now Pat. No. 10,537,543, which is a continuation of application No. 15/935,739, filed on Mar. 26, 2018, now abandoned, which is a continuation of application No. 15/842,194, filed on Dec. 14, 2017, now abandoned, which is a continuation of application No. 15/661,374, filed on Jul. 27, 2017, now Pat. No. 10,105,333, which is a continuation of application No. 15/343,689, filed on Nov. 4, 2016, now abandoned, which is a continuation of application No. 14/730,818, filed on Jun. 4, 2015, now Pat. No. 9,682,055.

(60) Provisional application No. 62/058,469, filed on Oct. 1, 2014, provisional application No. 62/007,752, filed on Jun. 4, 2014.

(51) Int. Cl.

| | |
|---|---|
| *A61K 31/202* | (2006.01) |
| *A61K 9/48* | (2006.01) |
| *A61K 9/00* | (2006.01) |
| *A61P 17/00* | (2006.01) |
| *A61Q 19/00* | (2006.01) |
| *A61K 8/11* | (2006.01) |
| *A61K 8/65* | (2006.01) |
| *A61K 8/36* | (2006.01) |
| *A61K 31/201* | (2006.01) |
| *A61P 17/04* | (2006.01) |

(52) U.S. Cl.
CPC ........... *A61K 31/202* (2013.01); *A61K 8/11* (2013.01); *A61K 8/361* (2013.01); *A61K 8/65* (2013.01); *A61K 9/0053* (2013.01); *A61K 9/48* (2013.01); *A61K 9/485* (2013.01); *A61K 9/4825* (2013.01); *A61K 9/4866* (2013.01); *A61K 31/201* (2013.01); *A61P 17/00* (2018.01); *A61P 17/04* (2018.01); *A61Q 19/00* (2013.01)

(58) Field of Classification Search
CPC ...... A61K 9/48; A61K 31/202; A61K 9/0053; A61P 17/00

See application file for complete search history.

(56) References Cited

U.S. PATENT DOCUMENTS

| | | |
|---|---|---|
| 4,273,763 A | 6/1981 | Horrobin |
| 4,309,415 A | 1/1982 | Horrobin |
| 4,388,324 A | 6/1983 | Horrobin |
| 4,415,554 A | 11/1983 | Horrobin |
| 4,444,755 A | 4/1984 | Horrobin |
| 4,681,896 A | 7/1987 | Horrobin |
| 4,826,877 A | 5/1989 | Stewart et al. |
| 4,888,326 A | 12/1989 | Horrobin |
| 4,898,885 A | 2/1990 | Horrobin |
| 4,965,075 A | 10/1990 | Horrobin et al. |
| 4,970,076 A | 11/1990 | Horrobin |
| 4,997,657 A | 3/1991 | Horrobin et al. |
| 5,198,468 A | 3/1993 | Horrobin |
| 5,318,991 A | 6/1994 | Horrobin et al. |
| 5,324,748 A | 6/1994 | Horrobin |
| 5,380,757 A | 1/1995 | Horrobin |
| 5,562,913 A | 10/1996 | Horrobin |
| 5,580,556 A | 12/1996 | Horrobin |
| 5,583,159 A | 12/1996 | Horrobin et al. |
| 5,589,509 A | 12/1996 | Horrobin |
| 5,618,558 A | 4/1997 | Horrobin et al. |
| 5,663,202 A | 9/1997 | Horrobin et al. |
| 5,709,885 A | 1/1998 | Hellen et al. |
| 5,789,441 A | 8/1998 | Gosselin et al. |
| 5,888,541 A | 3/1999 | Horrobin et al. |

(Continued)

FOREIGN PATENT DOCUMENTS

| | | |
|---|---|---|
| CA | 1334002 | 1/1995 |
| DE | 4238869 | 5/1994 |

(Continued)

OTHER PUBLICATIONS

Araujo et al., "Evaluation of a Rapid Method for the Quantitative Analysis of Fatty Acids in Various Metrics," J. Chromatogr A., 1212(102):106-113 (publication date: Nov. 28, 2008, epublication date: Oct. 8, 2008).

(Continued)

*Primary Examiner* — Theodore R. Howell

(74) *Attorney, Agent, or Firm* — Perkins Coie LLP

(57) ABSTRACT

The present disclosure provides orally deliverable pharmaceutical compositions comprising DGLA and to methods of using same to treat a variety of conditions and disorders.

12 Claims, 14 Drawing Sheets

(56) References Cited

U.S. PATENT DOCUMENTS

| | | | |
|---|---|---|---|
| 6,140,304 | A | 10/2000 | Sears |
| 6,177,470 | B1 | 1/2001 | Horrobin et al. |
| 6,368,621 | B1 | 4/2002 | Engel et al. |
| 6,479,544 | B1 | 11/2002 | Horrobin |
| 6,602,690 | B2 | 8/2003 | Kawashima et al. |
| 6,630,157 | B1 | 10/2003 | Horrobin et al. |
| 7,888,393 | B2 | 2/2011 | Bettle |
| 8,293,790 | B2 | 10/2012 | Manku et al. |
| 8,455,035 | B2 | 6/2013 | Rein et al. |
| 8,536,223 | B2 | 9/2013 | Kelliher et al. |
| 8,729,126 | B2 | 5/2014 | Kelliher et al. |
| 8,936,803 | B2 | 1/2015 | Manku et al. |
| 8,945,886 | B2 | 2/2015 | Katano et al. |
| 9,006,287 | B2 | 4/2015 | Tateishi et al. |
| 9,050,308 | B2 | 6/2015 | Maines et al. |
| 9,056,086 | B2 | 6/2015 | Manku et al. |
| 9,096,815 | B2 | 8/2015 | Manku et al. |
| 9,682,055 | B2 | 6/2017 | Manku et al. |
| 9,889,106 | B2 | 2/2018 | Kelliher et al. |
| 10,105,333 | B2 | 10/2018 | Manku et al. |
| 10,537,543 | B2 * | 1/2020 | Manku ............. A61P 19/00 |
| 10,849,870 | B2 * | 12/2020 | Manku ............. A61P 13/00 |
| 2004/0043013 | A1 | 3/2004 | McCleary |
| 2005/0032757 | A1 | 2/2005 | Cho |
| 2006/0009522 | A1 | 1/2006 | Dana et al. |
| 2006/0078625 | A1 | 4/2006 | Rockway |
| 2007/0105954 | A1 | 5/2007 | Puri |
| 2007/0248586 | A1 | 10/2007 | Arterburn et al. |
| 2008/0108699 | A1 | 5/2008 | Tateishi et al. |
| 2010/0167359 | A1 | 7/2010 | Katano et al. |
| 2013/0150602 | A1 | 6/2013 | Kelliher et al. |
| 2013/0267598 | A1 | 10/2013 | Manku et al. |
| 2013/0274338 | A1 | 10/2013 | Manku et al. |
| 2015/0079164 | A1 | 3/2015 | Fraser et al. |
| 2016/0362358 | A1 | 12/2016 | Manku et al. |

FOREIGN PATENT DOCUMENTS

| | | |
|---|---|---|
| EP | 0035856 | 9/1981 |
| EP | 0037175 | 10/1981 |
| EP | 0087863 | 9/1983 |
| EP | 0087864 | 9/1983 |
| EP | 0087865 | 9/1983 |
| EP | 0115419 | 8/1984 |
| EP | 0132089 | 1/1985 |
| EP | 0139480 | 5/1985 |
| EP | 0173478 | 3/1986 |
| EP | 0309086 | 3/1989 |
| EP | 0334507 | 9/1989 |
| EP | 0409559 | 1/1991 |
| EP | 0416855 | 3/1991 |
| EP | 1571195 | 9/2005 |
| EP | 1852114 | 11/2007 |
| GB | 2504061 | 1/2014 |
| JP | A-S52-64452 | 5/1977 |
| JP | A-S52-66659 | 6/1977 |
| JP | 4-290820 | 10/1992 |
| JP | H04507397 | 12/1992 |
| JP | H05201924 | 8/1993 |
| JP | H06128154 | 5/1994 |
| JP | H07126160 | 5/1995 |
| JP | H09505562 | 6/1997 |
| JP | 2000191525 | 7/2000 |
| JP | 2002047176 | 2/2002 |
| JP | 2003155233 | 5/2003 |
| JP | A2003525880 | 9/2003 |
| JP | 2004528360 | 9/2004 |
| JP | 2005179211 | 7/2005 |
| JP | 2006219454 | 8/2006 |
| JP | 2006306812 | 11/2006 |
| JP | 2008167721 | 7/2008 |
| JP | 2008-543865 | 12/2008 |
| JP | 2013517304 | 5/2013 |
| RU | 94002337 | 8/1996 |
| RU | 2205004 | 5/2003 |
| WO | WO 1990/014824 | 12/1990 |
| WO | WO 97/29751 | 8/1997 |
| WO | WO 1998/016215 | 4/1998 |
| WO | WO 1998/052556 | 11/1998 |
| WO | WO 01/03696 | 1/2001 |
| WO | WO 2002/096408 | 12/2002 |
| WO | WO 2003/063793 | 8/2003 |
| WO | WO 2008/114141 | 9/2008 |
| WO | WO 2010/125340 | 11/2010 |
| WO | WO 2012/087745 | 6/2012 |
| WO | WO 2013/057284 | 4/2013 |
| WO | WO 2013/057287 | 4/2013 |
| WO | WO 2013/082265 | 6/2013 |
| WO | WO 2013/103902 | 7/2013 |
| WO | WO 2013/112876 | 8/2013 |
| WO | WO 2013/124479 | 8/2013 |
| WO | WO 2014/022816 | 2/2014 |
| WO | WO 2014/040921 | 3/2014 |
| WO | WO 2015/185698 | 12/2015 |
| WO | WO 2017/118911 | 7/2017 |

OTHER PUBLICATIONS

Banno, "Diversified Approach to Acne Care by Using Natural Raw Materials," Fragrance Journal, 35(5):36-41 (publication date: May 2007) (with English translation).

Cayman Chemical, Product Information: Dihomo-γ-Linolenic Acid, Item No. 90230 (publication date: Jul. 7, 2011).

Chen, Yung-Chih et al.; "Therapeutic Effect of Topical Gamma-Linolenic Acid on Refractory Uremic Pruritus"; American Journal of Kidney Diseases, vol. 48, No. 1, pp. 69-76 (publication date: Jul. 2006).

Das, "A defect in the activities of $\Delta^6$ and $\Delta^5$ desaturases and pro-resolution bioactive lipids in the pathobiology of non-alcoholic fatty liver disease," World Journal of Diabetes 2(11):176-188 (publication date: Nov. 15, 2011).

Desbois et al., "Antibacterial free fatty acids: activities, mechanisms of action and biotechnological potential," Appl. Microbiol. Biotechnol., 85:1629-1642 (publication date: Feb. 2010, epublication date: Dec. 3, 2009).

Dignity Sciences Limited, "Oral DS107G in Moderate to Severe Atopic Dermatitis," ClinicalTrials.gov (Study start date: Jan. 2015).

Ericksen et al., "Open trial of supplements of omega 3 and 6 fatty acids, vitamins and minerals in atopic dermatitis," Journal of Dermatological Treatment 17(2):82-85 (2006.

Feldlaufer et al., "Antimicrobial activity of fatty acids against Bacillus larvae, the causative agent of American Foulbrood disease," Apidologie 24. pp. 95-99 (publication date: Nov. 2, 1993).

Frocchi et al., "The Efficacy and Safety of γ-Linolenic Acid in the Treatment of Infantile Atopic Dermatitis," Journal of International Medical Research 22(1):24-32 (publication date: Jan.-Feb. 1994).

Guil-Guerrero et al., "Gamma-linolenic and stearidonic acids: Purification and upgrading of C18-PUFA oils," European J. Lipid Sci. and Tech., 112(10):1068-1081 (publication date: Oct. 2010, epublication date: Sep. 20, 2010).

Horrobin DF, "Nutritional and Medical Importance of Gamma-Linolenic Acid"; Prog. lipid Res, vol. 31(2):163-194 (publication date: Aug. 1992).

Iversen et al., "Effect of dihomogammalinolenic acid and its 15-lipoxygenase metabolite on eicosanoid metabolism by human mononuclear leukocytes in vitro: selective inhibition of the 5-lipoxygenase pathway," Arch Dermatol Res 284(4):222-226 (publication date: Aug. 1992.

Jancin et al., "Bioactive lipid shows promise in atopic dermatitis," Dermatology News (publication date: Nov. 9, 2016).

Jareonkitmongkol et al., "A Novel Δ5-Desaturase-Defective Mutant of Mortierella alpina 1S-4 and Its Dihomo-γ-Linolenic Acid Productivity," Applied Environmental Microbiology 56(12):4300-4304 (publication date: Dec. 1993).

Johnson et al., "Dietary Supplementation with γ-Linolenic Acid Alters Fatty Acid Content and Eicosanoid Production in Healthy Humans," The Journal of Nutrition 127(8):1435-1444 (publication date: Aug. 1, 1997).

(56) References Cited

OTHER PUBLICATIONS

Kanehara, S. et al., "Undershirts coated with borage oil alleviate the symptoms of atopic dermatitis in children," Eur J Dermatol, 17(5):448-9 (publication date: Sep.-Oct. 2007, epublication date: Aug. 2, 2007).
Kang et al., "A Simplified Method for Analysis of Polyunsaturated Fatty Acids," BMC Biochemistry (publication date: Mar. 24, 2005).
Kawashima et al. "Oral Administration of Dihomo-γ-Linolenic Acid Prevents Development of Atopic Dermatitis in NC/Nga Mice," Lipids 43(1):37-43 (publication date: Jan. 2008, epublication date: Nov. 6, 2007).
Kawashima et al., "Industrial Production of Dihomo-γ-linolenic Acid by a Δ5 Desaturase-defective Mutant of Mortierella alpina 1S-4 Fungus," JAOCS 77(11), 1135-1139 (publication date: Nov. 2000).
Kawashima et al., "Subchronic (13-week) oral toxicity study of dihomo-γ-linolenic acid (DGLA) oil in rats," Food and Chemical Toxicology, 47(6):1280-1286 (publication date: Jun. 2009, epublication date: Mar. 9, 2009).
Kendall et al., "Distribution of Bioactive Lipid Mediators in Human Skin," The Journal of Investigative Dermatology 00:1-11 (epublication date: Mar. 12, 2015).
Kernoff et al., "Antithrombotic potential of dihomo-gamma-linolenic acid in man," British Medical Journal 2(6100):1441-1444 (publication date: Dec. 3, 1977).
Lovell et al., "Treatment of Atopic Eczema With Evening Primrose Oil," The Lancet. 278 (publication date: Jan. 31, 1981).
Makrides et al., "Changes in the polyunsaturated fatty acids of breast milk from mothers of full-term infants over 30 wk of lactation," Am J Clin Nutr. 61(6):231-1233 (publication date: Jun. 1, 1995).
Miller et al., "Guinea pig epidermis synthesizes 15-hydroxy-8,11,13-eicosatrienoic acid (15-OH-20:3n6) from dihomogammalinolenic acid (DGLA): a potent lipoxygenase inhibitor derived from dietary primrose oil," Clinical Research 35(3):704A (publication date: Apr. 1987).
Mishra et al., "Fatty acid profile, volatiles and antibacterial screening of lipids of the sponge Fasciospongia cavenosa (schmidt) collected from the Bay of Bengal (Orissa Coast)," J. Serb. Chem. Soc. 74(11):1241-1248 (publication date: Nov. 2009).
Morse et al., "A Meta-Analysis of Randomized, Placebo-Controlled Clinical Trials of Efamol ® Evening Primrose Oil in Atopic Eczema. Where Do We Go From Here in Light of More Recent Discoveries?" Current Pharmaceutical Biotechnology, 7(6):503-524 (publication date: Dec. 2006).
Nagao et al., "Enzymatic purification of dihomo-γ-linolenic acid from Mortierella single-cell oil," Elsevier, Journal of Molecular Catalysis B: Enzymatic 44:14-19 (epublication date: Sep. 15, 2006).
NCT02211417 (ClinicalTrials.gov, Aug. 6, 2014) (Accessed from https://www.clinicaltrials.gov/ct2/history/NCT02211417?V_1 on Aug. 26, 2019) (Year: 2014).
Nu-Chek Prep, Inc. Catalog, The Home of Fine Lipid Organics, 85 pages (publication date: Mar. 18, 2009).

PCT/EP2015/062518 International Search Report dated Aug. 19, 2015.
Ramchurren et al., "Effects of Gamma-linolenic and Dihomo-gamma-linolenic Acids on 7,12-Dimethylbenz(α)anthracene-Induced Mammary Tumors in Rats," Prostaglandins Leukotrienes and Essential Fatty Acids, 53, 95-101 (publication date: Aug. 1995).
Schaefer, "Synthesized Omega-6 DGLA for Anti-inflammatories," Cosmetics & Toiletries (publication date: Feb. 11, 2009).
Schuchardt et al., "Bioavailability of long-chain omega-3 fatty acids," Prostaglandins, Leukotrienes and Essential Fatty Acids 89(1):1-8 (publication date: Jul. 2013).
Scollan et al., "Manipulating the fatty acid composition of muscle and adipose tissue in beef cattle," British Journal of Nutrition, 85(1):15-124 (publication date: Jan. 2001).
Simon et al., "Gamma-Linolenic Acid Levels Correlate with Clinical Efficacy of Evening Primrose Oil in Patients with Atopic Dermatitis," Advances in Therapy 31(2):180-188 (publication date: Feb. 2014, epublictaion date: Jan. 17, 2014).
Stone et al., "The Metabolism of Dihomo-γ-Linolenic Acid in Man," Lipids. 14(2):174-180 (publication date: Feb. 1979).
Tanaka et al., "Oral Administration of Dihomo-Gamma-Linolenic Acid Prevents Itch in Atopic NC/NgaTnd Mice Through PGD1 Production," Acta Demato Venereologica 89(6):694-695 (publication date: Jan. 2009) Abstract only.
Tanaka et al., "Oral Supplementation with Dihomo-γ-Linolenic Acid (DGLA)-Enriched Oil Increases Serum DGLA Content in Healthy Adults," Lipids. 47(6):643-46 (publication date: Jun. 2012, epublication date: Mar. 14, 2012).
Teraoka et al., "Oral Supplementation with Dihomo-γ-linolenic Acid-Enriched Oil Altered Serum Fatty Acids in Healthy Men," Biosci. Biotechnol. Biochem, 73 (6), 1453-1455 (epublication date: Jun. 7, 2009).
Umeda-Sawada et al., "Distribution and Metabolism of Dihomo-γ-linolenic Acid (DGLA, 20:3n-6) by Oral Supplementation in Rats," Biosci. Biotechnol. Biochem. 70 (9), 2121-2130 (epublication date: Sep. 7, 2006).
Wright et al., "Oral Evening-Primrose-Seed Oil Improves Atopic Eczema," The Lancet, 1120-1122 (publication date: Nov. 20, 1982).
Xu et al., "Knockdown of delta-5-desaturase promotes the anticancer activity of dihomo-γ-linolenic acid and enhances the efficacy of chemotherapy in colon cancer cells expressing COX-2," Free Radical Biology and Medicine, 96:67-77 (epublication date: Apr. 19, 2016).
Yazawa et al., "Heterologous Production of Dihomo-γ-Linolenic Acid in *Saccharomyces cerevisiae*" Applied and Environmental Microbiology, 73(21):6965-71 (publication date: Nov. 2007, epublication date: Sep. 14, 2007).
Ziboh et al., "Significance of lipoxygenase-derived monohydroxy fatty acids in cutaneous biology," Prostaglandins & other Lipid Mediators 63(1-2):3-13 (publication date: Nov. 2000).
Ziboh et al., "Metabolism of polyunsaturated fatty acids by skin epidermal enzymes: generation of anti-inflammatory and antiproliferative metabolites," The American Journal of Clinical Nutrition, 71(1 Suppl):361S-366S (publication date: Jan. 2000).

* cited by examiner

PHARMACEUTICAL COMPOSITIONS COMPRISING DGLA AND USE OF SAME

PRIORITY CLAIM

This application is a continuation of U.S. patent application Ser. No. 16/678,431, filed on Nov. 8, 2019, which is a continuation of U.S. patent application Ser. No. 16/279,819, filed on Feb. 19, 2019, which is a continuation of U.S. patent application Ser. No. 15/935,739, filed on Mar. 26, 2018, which is a continuation of U.S. patent application Ser. No. 15/842,194, filed on Dec. 14, 2017, which is a continuation of U.S. patent application Ser. No. 15/661,374, filed on Jul. 27, 2017 (now U.S. Pat. No. 10,105,333), which is a continuation of U.S. patent application Ser. No. 15/343,689, filed on Nov. 4, 2016, which is a continuation of U.S. patent application Ser. No. 14/730,818 filed on Jun. 4, 2015 (now U.S. Pat. No. 9,682,055), which claims priority to U.S. Provisional Patent Application Nos. 62/058,469 and 62/007,752, filed on Oct. 1, 2014 and Jun. 4, 2014, respectively, the entireties of each of the foregoing which are incorporated herein by reference.

TECHNICAL FIELD

The present application relates generally to pharmaceutical compositions comprising DGLA and methods of using same.

BACKGROUND

Dihomo gamma linolenic acid (DGLA) is an essential fatty acid found naturally in the body as the elongation product of gamma linolenic acid (GLA). GLA is in turn a desaturation product of linoleic acid. Soft gelatin encapsulation of DGLA is challenging as it is prone to oxidation to aldehydes which can interact with amino groups in the gelatin polymer in the capsule shell. This can cause slowdown in drug release due to crosslinking of the gelatin polymers.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

SUMMARY

Figure 1:
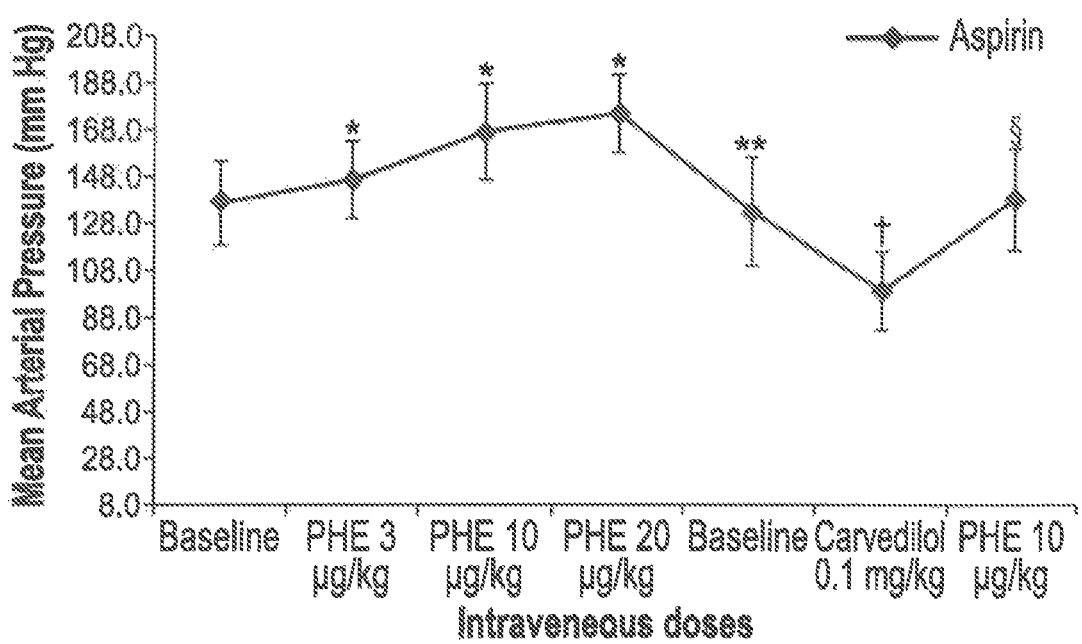
FIG. 1 shows change in mean arterial pressure (mm Hg) with intravenous doses of phenylephrine following seven consecutive days of gavage with Aspirin at 10 mg/kg/day.

The present disclosure provides orally deliverable pharmaceutical compositions comprising DGLA and to methods of using same to treat a variety of conditions and disorders.

In one embodiment, the present disclosure provides a pharmaceutical composition comprising DGLA. In one embodiment, the composition is encapsulated in a capsule shell. In one embodiment, the present disclosure provides a pharmaceutical composition comprising DGLA encapsulated in a capsule shell comprising gelatin, d-sorbitol and 1,4-sorbitan sugar alcohols. In one embodiment, about 500 mg to about 1 g of DGLA or a derivative thereof is encapsulated in the capsule shell.

In one embodiment, the present disclosure provides a method of treating a skin disease or disorder in a subject in need thereof, the method comprising orally administering to the subject a pharmaceutical composition comprising DGLA. Optionally, the pharmaceutical composition comprises DGLA encapsulated in a capsule shell comprising gelatin, d-sorbitol and 1,4-sorbitan sugar alcohols. Optionally, the composition is administered to the subject in an amount sufficient to provide about 1 g to about 4 g of DGLA per day. In one embodiment, the gelatin has a gel mass viscosity of about 9500 to about 11000, for example about 9775 or about 10,500. In another embodiment, the gelatin has a bloom of about 165 to about 190, for example about 170 to about 185. In another embodiment, the gelatin has an ash percentage> than about 0.33.

In one embodiment, the present disclosure provides a method of treating overactive bladder in a subject in need thereof, the method comprising orally administering to the subject a pharmaceutical composition comprising DGLA. Optionally, the pharmaceutical composition comprises DGLA encapsulated in a capsule shell comprising gelatin, d-sorbitol and 1,4-sorbitan sugar alcohols. Optionally, the composition is administered to the subject in an amount sufficient to provide about 1 g to about 4 g of DGLA per day. In one embodiment, the gelatin has a gel mass viscosity of about 9500 to about 11000, for example about 9775 or about 10,500. In another embodiment, the gelatin has a bloom of about 165 to about 190, for example about 170 to about 185. In another embodiment, the gelatin has an ash percentage> than about 0.33. These and other embodiments of the invention are described in further detail below.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

Compositions

In various embodiments, the present disclosure provides orally deliverable pharmaceutical compositions comprising DGLA or a derivative thereof. The term DGLA herein refers to DGLA in free acid form. Compositions of the invention may also comprise a DGLA derivative in addition to or instead of DGLA. Such derivatives include alkyl esters, lower alky esters such as DGLA methyl or ethyl ester or DGLA in triglyceride form. In one embodiment, the present disclosure provides a pharmaceutical composition comprising DGLA or derivative thereof encapsulated in a capsule shell. In one embodiment, about 500 mg to about 1 g of DGLA or derivative thereof is encapsulated in the capsule shell.

In one embodiment, the capsule shell comprises gelatin, for example Gelatin RXL or lime bone gelatin with a lower molecular weight. In another embodiment, the capsule shell comprises Gelatin RXL that has been treated by proteolytic enzyme to cut the gelatin pattern and effectively decrease its molecular weight. In another embodiment, the pharmaceutical composition comprises DGLA esters of D-Sorbitol and 1,4-sorbitan. In one embodiment, the capsule shell comprises (a) gelatin and (b) plasticizers selected from one or more of d-sorbitol and 1,4-sorbitans. In one embodiment, the gelatin is as described in U.S. Pat. No. 7,485,323, hereby incorporated by reference herein in its entirety.

In one embodiment, the plasticizer comprises 1-4 sorbitans in an amount from 20%-30%, for example about 24% and 28% (on a dry basis) and a D-sorbitol content of about 30%-50%, for example about 35% to 45% (on a dry basis).

In some embodiments, the capsule shell further comprises glycerol, purified water, titanium dioxide, medium chain triglycerides and lecithin.

In various embodiments, DGLA or a derivative is present in a composition of the invention in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg. In any such embodiment, the composition can further comprise DGLA esters of D-Sorbitol and 1,4-sorbitan.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of total fatty acids, of fatty acids other than DGLA.

In another embodiment, DGLA or a derivative thereof represents at least about 30%, about 40%, about 50%, at least about 60%, at least about 70%, at least about 80%, at least about 90%, at least about 95%, at least about 97%, at least about 98%, at least about 99%, or 100%, by weight, of all fatty acids present in a composition of the invention.

In one embodiment, a composition of the invention, when placed in a standard disintegration test, for example as set for in USP 2040 (Disintegration and Dissolution of Dietary Supplements) with water as the Medium, has a DGLA release rate less than about 60 minutes, less than about 50 minutes, less than about 40 minutes, less than about 30 minutes, or less than 20 minutes after storage for about 1 month, about 2 months or about 3 months at 40° C./75% RH.

In one embodiment, after storage for about 1 month, about 2 months, about 3 months or about 6 months at 40° C./75% RH, a composition of the invention comprises less than about 5% DGLA esters by weight of all fatty acids, less than about 4% DGLA esters by weight of all fatty acids, less than about 3% DGLA esters by weight of all fatty acids, less than about 2% DGLA esters by weight of all fatty acids, or less than about 1% DGLA esters by weight of all fatty acids.

Methods

Any composition of the invention, including compositions described herein above or compositions that can for formulated from combining various embodiments of the present disclosure, can be used in treatment or prevention of: skin disorders and diseases, including acne vulgaris, acne rosacea, atopic dermatitis, psoriasis, pruritus/itch, radiation protection, dry skin, smooth skin, healthy skin, anti-aging, and photoprotection; urinary disorders and diseases including bladder cancer, cystocele, hematuria, interstitial cystitis, neurogenic bladder, Peyronie's disease, prostate disease, incontinence, urinary tract infection and vasicoureteral reflux; renal disease and disorders including kidney failure, acute kidney injury, chronic kidney disease, and polycystic kidney disease; rheumatic disease including ankylosing spondylitis, fibromyalgia, gout, infectious arthritis, lupus, osteoarthritis, polymyalgia rheumatic, psoriatic arthritis, reactive arthritis, rheumatoid arthritis, sclerodoma; respiratory disorders including inflammatory lung disease, respiratory tract infections, pleural cavity disease, pulmonary vascular disease, pneumonia, pulmonary embolism, and lung cancer; and cardiovascular disorders including acute cardiac ischemic events, acute myocardial infarction, angina, arrhythmia, atrial fibrulation, atherosclerosis, arterial fibrillation, cardiac insufficiency, cardiovascular disease, chronic heart failure, chronic stable angina, congestive heart failure, coronary artery disease, coronary heart disease, deep vein thrombosis, diabetes, diabetes mellitus, diabetic neuropathy, diastolic dysfunction in subjects with diabetes mellitus, edema, essential hypertension, eventual pulmonary embolism, fatty liver disease, heart disease, heart failure, homozygous familial hypercholesterolemia (HoFH), homozygous familial sitosterolemia, hypercholesterolemia, hyperlipidemia, hypertension, hypertriglyceridemia, metabolic syndrome, mixed dyslipidemia, moderate to mild heart failure, myocardial infarction, obesity management, paroxysmal atrial/arterial fibrillation/fibrulation/flutter, paroxysmal supraventricular tachycardias (PSVT), particularly severe or rapid onset edema, platelet aggregation, primary hypercholesterolemia, primary hyperlipidemia, pulmonary arterial hypertension, pulmonary hypertension, recurrent hemodynamically unstable ventricular tachycardia (VT), recurrent ventricular arrhythmias, recurrent ventricular fibrillation (VF), ruptured aneurysm, sitsterolemia, stroke, supraventricular tachycardia, symptomatic atrial fibrillation/ flutter, tachycardia, type-II diabetes, vascular disease, venous thromboembolism, ventricular arrhythmias, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In various embodiments, compositions of the invention are administered in an amount sufficient to provide a daily DGLA dose of about 50 mg to about 10000 mg, about 100 mg to about 7500 mg, or about 100 mg to about 5000 mg, for example about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg about 2600 mg, about 2700 mg, about 2800 mg, about 2900 mg, about 3000 mg, about 3100 mg, about 3200 mg, about 3300 mg, about 3400 mg, about 3500 mg, 3600 mg, about 3700 mg, about 3800 mg, about 3900 mg, about 4000 mg, about 4100 mg, about 4200 mg, about 4300 mg, about 4400 mg, about 4500 mg, 4600 mg, about 4700 mg, about 4800 mg, about 4900 mg, about 5000 mg, about 5100 mg, about 5200 mg, about 5300 mg, about 5400 mg, about 5500 mg of DGLA per day.

In one embodiment, the invention provides a method of treating atopic dermatitis, for example mild to moderate atopic dermatitis. In one embodiment, the method comprises administering to a subject in need of such treatment DGLA in an amount of about 500 mg to about 3 g per day, about 1 g to about 2.5 g per day, about 1 g per day or about 2 g per day. In one embodiment, the DGLA is administered to the subject daily for a period of at least about 2 weeks, at least about 4 weeks or at least about 8 weeks. In a related embodiment, upon treatment in accordance with the present invention, for example over a period of about 1 to about 12 weeks, about 1 to about 8 weeks, or about 1 to about 4 weeks, the subject or subject group exhibits one or more of the following outcomes:

(a) a reduction in eczema area and severity index (EASI) score relative to baseline or placebo control;

(b) a reduction in percentage of area of an anatomical site affected by atopic dermatitis relative to baseline or control;

(c) a reduction in investigator's global assessment score relative to baseline or placebo control;

(d) a reduction in intensity of erythema, edema/population, oozing/crusts, excoriation, lichenification and/or dryness relative to baseline or placebo control;

(e) a reduction in erythema, edema/population, oozing/crusts, excoriation, lichenification and/or dryness relative to baseline or placebo control;

(f) a reduction in body surface area (BSA) affected by atopic dermatitis relative to baseline or placebo control;

(g) a reduction in loss of sleep relative to baseline or placebo control;

(h) a reduction in occurrence of pruitis (itch) relative to baseline or placebo control;

(i) a reduction in severity of pruritis as an average of the prior three days and/or nights on a visual analog scale;

(j) a reduction in SCORAD score relative to baseline or placebo control;

(k) an improved patient-oriented Eczema Measure (POEM) compared to baseline or placebo control;

(l) a reduction in number of days in the preceding week in which the subject reported that the skin was itchy due to eczema;

(m) a reduction in number of days in the preceding week in which the subject reported that their sleep was disturbed due to their eczema;

(n) a reduction in number of days in the preceding week in which the subject experienced skin bleeding;

(o) a reduction in number of days in the preceding week in which the subject experienced skin weeping or oozing clear fluid;

(p) a reduction in number of days in the preceding week in which the subject's skin cracked;

(q) a reduction in number of days in the preceding week in which the subject's skin flaked;

(r) a reduction in number of days in the preceding week in which the subject experienced dry skin;

(s) an increase in trans epidermal water loss compared to baseline or placebo control;

(t) an increase in plasma total and free DGLA compared to baseline;

(u) an increase in DGLA:AA ratio compared to baseline or placebo control; and/or (v) a reduction in arterial blood pressure compared to baseline or placebo control.

In one embodiment, methods of the present invention comprise measuring baseline levels of one or more markers or parameters set forth in (a)-(v) above prior to dosing the subject or subject group. In another embodiment, the methods comprise administering a composition as disclosed herein to the subject after baseline levels of one or more markers or parameters set forth in (a)-(v) are determined, and subsequently taking an additional measurement of said one or more markers.

In another embodiment, upon treatment with a composition of the present invention, for example over a period of about 1 to about 12 weeks, about 1 to about 8 weeks, or about 1 to about 4 weeks, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of or all 22 of outcomes (a)-(v) described immediately above.

In another embodiment, upon treatment with a composition of the present invention, the subject or subject group exhibits one or more of the following outcomes:

(a) a reduction in eczema area and severity index (EASI) score relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(b) a reduction in percentage of area of an anatomical site affected by atopic dermatitis relative to baseline or control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(c) a reduction in investigator's global assessment score relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(d) a reduction in intensity of erythema, edema/population, oozing/crusts, excoriation, lichenification and/or dryness relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(e) a reduction in erythema, edema/population, oozing/crusts, excoriation, lichenification and/or dryness relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(f) a reduction in body surface area (BSA) affected by atopic dermatitis relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(g) a reduction in loss of sleep relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(h) a reduction in occurrence of pruitis (itch) relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(i) a reduction in severity of pruritis as an average of the prior three days and/or nights on a visual analog scale of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(j) a reduction in SCORAD score relative to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(k) an improved patient-oriented Eczema Measure (POEM) compared to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(l) a reduction in number of days in the preceding week in which the subject reported that their skin was itchy due to eczema of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(m) a reduction in number of days in the preceding week in which the subject reported that their sleep was disturbed due to their eczema of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(n) a reduction in number of days in the preceding week in which the subject experienced skin bleeding of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(o) a reduction in number of days in the preceding week in which the subject experienced skin weeping or oozing clear fluid of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(p) a reduction in number of days in the preceding week in which the subject's skin cracked of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(q) a reduction in number of days in the preceding week in which the subject's skin flaked of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(r) a reduction in number of days in the preceding week in which the subject experienced dry skin of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(s) an increase in trans epidermal water loss compared to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%;

(t) an increase in plasma total and free DGLA compared to baseline of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%; and/or (u) an increase in DGLA:AA ratio compared to baseline or placebo control of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%; and/or (v) a reduction in mean arterial blood pressure of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%.

In another embodiment, upon treatment with a composition of the present invention after a single dose administration or multiple dose administration, for example over a period of about 1 to about 12 weeks, about 1 to about 8 weeks, or about 1 to about 4 weeks, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of or all 22 of outcomes (a)-(v) described immediately above.

In another embodiment, upon treatment of a subject or subject group (fed or fasted) with a composition comprising about 200 mg of DGLA to about 8000 mg DGLA (administered as one or more dosage units, for example as 500 mg or 1 g dosage units equating to total daily DGLA doses of about 500 mg, about 1000 mg, about 2000 mg, about 3000 mg, about 4000 mg, about 5000 mg, about 6000 mg, about 7000 mg or about 8000 mg) and after single dose administration or after multiple dose administration, the subject or subject group exhibits one or more of the following outcomes:

(a) a free DGLA $C_{max}$ (or mean or median $C_{max}$) of about 400 ng/ml to about 4500 ng/ml, about 500 ng/ml to about 3400 ng/ml, about 600 ng/ml to about 3300 ng/ml, about 700 ng/ml to about 3200 ng/ml, for example about 900 ng/ml, about 1000 ng/ml, about 1100 ng/ml, about 1200 ng/ml, about 1300 ng/ml, about 1400 ng/ml, about 1500 ng/ml, about 1600 ng/ml, about 1700 ng/ml, about 1800 ng/ml, about 1900 ng/ml, about 2000 ng/ml, about 2100 ng/ml, about 2200 ng/ml, about 2300 ng/ml, about 2400 ng/ml, about 2500 ng/ml, about 2600 ng/ml, about 2700 ng/ml, about 2800 ng/ml, about 2900 ng/ml, about 3000 ng/ml, about 3100 ng/ml, about 3200 ng/ml, about 3300 ng/ml, about 3400 ng/ml, about 3500 ng/ml, about 3600 ng/ml, about 3700 ng/ml, about 3800 ng/ml, about 3900 ng/ml, about 4000 ng/ml, about 4100 ng/ml, about 4200 ng/ml, about 4300 ng/ml about 4400 ng/ml or about 4500 ng/ml;

(b) a free DGLA $C_{max}$/dose (or mean or median $C_{max}$/dose) of about 0.5 (1/kL) to about 3 (1/kL), about 0.6 (1/kL) to about 2.5 (1/kL) or about 0.7 (1/kL) to about 2 (1/kL), for example about 0.7 (1/kL), about 0.8 (1/kL), about 0.9 (1/kL), about 1 (1/kL), about 1.5 (1/kL), about 1.6 (1/kL), about 1.7 (1/kL) or about 1.8 (1/kL);

(c) a free DGLA $AUC_{0-24}$ (or mean or median $AUC_{0-24}$) of about 1500 ng·h/ml to about 12000 ng·h/ml, about 2000 ng·h/ml to about 11000 ng·h/ml or about 2500 ng·h/ml to about 10000 ng·h/ml, for example about 1000 ng·h/ml, about 1500 ng·h/ml, about 2000 ng·h/ml, about 2500 ng·h/ml, about 3000 ng·h/ml, about 3500 ng·h/ml, about 4000 ng·h/ml, about 4500 ng·h/ml, about 5000 ng·h/ml, about 5500 ng·h/ml, about 6000 ng·h/ml, about 6500 ng·h/ml, about 7000 ng·h/ml, about 7500 ng·h/ml, about 8000 ng·h/ml, about 8500 ng·h/ml, about 9000 ng·h/ml, about 9500 ng·h/ml, about 10000 ng·h/ml, about 10500 ng·h/ml, about 11000 ng·h/ml, about 11500 ng·h/ml or about 12000 ng·h/ml.

(d) a free DGLA $AUC_{0-24}$/dose (or mean or median $AUC_{0-24}$/dose) of about 1.5 to about 10 h/kL, about 1.7 to about 8 h/kL or about 2 to about 6 h/kL, for example about 2 h/kL, about 2.5 h/kL, about 3 h/kL, about 3.5 h/kL, about 4 h/kL, about 4.5 h/kL, about 5 h/kL or about 5.5 h/kL;

(e) a free DGLA $t_{max}$ (h) of about 2 to about 10 hours, about 3 to about 8 hours, for example about 3 hours, about 4 hours, about 5 hours, about 6 hours, about 7 hours or about 8 hours;

(f) a total DGLA $C_{max}$ (or mean or median total DGLA $C_{max}$) of about 4000 ng/ml to about 45000 ng/ml, about 5000 ng/ml to about 34000 ng/ml, about 6000 ng/ml to about 33000 ng/ml, or about 7000 ng/ml to about 32000 ng/ml, for example about 7000 ng/ml, about 7200 ng/ml, about 7500 ng/ml, about 8000 ng/ml, about 8500 ng/ml, about 9000 ng/ml, about 9500 ng/ml, about 10000 ng/ml, about 11000 ng/ml, about 12000 ng/ml, about 13000 ng/ml, about 14000 ng/ml, about 15000 ng/ml, about 16000 ng/ml, about 17000 ng/ml, about 18000 ng/ml, about 19000 ng/ml, about 20000 ng/ml, about 21000 ng/ml, about 22000 ng/ml, about 23000 ng/ml, about 24000 ng/ml, about 25000 ng/ml, about 26000 ng/ml, about 27000 ng/ml, about 28000 ng/ml, about 29000 ng/ml, about 30000 ng/ml, about 31000 ng/ml, about 32000 ng/ml, about 33000 ng/ml, about 34000 ng/ml, or about 35000 ng/ml;

(g) a total DGLA $C_{max}$/dose (or mean or median total DGLA $C_{max}$/dose) of about 2 (1/kL) to about 25 (1/kl), about 4 (1/kl) to about 20 (1/kl) or about 5 (1/kl) to about 17 (1/kl), for example about 6 (1/kl), about 9 (1/kl), about 14 (1/kl) or about 16 (1/kl);

(h) a total DGLA $AUC_{0-24}$ (or mean or median total DGLA $AUC_{0-24}$) of about 15000 ng·h/ml to about 900,000 ng·h/ml, about 20,000 ng·h/ml to about 250,000 ng·h/ml or about 25,000 ng·h/ml to about 225,000 ng·h/ml, for example about 40,000 ng·h/ml, about 210,000 ng·h/ml, about 215,000 ng·h/ml or about 435,000 ng·h/ml;

(i) a total DGLA $AUC_{0-24}$/dose (or mean or median total DGLA $AUC_{0-24}$/dose) of about 50 to about 400 h/kL, about 60 to about 250 h/kL or about 70 to about 225 h/kL, for example about 80 h/kL, about 100 h/kL, about 110 h/kL or about 215 h/kL;

(j) a total DGLA $t_{max}$ (h) of about 2 to about 25 hours or about 3 to about 20 hours, for example about 8 hours, about 10 hours, or about 18 hours;

(k) a ratio of total DGLA $C_{max}$ to free DGLA $C_{max}$ of about 5:1 to about 12:1, about 6:1 to about 10:1 or about 7:1 to about 9:1, for example about 7.7:1, about 8.6:1, about 8.8:1 or about 9.8:1;

(l) a steady state free DGLA plasma level ($C_{avg}$) or mean or median steady state free DGLA plasma level ($\bar{C}_{avg}$), after 1 to about 30, 1 to about 28, 1 to about 14 or 1 to about 10 consecutive days of daily administration, of up to about 2000 ng/ml, up to about 750 ng/ml, or up to about 700 ng/ml, for example about 385 ng/ml or about 675 ng/ml;

(m) a steady state total DGLA plasma level ($C_{avg}$) or mean or median steady state total DGLA plasma level ($\bar{C}_{avg}$), after 1 to about 30, 1 to about 28, 1 to about 14 or 1 to about 10 consecutive days of daily administration, of up to 250,000 ng/ml, up to 180,000 ng/ml, up to 150,000 ng/ml, up to 125,000 ng/ml or up to 100,000 ng/ml; and/or (n) a ratio of free DGLA plasma to DGLA skin (e.g. as measured in skin blister fluid) from about 0.2:1 to about 5:1, about 0.5:1 to about 2.5:1 or about 0.6:1 to about 1.5:1. In another embodiment, upon treatment with a composition of the present invention, for example over a period of about 1 to about 12 weeks, about 1 to about 8 weeks, or about 1 to about 4 weeks, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of or all 22 of outcomes (a)-(n) described immediately above.

In another embodiment, upon treatment of fasted and fed subjects or fasted and fed subject groups with a composition comprising about 200 mg of DGLA to about 8000 mg DGLA (administered as one or more dosage units, for example as 500 mg or 1 g dosage units equating to total daily DGLA doses of about 500 mg, about 1000 mg, about 2000 mg, about 3000 mg, about 4000 mg, about 5000 mg, about 6000 mg, about 7000 mg or about 8000 mg) and after single dose administration or after multiple dose administration, the subject or subject group exhibits one or more of the following outcomes:

(a) a ratio of free DGLA $C_{max}$ fasted:fed between about 1:1 to about 5:1, for example of about 2.5:1, of about 3:1 or of about 3.5:1;

(b) a ratio of free DGLA $AUC_{0-24}$ fasted:fed between about 1:1 and about 5:1, for example of about 1.5:1, of about 2:1, or of about 2.5:1;

(c) a ratio of total DGLA $C_{max}$ fasted:fed between about 1:1 to about 5:1, for example of about 1:1, of about 1.5:1 or of about 2:1; and/or (d) a ratio of total DGLA $AUC_{0-24}$ fasted:fed between about 1:1 and about 5:1, for example of about 1.5:1, of about 2:1 or of about 2.5:1.

In one embodiment, a DGLA-containing composition of the invention comprises the following fatty acid fingerprint:

| | |
|---|---|
| C18:1n-9 | <LOD-<5% |
| C18:2n-6 | <LOD-<5% |
| 20:3ω6 - DGLA | NLT 95 |
| isomerA | <LOD-<5% |
| C20:4n-6 + isomerB | <LOD-<5% |
| Total unidentified related substances | NMT 2 |

In one embodiment, a DGLA-containing composition of the invention comprises the following fatty acid fingerprint:

| Fatty Acid Profile (Area % FAMEs by GC) | |
|---|---|
| 20:3ω6 - DGLA | NLT 95 |
| Related Substances | |
| 20:2ω6 | <LOD-<5% |
| 20:3ω3 | <LOD-<5% |
| 20:4ω6 | <LOD-<5% |
| 20:4ω3 | <LOD-<5% |
| 20:5ω3 | <LOD-<5% |
| Total unidentified related substances | NMT 2 |

An illustrative DGLA-containing composition of the invention comprises the following fatty acid fingerprint:

| | |
|---|---|
| C16:0 | <LOD-<5% |
| C18:1n-7 | <LOD-<5% |
| C18:1n-9 | <LOD-<5% |
| C18:2n-6 | <LOD-<5% |
| C18:3n-6 | <LOD-<5% |
| C20:3n-3 | <LOD-<5% |
| 20:3n-6 - DGLA | NLT 95 |
| C20:4n-6 | <LOD-<5% |
| Total unidentified related substances | NMT 2 |

In one embodiment, a DGLA-containing composition of the invention comprises the following fatty acid fingerprint:

| Fatty Acid Profile (Area % FAMEs by GC) | |
|---|---|
| 20:3ω6 - DGLA | NLT 95 |
| Related Substances | |
| 16:0 | <LOD-<5% |
| 18:3n-6 alcohol methyl ether | <LOD-<5% |
| 18:3n-6 alcohol formate | <LOD-<5% |
| 16:3n-3 | <LOD-<5% |
| 18:1n-9 | <LOD-<5% |
| 18:1n-7 | <LOD-<5% |
| 19:3 | <LOD-<5% |
| 20:1n-9 | <LOD-<5% |
| 20:2n-6 | <LOD-<5% |
| 20:2n-3 + DGLA isomer | <LOD-<5% |
| 20:3n-3 | <LOD-<5% |
| 20:4n-3 | <LOD-<5% |
| Methyl 7,11,14-eicosatrienoate (DGLA isomer) | <LOD-<5% |
| 22:5n-3 | <LOD-<5% |
| Total unidentified related substances | NMT 2 |

In one embodiment, a DGLA-containing composition of the invention comprises the following fatty acid fingerprint:

| | | |
|---|---|---|
| C20:3 n-6 (DGLA - triglycerides) | Min. | 30% |
| C16:0 | Max. | 26% |
| C18:0 | Max. | 12% |
| C18:1 n-9 | Max. | 15% |
| C18:2 n-6 | Max. | 15% |
| C18:3 n-6 | Max. | 5% |
| C20; 4 n-6 | Max. | 1% |
| C22:0 | Max. | 5% |
| C24:0 | Max. | 15% |

EXAMPLES

Example 1

Three batches of pharmaceutical compositions comprising DGLA (with 2000 pm dl-alpha tocopherol) filled into gelatin capsules were prepared as shown in Table 1.

TABLE 1

| Batch Number | DGLA (mg/Capsule) | Gelatin Description |
|---|---|---|
| E09726/1 | 250 | Standard acid bovine gelatin |
| E09726/2 | 250 | Lime bone gelatin with a lower molecular weight (Mw) |
| E09727 | 500 | Standard acid bovine gelatin |

The capsules shells included the following excipients: gelatin, purified water, glycerol, titanium dioxide, and the processing aids lecithin and medium chain triglyceride.

Additional batches of DGLA capsules were also prepared including DGLA FFA (stabilized with a nominal 2000 ppm dl-alpha tocopherol) in capsules containing gelatin, polysorb or mixture of gylcerol/polysorb, purified water, titanium dioxide, and the processing aids lecithin and medium-chain triglyceride as shown in Table 2.

TABLE 2

| Batch Number | DGLA (mg/Capsule) | Gelatin Description | Plasticizer |
|---|---|---|---|
| E09778 | 500 | Lime bone gelatin with a lower molecular weight (Mw) | Glycerol |
| E09777/01 | 500 | Lime bone gelatin with a lower molecular weight (Mw) | Polysorb (D-sorbitol and 1,4-sorbitan sugar alcohols in water solution) |
| E09777/02 | 500 | Lime bone gelatin with a lower molecular weight (Mw) | Gycerol + Polysorb |
| E09777/03 | 500 | Lime bone gelatin with a lower molecular weight (Mw) - Even Lower Mw (Advanced RXL Gelatine) | Polysorb |

Capsule shell compositions for each of the batches are shown below in Tables 3 and 4.

TABLE 3

| | Unit Quantity mg/capsule | | | |
|---|---|---|---|---|
| Active Substance DGLA | 500 mg | | | |
| Wet Gelatin Shell Mass | E09778 | E09777/01 | E09777/02 | E09777/03 |
| Gelatin | 128.97 (RXL) | 128.97 (RXL) | 128.97 (RXL) | 128.97 (RXL Adv.)[1] |

TABLE 3-continued

| | Unit Quantity mg/capsule | | | |
|---|---|---|---|---|
| Total Glycerol | 67.70 | 2.94 | 35.32 | 2.94 |
| Polysorb | N/A | 64.76 | 32.38 | 64.76 |
| Purified Water[2] | 100.38 | 100.38 | 100.38 | 100.38 |
| Titanium Dioxide | 2.94 | 2.94 | 2.94 | 2.94 |
| Lecithin | Trace | Trace | Trace | Trace |
| Triglycerides Medium Chain | Trace | Trace | Trace | Trace |

[1]RXL gelatin contains a lower number of high molecular weight polymers (~5% >200,000 Da)

TABLE 4

| | Unit Quantity | | | |
|---|---|---|---|---|
| E09726/01 | mg/capsule | % w/w | mg/capsule | % w/w |
| Active Substance | | | | |
| DGLA | 500 | 100 | 250 | 100 |

TABLE 4-continued

| | Unit Quantity | | | |
|---|---|---|---|---|
| E09726/01 | mg/capsule | % w/w | mg/capsule | % w/w |
| Wet Gelatin Shell Mass[2] | | | | |
| Gelatin (not RXL) | 132.35 | 44.12 | 87.79 | 44.12 |
| Total Glycerol | 76.76 | 25.59 | 50.92 | 25.59 |
| Purified Water | 87.95 | 29.31 | 58.33 | 29.31 |
| Glycerol and Polysorb? | — | — | — | — |
| Titanium Dioxide | 2.94 | 0.98 | 1.95 | 0.98 |
| Lecithin | Trace | Trace | Trace | Trace |
| Triglycerides Medium Chain | Trace | Trace | Trace | Trace |

Stability testing of the above capsules was performed. Capsules from each batch were maintained for up to 6 months and assessed using a qualitative or quantitative USP 2040 Disintegration and Dissolution test protocol. Results are shown in Tables 5-7.

TABLE 5

Stability Data for DGLA Softgel capsules: Qualitative Rupture Test Results

| Specification: | Results (Months): | | | | | | | | | | | | |
|---|---|---|---|---|---|---|---|---|---|---|---|---|---|
| | 1 | 2 | 3 | | | | | | 6 | | | | |
| read and record (min) | 40° C./ 75% RH | 40° C./ 75% RH | 25° C./ 60% RH | | 30° C./ 65% RH | | 40° C./ 75% RH | | 25° C./ 60% RH | | 30° C./ 65% RH | | 40° C./ 75% RH |
| Batches | 0 N/A | | | Without pepsin | With pepsin | Without pepsin | With pepsin | Without pepsin | With pepsin | Without pepsin | With pepsin | Without pepsin | With pepsin | Without pepsin | With pepsin |
| E09726/01 | 7 | 6 | >30/ 22 [(1)] | 8 | N/A | 1 caps on 6 > 30 | NP | >30 | 14 | >30 | | >30 | | >30 | 2 caps on 6 > 30 |
| E09726/02 | 4 | 4 | 4 | 3 | N/A | | | 1 caps on 6 > 30 | 6 | 1 caps on 6 > 30 | 10 | 2 caps on 6 > 30 | 9 | 12 | 15 |
| E09727 | | >30 | | 4 caps on 6 > 30 | 10 | >30 | NP | >30 | 15 | >30 | 14 | >30 | 16 | >30 | 3 caps on 6 > 30 |

TABLE 6

DGLA glyceride percentages

| Batch | Time Time point (months) | 25 | 30 | 40 |
|---|---|---|---|---|
| | | | DGLA glycerides % | |
| E09727 | 0 | 0 | 0 | 0 |
| | 1 | 0 | 0 | 0.54 |
| | 2 | 0 | 0 | 1.19 |
| | 3 | 0.41 | 0.67 | 2.1 |
| | 6 | 0.53 | 1.43 | 5.81 |
| E09726/1 | 0 | 0 | 0 | 0 |
| | 1 | 0 | 0 | 0.56 |
| | 2 | 0 | 0 | 1.35 |
| | 3 | 0.37 | 0.58 | 2.31 |
| | 6 | 0.68 | 1.42 | 6.8 |
| E09726/2 | 0 | 0 | ND | 0 |
| | 1 | 0 | ND | ND |
| | 2 | 0 | ND | 1.63 |
| | 3 | 0.51 | ND | ND |
| | 6 | 1.16 | ND | 8.55 |

TABLE 7

| Specifications | | Storage Conditions 40° C./75% RH | Acid Value 176-184 | Mono, Di and Triglycerides Assay (% DGLA) Read and record | DGLA Esters (%) Read and record | Quantitative Rupture test Read and record (mean %) | |
|---|---|---|---|---|---|---|---|
| | | | | | | | Tier II stage 2 |
| E09778 | (RXL + Glycerol) | 3 months | 172 | 3.08 | N/A | 15 min<br>30 min<br>45 min<br>60 min | N/A<br>92<br>96<br>97 |
| | | | | | | | Tier I |
| | | 1 month | 178 | 0.98 | 1.8 to 2.6[2] | 15 min<br>30 min<br>45 min<br>60 min | 94<br>102<br>102<br>102 |
| E09777/01 | (RXL + Polysorb) | 1 month | 180 | N/A | 1.8 to 2.9[2] | 15 min<br>30 min<br>45 min<br>60 min | 81<br>91<br>96<br>102 |
| | | | | | | | Tier II |
| | | 3 months | 182 | N/A | Not available | 15 min<br>30 min<br>45 min<br>60 min | N/A<br>97<br>99<br>98 |
| | | | | | | | Tier I |
| E09777/02 | (RXL + Glycerol + Polysorb) | 1 month | 177 | <0.5 | 0.0 to 3.4[2] | 15 min<br>30 min<br>45 min<br>60 min | 95<br>101<br>101<br>102 |
| | | | | | | | Tier I |
| | | 3 months | 177 | 3.1 | Not avalable | 15 min<br>30 min<br>45 min<br>60 min | 92<br>97<br>97<br>98 |
| | | | | | | | Tier I |
| E09777/03 | (RXL adv. + Polysorb) | 1 month | 171[(2)] | N/A | 2.7 to 3.6[2] | 15 min<br>30 min<br>45 min<br>60 min | 88<br>97<br>99<br>99 |
| | | | | | | | Tier I |
| | | 3 months | 174 | N/A | Not Available | 15 min<br>30 min<br>45 min<br>60 min | 87<br>94<br>95<br>95 |

As seen above, there was a slowdown in dissolution rate in water over time for capsules formulated with glycerol and standard acid bovine gelatin (E09726/01, and E09727). There was a DGLA release rate of greater than 30 mins after 6 months at 40° C./75% RH in simulated gastric fluid (pH 1.2, pepsin).

A DGLA release rate of less than 30 mins after 6 months 40° C./75% RH was only achieved in simulated gastric fluid (pH 1.2, pepsin) with capsules containing lime bone gelatin with a lower molecular weight (Mw) (E09777/02).

There was a significant increase in DGLA glyceride formation over time in DGLA capsule shells containing glycerol (Table 4). This was temperature dependent with highest concentrations of DGLA formed at 40° C. 75% RH.

Polysorb is commonly used as a hydrophilic plasticizer to limit exchange between capsule fill media and shell. D-Sorbitol and 1,4-sorbitan have a higher MW than glycerol which limits its mobility through the gelatin shell. Despite this, there was still interaction of D-Sorbitol and 1,4-sorbitan to form DGLA FFA esters in batches E09777 1/2 and 3.

There was no reduction in acid value of the DGLA for batches formulated with D-Sorbitol and 1,4-sorbitan (E09777 1/02/3) whereas there was a reduction in acid value for E09778 formulated with glycerol.

There was no slowdown in dissolution rate in water over time for capsules formulated with D-Sorbitol and 1,4-sorbitan (E09777/03). The DGLA release rate was less than 30 minutes in water after 3 months 40° C./75% RH.

Example 2

A randomised, double-blind, placebo-controlled, phase II study to assess the efficacy and safety of orally administered DGLA to patients with moderate to severe atopic dermatitis will be conducted. Approximately 100 male or female subjects, aged 18 years or older, with moderate to severe atopic dermatitis (AD) will be included in this study.

Atopic dermatitis is a chronic inflammatory skin disorder characterized by the presence of pruritus, papules, lichenification, excoriations, xerosis and oozing. The prevalence of AD has increased in the last few decades, affecting up to 20 percent of young children with the majority of cases starting in children younger than 5 years of age. Most cases improve by adulthood.

AD is a multifactorial disease, with genetics, environment, and impaired immune response being the predominant factors. Dendritic cells, T lymphocytes, macrophages, keratinocytes, mast cells, and eosinophils all play a role in AD by releasing proinflammatory cytokines and chemokines which induce the inflammatory response characteristic of atopic dermatitis lesions.

Most of currently approved treatments for AD are topical and include corticosteroids, pimecrolimus and tacrolimus. Corticosteroids have been the mainstay of treatment for AD and different potencies and formulations are available. Topical corticosteroids are effective for the treatment of AD but their use is limited by the potential for local side effects such as skin atrophy and striae. Systemic absorption of corticosteroids can also induce diabetes, cataracts, osteoporosis and suppression of the hypothalamic pituitary axis. In addition, transient improvement is often followed by a rebound flare-up on discontinuation of treatment. Other treatments available include topical calcineurin inhibitors (e.g., pimecrolimus, tacrolimus), and coal tar preparations. Cases of lymphoma have been reported in patients treated with calcineurin inhibitors. Patients with more severe disease are treated with ultraviolet B and A phototherapy or oral agents such as corticosteroids, cyclosporine, mycophenolate mofetil, methotrexate and azathioprine.

Dihomo-gamma-linolenic acid (DGLA) is an essential fatty acid found naturally in the body as the 2 carbon elongation product of gamma-linolenic acid (GLA). DGLA is metabolized by cyclooxygenase (COX) and lipoxygenase (LPO) enzymes to form eicosanoids, prostaglandins (PG) of the 1 series and also hydroxyl-fatty acid as 15 hydroxyeicosatrienoic acid DGLA (15 HETrE).

Study Hypothesis and Objectives

DS107G is superior to placebo for improvement of EASI score in patients with moderate to severe atopic dermatitis.

Primary objective: To compare the efficacy of two doses of orally administered DS107G capsules versus placebo, in the treatment of adult patients with moderate to severe atopic dermatitis.

Secondary objective: To assess the safety of two doses of orally administered DS107G capsules versus placebo, in adult patients with moderate to severe atopic dermatitis.

Study Endpoints

Primary Endpoint
Proportion of patients achieving an IGA (Investigator Global Assessment) of 0 (clear) or 1 (almost clear) and a decrease of at least 2 points in IGA at Week 8.
Secondary Endpoints
Change from baseline in IGA at week 2, 4 and 8;
Change from baseline in EASI (Eczema Area and Severity Index) at week 2, 4 and 8;
Proportion of patients achieving at least a 1-point decrease in IGA at week 8;
Change from baseline in the Patient Orientated Eczema Measure (POEM) at week 2, 4 and 8;
Change from baseline in the Dermatology Life Quality Index (DLQI) score at week 2, 4 and 8;
Change from baseline in SCORAD at week 2, 4 and 8;
Change from baseline in the patient's Visual Analog Scale (VAS) pruritus score at Week 2, 4 and 8;
Change from baseline in Body Surface Area (BSA) at Week 2, 4 and 8;
Number of treatment-emergent adverse events (TEAEs) in each treatment group;
Exploratory Endpoints
Change from baseline in Trans epidermal water loss (TEWL) at week 2, 4 and 8 (selected sites only);
Plasma total and free DGLA concentrations at Baseline, weeks 4 and 8;
Plasma total fatty acid profile at Baseline, week 4 and week 8 (sample to be retained and analyzed at a later date);

Study Design

Approximately 100 patients with moderate to severe atopic dermatitis will be included in this multicenter, double blind, placebo controlled, phase IIa study. All subjects will sign an informed consent and undergo screening for study eligibility. Subjects will be randomized (1:1) at baseline visit to either receive oral 2 g DS107G (DGLA capsules provided as opaque, oval soft gelatin capsules containing 500 mg DGLA), 1 g DS107G or placebo once daily for 8 weeks in a fasting state. Enrollment will be stratified by disease severity (based on IGA) and a maximum of 30% of patients with mild atopic dermatitis (as defined by an IGA score of 2) will be recruited.

Subjects will come to the clinic on 6 occasions: at screening, baseline, week 2, week 4, week 8 (end of treatment/early termination) and week 10 (follow-up). All subjects will exit the study at the Week 10 visit. The primary efficacy variable will be the proportion of patients achieving an IGA of 0 (clear) or 1 (almost clear) and a decrease of at least 2 points in IGA at week 8. Secondary efficacy variables will include IGA at other visits, pruritus (obtained from the SCORAD visual analog scale), EASI, BSA, POEM, DLQI, SCORAD and TEWL (for selected sites only). Safety will be assessed through adverse events, physical examination, vital signs and safety laboratory tests (including pregnancy tests for women of childbearing potential). Pharmacokinetic samples will be obtained at Baseline (Day 0), week 4 and week 8 visits in order to measure total and free DGLA plasma trough levels. Separate plasma samples will be retained for later analysis of total fatty acid profile and interleukin profile.

Study Population

Approximately 100 subjects with moderate to severe atopic dermatitis as per IGA score and a BSA of minimum 10% may be included in this study. Subjects will be men or women, 18 years or older.

Inclusion Criteria:
  Male or female subject aged 18 years and older on the day of signing the informed consent form (ICF).
  Clinically confirmed diagnosis of active atopic dermatitis according to Hanifin and Rajka criteria (Appendix G).
  Moderate to severe atopic dermatitis at baseline as defined by an IGA of minimum 3 at baseline visit.
  Atopic dermatitis covering minimum 10% of the body surface area at baseline.
  Body mass index (BMI) is between 18 and 35 kg/m2 inclusively.
  Female patients of childbearing potential must use adequate contraception or have a sterilized partner for the duration of the study: systemic hormonal contraceptives, intrauterine device or barrier method of contraception in conjunction with spermicide, or agree to sexual abstinence. Hormonal contraceptives must be on a stable dose for at least one month before baseline. Note: Women of non-child bearing potential are:
    women who have had surgical sterilization (hysterectomy or bilateral oophorectomy or tubal ligation);
    women greater than 60 years of age;
    women greater than 40 and less than 60 years of age who have had a cessation of menses for at least 12 months and a follicle-stimulating hormone (FSH)
test confirming non-childbearing potential (FSH≥40 mIU/mL) or cessation of menses for at least 24 months without FSH levels confirmed.
  Patients who are able and willing to stop treatment for atopic dermatitis throughout the study (except for allowed emollients);
  Capable and willing to give signed informed consent and the consent must be obtained prior to any study related procedures.
Exclusion Criteria
  Female patients with positive pregnancy test at screening or Day 0 visit (baseline) or lactating women.
  Any clinically significant controlled or uncontrolled medical condition or laboratory abnormality that would, in the opinion of the investigator, put the patient at undue risk or interfere with interpretation of study results.
  Clinically significant impairment of renal or hepatic function.
  Other skin conditions that might interfere with atopic dermatitis diagnosis and/or evaluation (such as psoriasis or current viral, bacterial and fungal skin infections).
  History of hypersensitivity to any substance in DS107G or placebo capsules.
  Use of biologics 3 months prior to start of treatment/Day 0 visit (baseline), or 5 half-lives (whichever is longer).
  Use of systemic treatments (other than biologics) that could affect atopic dermatitis less than 4 weeks prior to baseline visit (Day 0), e.g. retinoids, calcineurin inhibitors, methotrexate, cyclosporine, hydroxycarbamide (hydroxyurea), azathioprine and oral/injectable corticosteroids; Intranasal corticosteroids and inhaled corticosteroids for stable medical conditions are allowed.
  Treatment with any experimental drug within 30 days prior to Day 0 visit (baseline), or 5 half-lives (whichever is longer).
  Excessive sun exposure, use of tanning booths or other ultraviolet (UV) light sources 4 weeks prior to Day 0 visit (baseline) and/or is planning a trip to sunny climate or to use tanning booths or other UV sources between screening and follow-up visits.
  Use of any topical medicated treatment for atopic dermatitis 2 weeks prior to start of treatment/Day 0 visit (baseline), including but not limited to, topical corticosteroids, calcineurin inhibitors, tars, bleach, antimicrobials and bleach baths.
  Use of topical products containing urea, ceramides or hyaluronic acid 2 weeks prior to Day 0.
  Use of anti-histamines for atopic dermatitis within 2 weeks of baseline.
  Significant uncontrolled cardiovascular (a history of ECG abnormalities that are clinically significant in the opinion of the investigator), neurologic, malignant, psychiatric, respiratory or hypertensive disease, as well as diabetes and arthritis.
  Medical history of chronic infectious disease (e.g., hepatitis B, hepatitis C or infection with human immunodeficiency virus).
  History of clinically significant drug or alcohol abuse in the last year prior to Day 0 (baseline).
Study Restrictions
  Each subject will be questioned on the specific points listed below prior to drug administration. If a subject admits a non-compliance with these restrictions, the Principal Investigator (or designee) and/or the sponsor will decide whether or not the subject will be permitted to remain in the study. Non-compliance with these restrictions will be recorded.
  Subjects will be instructed to abstain from planning a trip to sunny climate or use of tanning equipment between screening and follow-up visits.
  Subjects will be instructed to abstain from using any drugs/treatments that may influence atopic dermatitis (refer to exclusion criteria and prohibited therapies or procedures section) throughout the study.
  Subjects will be required to start fasting at least 8 hours before drug administration upon waking. Fasting will continue for at least 60 minutes following drug administration, after which subject can have breakfast. Water will be allowed at all times during the fasting period, but no other fluids will be permitted. Medication(s) for other conditions that are permitted in the study can be taken as usual.
  For Baseline (Day 0), week 4 and week 8 visits, a blood draw will be performed for PK analysis. PK samples must be taken pre-dose; therefore, study drug administration will occur during the visit for Day 0 and week 4 visits. Because dosing will occur at the clinic on Day 0 and week 4, subjects will be required to fast for at least 8 hours prior to study drug administration and will be allowed to have a meal 60 minutes after study drug administration.
Discontinuations
  Subjects have the right to withdraw from the study at any time for any reason without penalty. The investigator also has the right to withdraw subjects from the study if he feels it is in the best interest of the subject or if the subject is uncooperative or non-compliant. It is understood by all concerned that an excessive rate of withdrawal can render the study un-interpretable; therefore, unnecessary withdrawal of subjects should be avoided. Should a subject decide to withdraw, all efforts will be made to complete and report the observations, particularly the follow-up examination, as thoroughly as possible.
  The investigator or one of his or her staff members should contact the subject either telephone or through a personal visit to determine as completely as possible the reason for the withdrawal, and record the reason in subject's source document and CRF. A complete final early termination (week 8) evaluation at the time of the subject's withdrawal should be made with an explanation of why the subject is withdrawing from the study. If the reason for removal of a subject is an adverse event or an abnormal laboratory test result, the principal specific event or test will be recorded. Subjects who discontinue the study before week 8 visit will be asked, if they agree, to come for a last assessment (early termination visit).

Reasons for Discontinuation Include:

The investigator decides that the subject should be withdrawn. If this decision is made because of a serious or persistent adverse event, laboratory abnormality, or intercurrent illness, the study drug is to be discontinued and appropriate measures are to be taken. The investigator will notify the Sponsor or designee immediately.

The subject or attending physician requests that the subject be withdrawn from the study.

The subject for any reason requires treatment with another therapeutic agent that has been demonstrated to be effective for treatment of the study indication. In this case, discontinuation from the study occurs immediately upon introduction of the new agent.

The subject is lost to follow-up, in this case, a reasonable attempt to contact the subject and ascertain his/her status must be made and these attempts must be documented.

Serious protocol violation, including persistent non-compliance.

The Sponsor or Regulatory Authorities, for any reason, stops the study. All subjects will be discontinued from the study and notified of the reasons for the discontinuation.

Pregnancy at any time during the study.

Other: the subject may withdraw from the study for any other reason, including withdrawal of consent.

Treatment

Treatment Administration

Subjects who fulfill all the inclusion and none of the exclusion criteria may be accepted in the study. Each subject must read and sign an informed consent form prior to any screening procedures being performed. This study involves a comparison of DS107G (2 g) with placebo, administered orally once daily upon waking for a total duration of 8 weeks. The last study drug administration should occur on the day preceding week 8 visit/Early Termination (ET) visit. Subjects will be randomized to one of the two treatment groups in a 1:1 ratio:

Treatment group A: 2 grams DS107G (4 capsules).
Treatment group B: 2 grams placebo capsules (4 capsules).

Subjects will be required to start fasting at least 8 hours before drug administration upon waking. Fasting will continue for at least 60 minutes following drug administration, after which subjects can have breakfast. Water will be allowed at all times during the fasting period, but no other fluids will be permitted. Medication(s) for other conditions that are permitted in the study can be taken as usual.

Blister packs will consist of 7 rows of 4 capsules. Each row constitutes one daily dose. Subjects will be instructed to take the 4 capsules from left to right, top to bottom.

Study Treatment

DS107G capsules will be provided as opaque, oval soft gelatin capsules containing 500 mg of DGLA free fatty acid (FFA).

Placebo capsules will be also provided as opaque, oval soft gelatin capsules containing 500 mg of liquid paraffin.

DS107G capsules will be supplied in manufactured form (blinded), packaged in aluminum foil blisters of 28 units. Placebo will be presented in identical blisters and packs and stored/packaged the same as DS107G capsules. Study medication will be labelled according to US and Canadian regulations.

The study medication will be provided by the sponsor to the investigator and will be kept, on site, in a locked room or cabinet with limited access. DS107G and placebo capsules should be stored at a controlled room temperature between 15-30° C. and will only be supplied to subjects in the trial under the supervision of the investigator.

Study drug will be dispensed by the study site to the subject at each study visit. Subjects are to return all study drug blister packs (used and unused) to the study site. The capsules within blister packs will be counted prior to dispensing and upon return and the counts will be recorded in the source documents and eCRF. Each subject is to be instructed on the importance of returning study drug at the next study visit. If a subject does not return study drug, he/she will be instructed to return it as soon as possible.

The investigator is responsible for maintaining accurate records of the study medication received initially, the study drug dispensed/used, the returned medication by subjects and the medication destroyed or returned to the Sponsor or designee. All study drug accountability forms and treatment logs must be retained in the Investigator's study file. These records must be available for inspection by the Sponsor, its designees or by regulatory agencies at any time.

Used drug boxes/blister packs will be stored safely until destruction and must be accounted for by the investigator. The study monitor will perform drug accountability for all study drug at the site and assist in returning study drug, including used and unused study drug to the Sponsor or designee. After verification of the drug accountability by the sponsor, the investigator will ensure proper destruction or return of the remaining study product.

Any study medication accidentally or deliberately destroyed will be accounted for. Any discrepancies between amounts dispensed and returned will be explained.

Drug inventory and accountability records will be maintained at each site as per GCP/ICH guidelines. Approximately 100 patients will be randomized into double-blind treatment groups in a 1:1 ratio by an Interactive Web Response System (IWRS) or Interactive Voice Response System (IVRS), as follows:

Treatment group A: 2 grams DS107G (4 capsules).
Treatment group B: 2 grams placebo capsules (4 capsules).

A randomization list permuted blocks and stratified by site will be generated by Dignity Sciences or its designee. The randomization schedule with study drug assignments will be generated prior to the start of the study and will be known only to the individuals responsible for labeling the study drug. The IVRS or IWRS will assign a study drug kit number to each subject and the contents will be based on the randomization code.

At the investigational site, each subject will be assigned a patient identifier number during screening that will be used on all patient documentation. The patient identifier number will contain the site number and the patient number assigned in numerical order at the screening visit (e.g.: 02-010 for the tenth patient screened at the site #02). Numbers will be assigned in ascending order starting with 001.

Rationale for Selection and Timing of Doses in the Study

Doses up to 4 g have been well tolerated in healthy subjects. The dose of 2 g has been selected as the tested dose in the current study based primarily on the pharmacokinetic results from the Phase I trial which suggested saturable skin levels of total DGLA with repeated oral dosing of greater than 2 g per day. In addition the following factors were considered:

there were less frequent transient gastrointestinal instances recorded at a dose of 2 g compared to 4 g daily.

the number of capsules (4) administered daily. A higher dose would be possible but is deemed less desirable as too many capsules may have a negative impact on patient adherence to treatment.

Breaking of Study Blinding

At all times, treatment and randomization information will be kept confidential and will not be released to the investigator, the study staff, the CRO or the sponsor's study team until following the conclusion of the study.

Blinding codes should only be broken in emergency situations for reasons of subject safety. The method will be either a manual or electronic process. When the blind for a subject has been broken, the reason must be fully documented. Whenever possible, the investigator should contact the Sponsor or its designee before breaking the blind. If the blind is broken, the investigator should promptly inform the Medical Monitor. Documentation of breaking the blind should be recorded with the date and time the blind was broken, and the names of the personnel involved.

The subject for whom the blind has been broken will be discontinued from the study and undergo the early termination (ET) procedures (Week 8 visit). In cases where there are ethical reasons to have the subject remain in the study, the investigator must obtain specific approval from the Sponsor or its designee for the subject to continue in the study.

Concomitant Therapy

All medications (including over-the-counter drugs, vitamins, and antacids) taken weeks prior to screening and throughout the study must be recorded. All medications taken for atopic dermatitis in the 2 months prior to screening must be recorded.

Medication entries should be specific to the generic name. Trade name may be used for combination drugs. Entries will include the dose, unit, and frequency of administration, route of administration, start date, discontinuation date, and indication. If the medication is discontinued, or the dosage changed, these details must be recorded.

The Investigator should assess any concomitant procedures, medications, and dietary supplements for acceptability that are not explicitly prohibited.

Permitted Therapies

Emollients

Subjects can apply a bland emollient of their choice on their skin, including AD lesions, provided that emollient use is initiated at least 2 weeks prior to Day 0 and continues at the same frequency and on the same skin areas throughout the study. Subjects will be requested to avoid using emollients containing any of the following ingredients:

(1) Urea
(2) Ceramide
(3) Hyaluronic acid

Every effort should be made to keep the same emollient throughout the study. The commercial name of the selected emollient(s) will be recorded in the source document and the eCRF. No other products may be applied to the lesions during the study.

Other Permitted Therapies

Non-sedative anti-histamines (e.g. loratadine, fexofenadine) are allowed during the study only if used to treat medical conditions other than atopic dermatitis. Such medications are allowed during the study only if the subject has been on a stable dose for at least 2 weeks prior to Day 0 and continues to use the same agent everyday throughout the study.

Inhaled and intranasal corticosteroids for stable medical conditions are allowed.

Prohibited Therapies or Procedures

The following topical therapies or procedures are prohibited during the study for all subjects:

Topical medicated treatments that could affect atopic dermatitis, including but not limited to:
  topical corticosteroids
  calcineurin inhibitors
  tars
  bleach
  antimicrobials
  bleach baths
  Any topical product containing urea, ceramides or hyaluronic acid
  Systemic therapy that could affect atopic dermatitis, e.g. retinoids, calcineurin inhibitors, methotrexate, cyclosporine, hydroxycarbamide (hydroxyurea), azathioprine and oral/injectable corticosteroids
  Anti-histamines (except non-sedative anti-histamine)
  Any biological agent
  UVA or UVB phototherapy
  Psoralen+ Ultraviolet A (PUVA) therapy
  Excessive sun exposure or use of tanning booth
  Any investigational agent Assessment of Compliance Treatment compliance will be assessed at each visit by direct questioning, review of the subject's compliance log and capsule count, and will be based on the latter. Subjects will be given a paper diary at each visit along with study medication. Subjects will indicate any missed doses on the diary, as well as the timing of the last food ingestion prior to study drug administration and food ingestion following study drug administration. Subjects will be instructed to bring all capsules and blister packs (used and unused) and compliance log to the next study visit. Any deviation from the prescribed dosage regimen will be recorded in the source document and in the eCRF. Subjects who are significantly noncompliant will be counseled.

Study Procedures

Please refer to Appendix A for a flowchart of procedures to perform at each visit.

Screening, Visit 1 (Day −30 to −1)

Screening evaluation will only be performed after the subject has agreed to participate and has signed and dated the informed consent form. No treatment or trial related procedures will be initiated before the informed consent is signed. Day 0 visit must be performed, at the latest, 30 days after the screening visit.

Screening evaluation will be performed according to inclusion and exclusion criteria. If the subject fulfils all inclusion criteria and no exclusion criteria, the subject may be included in the study.

The following procedures will be performed at the screening visit:

Informed consent;
Review of Inclusion-Exclusion criteria, including review of Hanifin and Rajka criteria (Appendix G);
Assign subject identifier number (Site number—Subject number);
Demographics;
Concomitant medications;

Medical/surgical history;
Physical examination;
Vital signs;
BMI;
Safety labs (chemistry, coagulation, hematology and urinalysis);
Serum pregnancy test (women of childbearing potential only) and FSH level test for women greater than 40 and less than 60 years of age who have had a cessation of menses for at least 12 months but less than 24 months;
BSA evaluation;
IGA;

Baseline, Visit 2 (Day 0)

Subjects are required to fast for at least 8 hours prior to study drug administration. They will be allowed to have a meal 60 minutes after study drug administration.

The following procedures will be performed at this visit:
(1) Confirm eligibility with inclusion and exclusion criteria
(2) Update or confirm medical/surgical history
(3) Concomitant medications
(4) Vital signs
(5) BMI
(6) Safety labs and biomarkers of inflammation (chemistry, coagulation, hematology, urinalysis, and interleukin profile).
(7) Urine pregnancy test (women of childbearing potential only)
(8) Pre-dose blood draw pharmacokinetics
(9) Blood draw total fatty acid profile
(10) BSA evaluation
(11) IGA
(12) EASI assessment
(13) SCORAD assessment (including VAS pruritus assessment)
(14) POEM questionnaire
(15) DLQI questionnaire
(16) TEWL assessment (for selected sites only)
(17) Randomize subject in IVRS/IWRS
(18) Study drug administration
(19) Dispensing of study drug
(20) Dispensing of Subject Compliance Log
(21) Adverse events evaluation (after first study drug administration) Week 2, Visit 3 (Day 14±2 days)

The following procedures will be performed at this visit:
(1) Vital signs
(2) Urine pregnancy test (women of childbearing potential only)
(3) BSA evaluation
(4) IGA
(5) EASI assessment
(6) SCORAD assessment (including VAS pruritus assessment)
(7) POEM questionnaire
(8) DLQI questionnaire
(9) TEWL assessment (for selected sites only)
(10) Collection and dispensing of study drug Review, collection and dispensing of Subject Compliance log
(11) Capsule count
(12) Concomitant medications
(13) Adverse events evaluation Week 4, Visit 4 (Day 28±2 days).

Subjects are required to fast for at least 8 hours prior to study drug administration. They will be allowed to have a meal 60 minutes after study drug administration.

The following procedures will be performed at this visit:
(1) Vital signs
(2) Urine pregnancy test (women of childbearing potential only)
(3) Physical examination
(4) Safety labs (chemistry, coagulation, hematology, urinalysis and interleukin profile)
(5) Pre-dose blood draw pharmacokinetics (if study medication was taken prior to the visit, subject must come back the next day)
(6) Blood draw total fatty acid profile
(7) BSA evaluation
(8) IGA
(9) EASI assessment
(10) SCORAD assessment (including VAS pruritus assessment)
(11) POEM questionnaire
(12) DLQI questionnaire
(13) TEWL assessment (for selected sites only)
(14) Study drug administration (instruct subject that last dose should occur on the day preceding week 8 visit)
(15) Collection and dispensing of study drug
(16) Review, collection and dispensing of Subject Compliance log
(17) Capsule count
(18) Concomitant medications
(19) Adverse events evaluation.

Week 8, Visit 5 (Day 56±2 days) (End of Treatment/Early Termination Visit).

The following procedures will be performed at this visit:
(1) Ongoing medical history review
(2) Vital signs
(3) Physical examination
(4) BMI
(5) Safety labs (chemistry, coagulation, hematology and urinalysis)
(6) Serum pregnancy test (women of childbearing potential only)
(7) Blood draw pharmacokinetics (if study medication was taken prior to the visit, subject must come back the next day)
(8) Blood draw total fatty acid profile
(9) BSA evaluation
(10) IGA
(11) EASI assessment
(12) SCORAD assessment (including VAS pruritus assessment)
(13) POEM questionnaire
(14) DLQI questionnaire
(15) TEWL assessment (for selected sites only)
(16) Collection of study drug
(17) Review and collection of Subject Compliance log
(18) Capsule count
(19) Concomitant medications
(20) Adverse events evaluation Follow-up/Week 10, Visit 6 (Day 70±3 days).

The following procedures will be performed at this visit:
(1) Ongoing medical history review
(2) Vital signs
(3) Physical examination
(4) Safety labs (chemistry, coagulation, hematology and urinalysis): only if clinically significant change from baseline in safety lab results at week 8
(5) Urine pregnancy test (women of childbearing potential only)
(6) BSA evaluation
(7) IGA
(8) EASI assessment (9) SCORAD assessment (including VAS pruritus assessment)
(10) POEM questionnaire
(11) DLQI questionnaire
(12) TEWL assessment (for selected sites only)
(13) Concomitant medications
(14) Adverse events evaluation
(15) Early termination visit.

In the case the subject ends the study before completion, the procedures listed at Week 8 visit should be completed.

Study Assessments

Efficacy Assessments

Clinical evaluations of atopic dermatitis will be performed by an experienced and qualified dermatologist (board certified or equivalent). To assure consistency and reduce variability, the same assessor should perform all assessments on a given subject whenever possible.

Investigator's Global Assessment

The Investigator's Global Assessment (IGA) of Disease Severity (Appendix B) will be assessed at each visit. The IGA is a global assessment of the current state of the disease. It is a 6-point morphological assessment of overall disease severity and will be determined according to the following definitions: 0 (clear), 1 (almost clear), 2 (mild), 3 (moderate), 4 (severe) and 5 (very severe). In order to be eligible, subjects must have an IGA score≥3 at Baseline visit (Day 0).

Eczema Area and Severity Index (EASI)

The Eczema Area and Severity Index (EASI) will be assessed at each visit, except screening visit. It quantifies the severity of a subject's atopic dermatitis based on both lesion severity and the percent of BSA affected. The EASI is a composite score ranging from 0-72 that takes into account the degree of erythema, induration/papulation, excoriation, and lichenification (each scored from 0 to 3 separately) for each of four body regions, with adjustment for the percent of BSA involved for each body region and for the proportion of the body region to the whole body. A detailed procedure of EASI score calculation is provided in Appendix C.

Body Surface Area (BSA)

The overall BSA affected by AD will be evaluated (from 0 to 100%) at each visit. One patient's palm represents 1% of his/her total BSA. For all study visits except at screening, the BSA of involved skin will be measured with the SCORAD measurement (see below for description) and evaluated as a separate endpoint. In order to be eligible, subjects must have a BSA of at least 10% at Baseline visit (Day 0).

SCORing Atopic Dermatitis (SCORAD) SCORAD will be measured at each visit, except the screening visit. The SCORAD grading system was developed by the European Task Force on Atopic Dermatitis (1993) and has been a standard tool to assess the AD severity in clinical studies in Europe. Six items (erythema, edema/papulation, oozing/crusts, excoriation, lichenification, and dryness) will be selected to evaluate the AD severity. The overall BSA affected by AD will be evaluated (from 0 to 100%) and included in the SCORAD scores. Loss of sleep and pruritus will be evaluated by patients on a visual analog scale (0-10). The sum of these measures represents the SCORAD which can vary from 0 to 103. The detailed procedure of SCORAD score calculation is provided in Appendix D.

Visual Analog Scale of Pruritus

For all study visits except screening, the pruritus severity score will be recorded with the SCORAD measurement and this will be evaluated as a separate endpoint. This will be evaluated by asking subjects to indicate on the 10-cm scale (0-10) of the assessment form the point corresponding to the average value for the last three days/nights.

Patient-Oriented Eczema Measure (POEM)

The Patient-Oriented Eczema Measure (POEM) will be assessed at each visit, except screening visit. The POEM developed by Charman et. al. is a self-assessment of disease severity by the patient. POEM has a maximum value of twenty eight based on the patient's response to seven questions scored according to the following scale:
No Days=0
1-2 Days=1
3-4 Days=2
5-6 Days=3
Everyday=4

A detailed description of the POEM assessment is provided in Appendix E.

Dermatology Quality of Life (DLQI) Questionnaire

The DLQI is a simple 10-question validated questionnaire which will be completed at each visit, except screening. The questionnaire is provided in Appendix F.

Transepidemal Water Loss (TEWL) (at Selected Sites Only)

The clinical severity of AD and associated effect on skin barrier function will be evaluated at each visit, except the screening visit. This evaluation will be performed at selected sites that have demonstrated previous experience with this device.

At Baseline (Day 0), the investigator will select three representative areas of active AD for each subject; the location of these sites will be recorded. At subsequent visits, TEWL readings for each area of AD will be taken in standard room ambient conditions (22-25° C., 40-60% relative humidity); the mean of the TEWL measurements will be used for the analyses.

Safety Assessments

Vital Skins

The following vital signs will be recorded at every visit in a seated position, after having sat calmly for at least 5 minutes: systolic and diastolic blood pressure (mmHg), pulse (bpm), body temperature (° C.) and respiratory rate (breath/min).

Weight (kg) and Height (cm) will be collected to calculate the BMI, and will be recorded at the Screening, Baseline and week 8 visits. The height will only be recorded once at the screening visit and the same value will be used for BMI calculation at baseline and Week 8 visits.

Any abnormal finding related to vital signs that the investigator considers to be clinically significant, must be recorded as an AE.

Physical Examination

The following sites/systems will be included in the physical examination. Each system will be scored as normal/abnormal (non-clinically significant or clinically significant). Pertinent details must be recorded for any clinically significant findings.
(1) General appearance
(2) Dermatological (except Atopic dermatitis)
(3) Head, Eyes, Ears, Nose, Throat (HEENT)
(4) Respiratory
(5) Cardiovascular
(6) Abdominal
(7) Neurological
(8) Musculoskeletal
(9) Lymphatic Clinical Laboratory Tests Laboratory tests will be performed at screening, Day 0, Week 4 and Week 8. If Week 8 results indicate a clinically significant change from baseline, laboratory tests will also be performed at Week 10. The tests will include urinalysis, hematology with differential and coagulation testing, a standard chemistry panel (chemistry includes liver function tests and cholesterol), coagulation, serum pregnancy test (screening and week 8/Early termination visits) for women of childbearing potential (WOCBP). At baseline (Day 0), week 2, week 4 and week 10 visits, a urine pregnancy test will be performed for women of childbearing potential (conducted at the investigator site). At screening visit, FSH levels will be tested for women greater than 40 and less than 60 years of age who have had a cessation of menses for at least 12 months but less than 24 months. The specific tests in these panels are listed below in Table 8:

TABLE 8

Clinical Laboratory Testing

| Laboratory testing | Tests included |
|---|---|
| Hematology | Basophils, Eosinophils, HCT, HGB, Lymphocytes, MCH, MCV, Monocytes, Neutrophils, platelets, RBC, WBC |
| Coagulation panel (frozen) | APTT, INR, PT |
| Serum Chemistry | Albumin, Alkaline Phosphatase, ALT, AST, Chloride, Cholesterol (non-fasting), CK, Creatinine (Enzymatic), GGT, Glucose Random, LDH, Potassium, Sodium, Total Bilirubin, Triglycerides, Urea (BUN), Uric Acid β-hCG for females of childbearing potential (Screening and week 8/Early termination) |
| Urinalysis | Blood, Glucose, pH, Protein |
| Laboratory Tests Required at Screening only | FSH levels for women greater than 40 and less than 60 years of age who have had a cessation of menses for at least 12 months but less than 24 months. |

Total and Free DGLA Plasma Levels

At Baseline, week 4 and week 8 visits, blood draws will be performed prior to study drug administration (no study drug administration at week 8 visit). If a subject comes to the clinic after taking their daily dose of study medication, this subject will be required to come back the following day for PK blood draws. Total DGLA and free DGLA trough plasma levels will be measured. A second blood draw will be performed for later evaluation of total fatty acid profile in plasma. The blood draw for serum chemistry analysis will be split in two aliquots for chemistry analysis and later evaluation of interleukins.

The date and time of the subject's last dose at home before the visit will be recorded accurately. The study site will instruct subjects not to take their daily study drug dose at home for week 4 visit. Dosing will occur in the clinic during the study visit. The exact time of the sample collection must be recorded.

Blood samples will be processed as soon as possible, no later than 1 hour after blood collection. The plasma obtained will be transferred in polypropylene tubes. Each tube will be labeled in order to identify the analyte to be assayed. All samples will be frozen in an upright position. The detailed instruction for PK, Total Fatty Acid and interleukin sample collection, processing, storage and shipment will be provided in the central laboratory manual. The labels on each tube will include at least the following information:
(1) Study protocol
(2) Site number
(3) Subject identification number
(4) Visit name
(5) Analyte name
(6) Primary (A) or Duplicate (B)

Shipment of the experimental samples will be shipped to ICON Central Laboratories.

Detailed instructions for shipment will be provided in the central laboratory manual. Samples will then be shipped to the analytical facility and will be analyzed using a validated analytical method in compliance with their standard operating procedures.

Blood specimens for PK analysis will be maintained in a blinded fashion.

Adverse Events

An adverse event is any untoward medical occurrence in a patient administered a pharmaceutical product, without regard to the possibility of a causal relationship with this treatment.

Investigators are responsible for monitoring the safety of subjects who are participating in this study and for alerting the Sponsor of any event that seems unusual, even if this event may be considered an unanticipated benefit to the subject. The investigator is responsible for appropriate medical care of subjects during the study.

The investigator remains responsible for following through an appropriate health care option, adverse events that are serious or that caused the subject to discontinue before completing the study. The subject should be followed until the event is resolved or stable. Follow-up frequency is left to the discretion of the investigator.

Safety will be evaluated by collecting adverse events, vital signs, performing physical examinations and evaluating laboratory results. The reported adverse events will be coded according to MedDRA terminology.

Prior to enrollment, study site personnel will note the occurrence and nature of each subject's medical condition(s) in the appropriate section of the source document and CRF. During the study, site personnel will again note any change in the condition(s) and the occurrence and nature of any adverse events.

If a subject experiences an adverse event after the first dose of the study drug, the event will be recorded as an adverse event in the source document and CRF. All AEs will be described in the source documents and in the CRF.

Adverse Events Causality

The investigator will establish causality of the AE to experimental treatment. The investigator should take into account the subject's history, most recent physical examination findings, and concomitant medications.

The following definitions will be used to determine causality of an AE:

Not related: temporal relationship of the onset of the AE, relative to the experimental treatment is not reasonable or another cause can explain the occurrence of the AE.

Related: temporal relationship of the onset of the AE, relative to the experimental treatment is reasonable, follows a known response pattern to the treatment, and an alternative cause is unlikely.

Adverse Events Severity

The intensity of an AE is an estimate of the relative severity of the event made by the investigator based on his or her clinical experience and familiarity with the literature. The following definitions are to be used to rate the severity of an AE:

Mild: The symptom is barely noticeable to the subject and does not influence performance of daily activities. Treatment is not ordinarily indicated.

Moderate: The symptom is sufficiently severe to make the subject uncomfortable, and performance of daily activities is influenced. Treatment may be necessary.

Severe: The symptom causes severe discomfort, and daily activities are significantly impaired or prevented. Treatment may be necessary.

Serious Adverse Events

If a patient experiences a serious adverse event after the first dose of the study drug, the event will be recorded as a serious adverse event. All AEs will be described in the source documents and in the CRF.

A serious adverse event (experience) or reaction is any untoward medical occurrence that at any dose:
  results in death,
  is life-threatening,
  requires in-subject hospitalization or prolongation of existing hospitalization,
  results in persistent or significant disability/incapacity, or
  is a congenital anomaly/birth defect.

The term "life-threatening" in the definition of "serious" refers to an event in which the subject was at risk of death at the time of the event; it does not refer to an event which hypothetically might have caused death if it were more severe.

Medical and scientific judgment should be exercised in deciding whether expedited reporting is appropriate in other situations, such as important medical events that may not be immediately life-threatening or result in death or hospitalization but may jeopardize the subject or may require intervention to prevent one of the other outcomes listed in the definition above. These should also usually be considered serious.

Examples of such events are intensive treatment in an emergency room or at home for allergic bronchospasm; blood dyscrasias or convulsions that do not result in hospitalization; or development of drug dependency or drug abuse.

Pregnancy Reporting

If a subject becomes pregnant during the study, the subject should inform the study site as soon as possible. Upon confirmation of the pregnancy, the subject must be withdrawn from study drug but may continue study participation. The Investigator must complete a study-specific Pregnancy Form upon confirmation of a pregnancy and send it to Innovaderm Research within 24 hours of confirmation of the pregnancy. Innovaderm Research will report all cases of pregnancy to the Sponsor in a timely manner (contact information to be used are the same as for SAE reporting). Post-treatment follow-up should be done to ensure subject safety. Pregnancy is not itself an AE or SAE; however, maternal/fetal complications or abnormalities will be recorded as AEs or SAEs, as appropriate. The investigator will follow the pregnancy until completion (or until pregnancy termination) and notify Innovaderm Research of the outcome as a follow up to the initial Pregnancy Form.

Data Quality Assurance/Site Monitoring

During the study, monitoring visits will be conducted at regular intervals. The monitoring visits will be conducted to ensure protocol adherence, quality of data, accuracy of entries in the eCRF, drug accountability, compliance with regulatory requirements and continued adequacy of the investigational site and its facilities.

The site may be audited and/or monitored by a quality assurance officer named by the Sponsor and/or regulatory authorities may wish to perform on-site audits. The investigator will be given notice before an audit occurs and will be expected to cooperate with any audit, provide assistance and documentation (including source data) as requested.

Data Collection and Retention

Subject data will be entered by site personnel using Medrio eClinical Overnight, a web based electronic data capture (EDC) and reporting system. This application will be set up for remote entry. Medrio Inc. are the developers and owners of Medrio eClinical Overnight. The EDC software has been fully validated and conforms to 21 CFR Part 11 requirements. Investigator site staff will not be given access to the EDC system until they have been fully trained by the Sponsor or delegate. Designated investigator staff will enter the data required by the protocol into the eCRFs using this web based application. Automatic validation programs check for data discrepancies in the eCRFs and, by generating appropriate error messages, allow modification or verification of the entered data by the investigator staff before confirming the data. The investigator must certify that the data are complete and accurate by applying an electronic signature to the eCRFs.

The investigator must maintain source documents for each subject in the study, consisting of case and visit notes (clinical medical records) containing demographic and medical information and the results for any tests or assessments. All information on the eCRFs must be traceable to these source documents in the subject's file. Data not requiring a written or electronic record will be defined before study start and will be recorded directly on the eCRFs, which will be documented as being the source data.

The data collected will be encoded and stored electronically in a database system. Validated data may subsequently be transferred to the sponsor.

Confidentiality of Trial Documents and Subject Records

The investigator must assure that the subjects' anonymity will be maintained and that their identities are protected from unauthorized parties. On CRFs or other document submitted to the Sponsor, subjects should not be identified by their names, but by an identification code. The Investigator should keep a subject enrolment log relating codes with the names of subjects. The Investigator should maintain documents not for submission to the sponsor e.g., subjects' written consent forms, in the strictest confidence.

Investigator's Files/Retention of Documents

The Investigator must maintain adequate and accurate records to enable the conduct of the study to be fully documented and the study data to be subsequently verified. These records include, but are not limited to, the identity of all participating subjects, all original signed informed consent documents, copies of all CRFs, safety reporting forms, source documents, and detailed records of treatment disposition, and adequate documentation of relevant correspondence. These documents should be classified into two different separate categories: Investigator Study File and Subject Clinical Source Documents.

The records should be retained by the investigator according to International Conference on Harmonisation (ICH), local regulations, or as specified in the Clinical Trial Agreement (CTA), whichever is longer.

Sample Size and Statistical Methods

Determination of Sample Size

The primary endpoint can be translated as a responder analysis where a subject will be classified as Responder if he/she achieves an IGA score of 0 (clear) or 1 (almost clear) at Week 8, considering a 2-point decrease from baseline. A sample size of 45 subjects will have a power of 80% to detect a statistically significant difference of 25% between responders from treated group and from the placebo group, based on a chi-square test and an alpha of 0.05. Based on the literature review, it is expected that the placebo could reach up to 7%, so the minimal proportion expected in the treated group should be at least 32%. Allowing for 10% drop-out, a total of 100 subjects should be enrolled in the study.

Statistical and Analytical Plans

Continuous variables will be summarized in tables and will include the number of subjects, mean, standard deviation, median, minimum, maximum and inter-quartile range. Categorical variables will be presented in tables as frequencies and percentages.

All statistical tests will be two-sided and will be performed with a significant level of 0.05, unless otherwise specified.

Subject Disposition

Efficacy will be evaluated on the basis of the ITT population and analyses will be performed based on the randomized treatment and not on the treatment received.

The per-protocol (PP) population will include all subjects who were randomized with no significant protocol deviations. The specific criteria for the PP population and the ITT population will be detailed in a separate statistical analysis plan.

The safety population will be defined as all subjects who received at least one dose of the medication. Analysis will be done according to the actual treatment they received.

Efficacy Analysis

The primary endpoint can be translated as a responder analysis where a subject will be classified as Responder if he/she achieves an IGA score of 0 (clear) or 1 (almost clear) at Week 8, considering a 2-point decrease from baseline. The comparison between groups for the primary endpoint will be done using a chi-square test. A sensitivity analysis to examine the contribution of site in the comparisons will be conducted using a Cochran-Mantel-Haenszel test where the site will be used as the stratification factor. The primary efficacy analysis will be done using observed values and a supportive analysis will be conducted with a tipping point analysis, a strategy used to evaluate the impact of missing values. Missing values will be set to responder/non-responder successively and decisions based on p-values will be plotted. Details of this strategy will be presented in the statistical analysis plan. There will be no imputation for missing data at other visits. The analyses will be done using the ITT population and will serve as the primary analysis while the analysis of the primary endpoint using the PP population will be used a sensitivity analysis.

The secondary endpoints involving change from baseline will be analyzed using an analysis-of-covariance (ANCOVA) including the change from baseline as the dependent, the site and treatment group and site as fixed effects, and the baseline value as covariate. Ls-means and 95% CI will be presented along with corresponding p-value from the comparison of treatment. The secondary endpoints involving proportion will be analyzed using a Cochran-Mantel-Haenszel test stratified by site and p-value will be presented.

Analyses for the secondary endpoints will be done using observed data and no imputation will be used for missing observation.

All details regarding the statistical analyses will be included in a separate statistical analysis plan.

Safety Analysis

All adverse events (AEs) that occur after the first study drug administration during the study will be classified on the basis of Medical Dictionary for Regulatory Activities (MedDRA) terminology. Descriptions of AEs will include the date of onset, the date the AE ended (if it resolved), the severity and seriousness of the AE, the relationship of the AE to study medication, and the outcome. The focus in this protocol will be limited to treatment emergent adverse events.

Reported AEs will be summarized by the number of subjects reporting the events, as well as by System Organ Class, Preferred Term, severity, seriousness, and relationship to study medication. For the summary of AEs by severity, each patient will be counted only once within a System Organ Class or a Preferred Term by using the AEs with the highest intensity within each category for each analysis. For the summary of AEs by relationship to study medication, each patient will be counted only once within a System Organ Class or a Preferred Term by using the AEs with the greatest reported relationship within each category. For the summary of AEs by relationship to study medication and severity, each patient will be counted only once within a System Organ Class or a Preferred Term by using (1) the greatest reported relationship followed by (2) the highest reported intensity.

All information pertaining to AEs noted during the study will be listed by patient, detailing verbatim, System Organ Class, Preferred Term, start date, stop date, intensity, outcome and relationship to study drug. The AE onset will also be shown relative (in number of days) to the day of test article administration. Serious adverse events (SAEs) will be tabulated by treatment group, relationship to the test article, and a reference to the occurrence of the SAEs to the relative day of dosing.

Concomitant medications will be coded with the WHO-Drug Dictionary and listed by subject.

In addition, a list of subjects who discontinued from the study and a list of subjects who experienced SAEs will also be provided.

Results from laboratory analyses and vital signs will be tabulated using descriptive statistics. The value at visit as well as the change from baseline will be presented descriptively.

No inferential statistics will be done on safety variables (TEAEs, concomitant medication, laboratory and vital signs).

Ethics

Local Regulations/Declaration of Helsinki

This study will be conducted in accordance with the ethical principles that have their origin in the Declaration of Helsinki (2008) and that are consistent with "Good Clinical Practice" ICH Tripartite Guideline (July 2002) and the applicable laws and regulations of the country in which the research is conducted, whichever affords the greater protection to the individual.

Ethical Review

It is the understanding of the Sponsor that this protocol (and any amendment) as well as appropriate consent procedures, will be reviewed and approved by a research ethics board/institutional review board (REB/IRB). This Board must operate in accordance with the current Federal regulations. A letter or certification of approval will be sent by the Investigator to the Sponsor prior to initiation of the study, and also whenever subsequent modifications to the protocol are made.

Informed Consent

It is the responsibility of the Investigator, or a person designated by the Investigator (if acceptable by local regulation), to obtain written informed consent from each individual participating in this study after adequate explanation of the aims, methods, objectives and potential hazards of the study. It must also be explained to the subjects that they are completely free to refuse to enter the study or to withdraw from it at any time for any reason.

If new safety information results in significant changes in the risk/benefit assessment or any new information that may affect willingness to continue to participate, the consent form should if necessary be reviewed and updated by the Research Ethics Board/Institutional Review Board. All subjects (including those already being treated) should be informed of the new information, given a copy of the revised form and asked to give their consent to continue in the study.

Appendix A Study Flow Chart

|  | Visit | | | | | |
| --- | --- | --- | --- | --- | --- | --- |
|  | Screening | Baseline | Week 2 | Week 4 Day | Week 8/ ET visit | Follow up visit/Week 10 |
|  | −30 to −1 | 0 | 14 (±2) | 28 (±2) | 56 (±2) | 70 (±3) |
| Informed Consent | X | | | | | |
| Demographics | X | | | | | |
| Medical/Surgical History | X | X | | | | |
| Ongoing medical history $^\gamma$ | | | | | X | X |
| Review Inclusion/Exclusion Criteria | X | X | | | | |
| Hanifin and Rajka criteria | X | | | | | |
| Assign subject identifier number | X | | | | | |
| Randomization | | X | | | | |
| Concomitant Medications | X | X | X | X | X | X |
| Safety labs and inflammation biomarkers: Serum Chemistry (including FSH levels at screening when applicable$^\yen$ and interleukin profile), Coagulation, Hematology, urinalysis | X$^\Phi$ | X | | X | X | (X**)$^\Phi$ |
| Pharmacokinetics (pre-dose blood draw)$^{\dagger\dagger}$ | | X | | X | X | |
| Blood draw for fatty acid profile sample$^{\dagger\dagger}$ | | X | | X | X | |
| Pregnancy Test (β-hCG if female of childbearing potential) * | X | X | X | X | X | X |
| Vital Signs | X | X | X | X | X | X |
| Physical Examination | X | | | X | X | X |
| BMI | X | X | | | X | |
| Study Drug Administration (on site)$^\epsilon$ | | X | | X | § | |
| Dispense Study Drug | | X | X | X | | |
| Collect Study Drug | | | X | X | X | |
| Dispense Subject Compliance Log | | X | X | X | | |
| Collect and Review Subject Compliance Log | | | X | X | X | |
| Capsule count | | | X | X | X | |
| BSA | X | X | X | X | X | X |
| IGA | X | X | X | X | X | X |
| EASI assessment | | X | X | X | X | X |
| SCORAD assessment/VAS pruritus assessment | | X | X | X | X | X |
| POEM questionnaire | | X | X | X | X | X |
| DLQI questionnaire | | X | X | X | X | X |
| TEWL (selected sites only) | | X | X | X | X | X |
| Adverse Events$^\dagger$ | | X$^\dagger$ | X | X | X | X |

$^\yen$ For women greater than 40 and less than 60 years of age who have had a cessation of menses for at least 12 months but less than 24 months
**Only if clinically significant change from baseline in safety lab results at week 8
* Serum pregnancy test at screening and week 8/ET visits, urine test pregnancy for all other visits
$^{\dagger\dagger}$ If a subject took study medication prior to the visit, he/she will be required to come back the following day for PK blood draws.
$^\epsilon$ Subjects must be fasting for at least 8 hours before and 60 minutes after drug administration
§ Subjects will be instructed to take their last study drug dose the day preceding week 8 visit.
$^\dagger$ Collection of AE will start after the first study drug administration
$^\gamma$ Assessment if any ongoing condition has improved since baseline.
$^\Phi$ Interleukin profile will not be evaluated at screening and week 10.

Appendix B—Investigator's Global Assessment

| Score | Grade | Definition |
| --- | --- | --- |
| 0 | Clear | No evidence of disease with the exception of residual pigment changes and/or xerosis |
| 1 | Almost clear | Perceptible erythema, papulation/infiltration |
| 2 | Mild | Mild erythema, papulation/infiltration |
| 3 | Moderate | Moderate erythema, papulation/infiltration |

| Score | Grade | Definition |
| --- | --- | --- |
| 4 | Severe | Severe erythema, papulation/infiltration |
| 5 | Very Severe | Severe erythema, papulation/infiltration with oozing/crusting |

Appendix C—Eczema Area and Severity Index (EASI)

Four anatomic sites—head, upper extremities, trunk and lower extremities—are assessed for erythema, induration (papules), excoriation and lichenification as seen on the day of the examination. The severity of each sign is assessed using a 4-point scale:

0=No symptoms
1=Slight
2=Moderate
3=Marked

The area affected by atopic dermatitis within a given anatomic site is estimated as a percentage of the total area of that anatomic site and assigned a numerical value according to the degree of atopic dermatitis involvement as follows:

0=no involvement
1=<10%
2=10 to <30%
3=30 to <50%
4=50 to <70%
5=70 to <90%
6=90 to 100%

The EASI score is obtained by using the formula
$EASI = 0.1(E_h + I_h + Ex_h + L_h)A_h + 0.2(E_u + I_u + Ex_u + Ex_u)A_u + 0.3(E_t + I_t + Ex_t + Ex_t)A_t + 0.4(E_l + I_l + Ex_l + Ex_l)A_l$ Where E, I, Ex, L and A denote erythema, induration, excoriation, lichenification and area, respectively, and h, u, t, and l denote head, upper extremities, trunk, and lower extremities, respectively.

Appendix D—SCORing Atopic Dermatitis (SCORAD)

Six items (erythema, edema/papulation, oozing/crusts, excoriation, lichenification, and dryness) are selected to evaluate the AD severity. The intensity of each item is graded using a 4-point scale:

0=No symptoms
1=Mild
2=Moderate
3=Severe

The area chosen for grading must be representative (average intensity) for each item. The individual intensity ratings for each item will then be added (ranging from 0-18) and multiplied by 3.5, giving a maximal score of 63.

The overall BSA affected by AD is evaluated (from 0 to 100%) and divided by 5. One patient's palm represents 1% of his/her total BSA. The maximum is 20.

Subjective items include loss of sleep and the occurrence of pruritus. These are evaluated by asking patients to indicate on the 10-cm scale (0-10) of the assessment form the point corresponding to the average value for the last three days/nights. The combined maximum score of these two is 20.

The sum of the above measures represents the SCORAD which can vary from 0 to 103. If the subjective scores of pruritus and loss of sleep are excluded, the SCORAD becomes objective SCORAD (score range 0-83).

Appendix E—Patient-Oriented Eczema Measure (POEM)

Patient ID #:____ ____ - ____ ____ ____    Patient Initials: ____ ____ ____
Visit Day: _____    Visit Date (dd-mmm-yyyy):_____

Please circle one response for each of the seven questions below about your eczema. Please leave blank any questions you feel unable to answer.

Please circle one response for each of the seven questions below about your eczema. Please leave blank any questions you feel unable to answer.

1. Over the last week, on how many days has you skin been itchy because of your eczema?

No days    1-2 days    3-4 days    5-6 days    Every day

2. Over the last week, on how many nights has your sleep been disturbed because of your eczema?

No days    1-2 days    3-4 days    5-6 days    Every day

3. Over the last week, on how many days has your skin been bleeding because of your eczema?

No days    1-2 days    3-4 days    5-6 days    Every day

4. Over the last week, on how many days has your skin been weeping or oozing clear fluid because of your eczema?

No days    1-2 days    3-4 days    5-6 days    Every day

5. Over the last week, on how many days has your skin been cracked because of your eczema?

No days    1-2 days    3-4 days    5-6 days    Every day

6. Over the last week, on how many days has your skin been flaking off because of your eczema?

No days    1-2 days    3-4 days    5-6 days    Every day

7. Over the last week, on how many days has your skin felt dry or rough because of your eczema?

No days    1-2 days    3-4 days    5-6 days    Every day

© C R Charman, A J Venn, H C Williams, December 2004.

Appendix F—Dermatology Life Quality Index (DLQI)

The aim of this questionnaire is to measure how much your skin problem has affected your life OVER THE LAST WEEK. Please check one box for each question.

| | | |
|---|---|---|
| 1. Over the last week, how itchy, sore, painful or stinging has your skin been? | Very much ☐<br>A lot ☐<br>A little ☐<br>Not at all ☐ | |
| 2. Over the last week, how embarrassed or self conscious have you been because of your skin? | Very much ☐<br>A lot ☐<br>A little ☐<br>Not at all ☐ | |
| 3. Over the last week, how much has your skin interefered with you going shopping or looking after your home or yard? | Very much ☐<br>A lot ☐<br>A little ☐<br>Not at all ☐ | Not relevant ☐ |
| 4. Over the last week, how much has your skin influenced the clothes you wear? | Very much ☐<br>A lot ☐<br>A little ☐<br>Not at all ☐ | Not relevant ☐ |
| 5. Over the last week, how much has your skin affected any social or leisure activities? | Very much ☐<br>A lot ☐<br>A little ☐<br>Not at all ☐ | Not relevant ☐ |
| 6. Over the last week, how much has your skin made it difficult for you to do any sport? | Very much ☐<br>A lot ☐<br>A little ☐<br>Not at all ☐ | Not relevant ☐ |
| 7. Over the last week, has your skin prevented you from working or studying?<br>If "No", over the last week how much has your skin been a problem at work or studying | yes ☐<br>no ☐<br>A lot ☐<br>A little ☐<br>Not at all ☐ | Not relevant ☐ |
| 8. Over the last week, how much has your skin created problems with your partner or any of your close friends or relatives? | Very much ☐<br>A lot ☐<br>A little ☐<br>Not at all ☐ | Not relevant ☐ |
| 9. Over the last week, how much has your skin caused any sexual difficulties? | Very much ☐<br>A lot ☐<br>A little ☐<br>Not at all ☐ | Not relevant ☐ |
| 10. Over the last week, how much of a problem has the treatment for your skin been, for example by making your home messy, or by taking up time? | Very much ☐<br>A lot ☐<br>A little ☐<br>Not at all ☐ | Not relevant ☐ |

The aim of this questionnaire is to measure how much your skin problem has affected your life OVER THE LAST WEEK. Please check one box for each question.

Appendix G—Diagnostic Criteria for Atopic Dermatitis

Per Inclusion Criterion 2, a subject is to have a clinical diagnosis of atopic dermatitis according to the criteria of Hanifin and Rajka. The criteria go as follows:

Major Criteria (Must have at Least Three)
  Pruritus
  Typical morphology and distribution:
  Adults: flexural lichenification or linearity
  Children and infants: involvement of facial and extensor surfaces
  Chronic or relapsing dermatitis
  Personal or family history of atopy Minor Criteria (Must have at Least Three)
  Xerosis
  Icthyosis/keratosis pilaris/palmer hyperlinearity
  Immediate (type 1) skin test reactivity
  Elevated serum IgE
  Early age at onset
  Tendency to skin infections (*Staphylococcus aureus*, herpes simplex)/impaired cellular
  Immunity
  Hand/foot dermatitis
  Nipple eczema
  Conjunctivitis
  Dennie-Morgan fold
  Keratoconus
  Anterior subcapsular cataracts
  Orbital darkening
  Facial pallor/erythema
  *Pityriasis alba*
  Anterior neck folds
  Itch when sweating
  Intolerance to wool and lipid solvents
  Perifollicular accentuation
  Food intolerance
  Course influenced by environmental/emotional factors
  White demographic/delayed blanch Example 3

An in vivo investigation of anti-hypertension efficacy following co-administration of DGLA and aspirin in spontaneous hypertensive rats was conducted. This experiment investigated the efficacy of DGLA when co-administered chronically with aspirin to reduce the hypertensive response induced acutely by phenylephrine in spontaneous hypertensive rats. Spontaneously hypertensive adult male rats (250-300 g), bred by Charles River Laboratories, were used for this assay. The animals were identified upon arrival as per CCPA guidelines. The animals were pair-housed by group (low dose+ Aspirin, high dose+ Aspirin or Aspirin alone) for the duration of the oral gavage prior to surgery. All animal care and vivarium maintenance was recorded, with documents kept at the test facility.

The rat is a well-characterized and highly sensitive model for assessment of vascular tension effects and evaluation of efficacy following chronic exposure to a test article. This study design is based on current International Conference on Harmonization (ICH) Harmonized Tripartite Guidelines [ICH S7A] and generally accepted procedures for the testing of pharmaceutical compounds. This nonclinical laboratory study was designed as a non-GLP compliant study and did not require QA involvement.

The concentrations of DGLA to be tested (50 and 500 mg/kg) as well as the concentration of aspirin (10 mg/kg) were selected by the Sponsor based on information available at the time of design of this study. They were selected to cover a range of concentrations useful for the identification of the mechanism of action of the test article.

The concentrations of positive control (carvedilol 0.1 mg/kg) and the hypertensor (phenylephrine 3, 10, and 20 µg/kg) were selected based on literature references. All solution preparations were documented on a Solution Contents Form, defining labelling information and all relevant information on reagents: batch number, storage conditions, contents, and preparation/expiry dates.

The test article was formulated using olive oil as the vehicle. This stock solution was then administered by oral gavage once per day for seven consecutive days. A low and a high dose (50 mg/kg and 500 mg/kg) were tested.

A 5 mg/ml stock solution of Aspirin was prepared by dissolving the appropriate amount of aspirin in 100% DMSO which was then diluted in water. The concentration of DMSO was less than 1%. The appropriate volume was administered by oral gavage to each animal once per day for seven consecutive days. The stock solution was stored at room temperature and was considered stable for the duration of the gavage.

A 0.4 mg/ml stock solution of carvedilol was prepared in PBS (pH=4.00±0.05). The appropriate volume was administered to each animal by an intravenous injection at the end of the experiment on the surgery day. The stock solution was stored at 4° C. and was considered stable for the duration of the experiment.

A stock solution of phenylephrine of 1 mg/ml were prepared in PBS (pH=7.4±0.05). The stock solution was stored at 4° C. The expiration date was set at 14 days after preparation.

Any remaining test article will be destroyed after completion of the study.

Male spontaneous hypertensive rats weighing approximately 300 g arrived at the facility at least two days before beginning the oral gavage. Animals were assigned to one of three groups (low dose+ aspirin, high dose+ aspirin, and aspirin), and were pair-housed during the acclimation period. Each group (n=4) received the appropriate compound by oral gavage using a 16G feeding needle. The stock solution was administered once per day for seven consecutive days. On the seventh day of administration, the animals underwent surgery and hypertensive monitoring.

Rats were anesthetized with a 2.5-3.0% isoflurane-O2 mixture in an induction box. When the animals were removed from the induction box, they were connected onto a nose cone to maintain anesthesia during the tracheotomy. The animals were tracheotomised with an endotracheal tube (7 cm length from connector to the tip made with a PE205 tube from BD and a 16G needle) to facilitate spontaneous breathing, stabilize hemodynamics, and to keep the rat under anesthesia with an isoflurane-O2 mixture. Two catheters were inserted: one in the right femoral artery for systemic arterial pressure (SAP) measurement, and one in the right femoral vein for delivery of the hypertensor and positive control. ECG signals were acquired with ECG contacts placed in a Lead-1 configuration on the anaesthetized animal, and a pulse oxymeter was attached to the animal's hind paw to enable continuous monitoring of the general condition of the rat during the surgical. Following baseline measurements, three doses of phenylephrine (3, 10 and 20 µg/kg) were delivered by an IV bolus injection, leaving 5 minutes between doses. One dose of the positive control, carvedilol (0.1 mg/kg), was administered, following the highest concentration of phenylephrine. After the positive control, 10 µg/kg of phenylephrine was administered again. Blood pressure, systemic arterial pressure (SAP), and heart rate were monitored continuously for a total of half an hour. Hypertension was detected as an increase in diastolic, systolic or mean blood pressure. At the end of the experiment, the animals were euthanized by exsanguination.

The analysis software used was Clampfit 10.2.0.14 by Axon Instruments, installed on networked personal computers running Microsoft Windows. Clampfit 10.2.0.14 has been fully validated in the connected context in which it is used. The graphics software for illustrations is Microsoft Office Excel 2007 installed on networked personal computers running Microsoft Windows. The continuously recorded systemic arterial pressure (SAP) was used to calculate the mean systemic arterial pressure (mSAP) for each condition. The heart rate was monitored continuously from the time anesthesia was induced. One-way ANOVAs, comparing pre- and post-exposure parameters across experimental groups, were analysed. Statistical significance was confirmed at p≤0.05.

Table 9. Arterial pressure and mean systemic arterial pressure (mm Hg) following seven days of gavage, before intravenous doses of phenylephrine.

TABLE 9

| Treatment | Systol/Diastol | Mean systemic arterial pressure |
|---|---|---|
| Olive Oil (vehicle) | 160/100 | 120 |
| DGLA 50 mg/kg | 120/75 | 90 |
| DGLA 500 mg/kg | 135/80 | 98 |
| Aspirin 10 mg/kg | 190/100 | 130 |
| DGLA 50 mg/kg + Aspirin 10 mg/kg | 180/120 | 140 |
| DGLA 50 mg/kg + Aspirin 10 mg/kg | 180/120 | 140 |

*Compared to baseline
** Compared to PHE 20 µg/kg
† Compared to second baseline
§ Compared to Carvedilol Table 10 shows change in mean systemic arterial pressure with intravenous phenylephrine doses following seven consecutive days of gavage with Aspirin at 10 mg/kg/day.

TABLE 10

| Treatment | | | | | | Aspirin 10 mg/kg | | | | |
| --- | --- | --- | --- | --- | --- | --- | --- | --- | --- | --- |
| | | | | | Mean Arterial Pressure | | | | | |
| Conditions | Rat #1 | Rat #2 | Rat #3 | Rat #4 | Rat #5 | Average (mm Hg) | STED | SEM | Test vs baseline | n |
| Baseline | 86.75 | 107.64 | 160.50 | 141.36 | 187.84 | 136.8 | 40.44 | 18.09 | N/A | 5 |
| PHE 3 µg/kg | 97.24 | 122.18 | 168.06 | 150.54 | 192.06 | 146.0 * | 37.33 | 16.69 | 0.006 | 5 |
| PHE 10 µg/kg | 137.63 | 122.18 | 203.75 | 169.61 | 201.69 | 167.0 * | 36.85 | 16.48 | 0.016 | 5 |
| PHE 20 µg/kg | 149.35 | 120.84 | 202.61 | 194.76 | 203.90 | 174.3 * | 37.34 | 16.70 | 0.019 | 5 |
| Baseline | 98.38 | 64.32 | 164.88 | 159.32 | 177.61 | 132.9 ** | 49.03 | 21.93 | 0.002 | 5 |
| Carvedilol 0.1 mg/kg | 57.12 | 44.38 | 145.56 | 134.82 | 115.06 | 99.4 † | 45.95 | 20.55 | 0.015 | 5 |
| PHE 10 µg/kg | 93.22 | 52.61 | 185.63 | 171.45 | 187.96 | 138.2 § | 61.60 | 27.55 | 0.020 | 5 |

FIG. 1 illustrates the change in mean systemic arterial pressure, in mm of Hg, following phenylephrine administration. Five rats received intravenous doses of phenylephrine after seven consecutive days of gavage with Aspirin at 10 mg/kg/day. The mean systemic arterial pressure at each of the three doses of phenylephrine was compared statistically to the first baseline, while the carvedilol condition was statistically compared to the baseline immediately prior to administration, and the final dose of phenylephrine (10 µg/kg) was compared to the positive control condition directly before.

These results demonstrate an increased mean systemic arterial pressure with increasing doses of phenylephrine. All data obtained were statistically different from baseline, confirming the hypertensor effect of phenylephrine in the spontaneously hypertensive rat model fed with aspirin. The effect of phenylephrine was fully reversible; the mean arterial pressure during the second baseline (following 20 µg/kg) was actually quite similar to the original baseline.

Carvedilol caused a significant decrease when added immediately after phenylephrine, confirming its well-known ability to reduce high blood pressure (carvedilol is a non-specific beta blocker/alpha-1 blocker and blocks the binding of phenylephrine to alpha-1 adrenergic receptors). The last addition of phenylephrine, following the carvedilol, caused a limited increase in the mean systemic arterial pressure.

Figure 2:
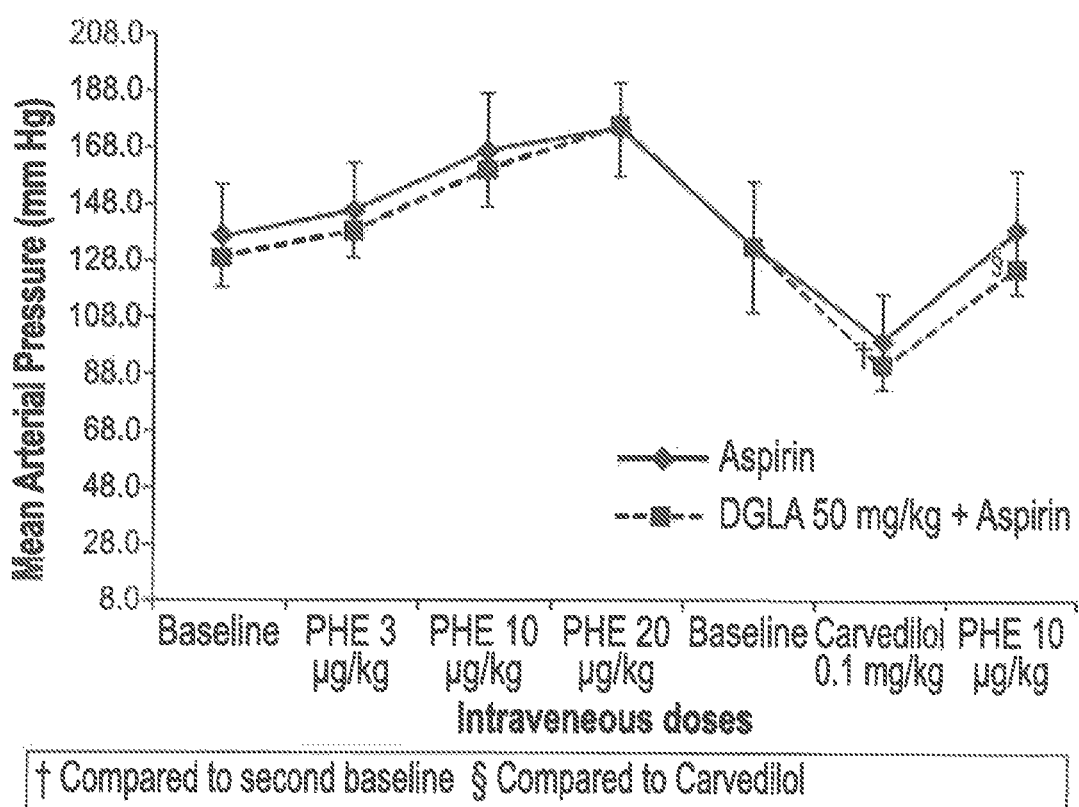
FIG. 2 shows change in mean arterial pressure (mmHg) with intravenous doses of phenylephrine following seven consecutive days of gavage with DGLA at 50 mg/kg+ Aspirin at 10 mg/kg.

FIG. 2. Change in mean arterial pressure (mmHg) with intravenous doses of phenylephrine following seven consecutive days of gavage with DGLA at 50 mg/kg+ Aspirin at 10 mg/kg.

Table 11. Change from baseline in mean arterial pressure with intravenous phenylephrine doses following seven consecutive days of gavage with DGLA at 50 mg/kg+ Aspirin at 10 mg/kg.

The results presented in FIG. 2 demonstrate changes in mean arterial pressure, in mm of Hg, after intravenous doses of phenylephrine in five spontaneously hypertensive rats following seven days of oral feeding with DGLA at 50 mg/kg+ Aspirin at 10 mg/kg. The results for the test article were compared to the data obtained with the aspirin only group (10 mg/kg). Carvedilol was compared to the second baseline, and the last dose of phenylephrine was statistically compared to the carvedilol.

The animals exhibited a dose-dependent increase in blood pressure as phenylephrine concentration was increased. The rats which had been administered DGLA 50 mg/kg and aspirin exhibited an increase in arterial pressure for a given dose of phenylephrine which was essentially the same as that measured in the rats having received Aspirin over 10 days. With the rats which were fed with DGLA at 50 mg/kg in addition of 10 mg/kg of aspirin, there was no significant difference in the mean arterial pressure when compared to the aspirin group at any of the concentrations of phenylephrine. It would thus appear that Aspirin daily prevents the benefits obtained from daily doses of 50 mg/kg DGLA.

Carvedilol caused a significant decrease in blood pressure in DGLA+ aspirin-fed animals. Due to a problem with the anesthesia, rat #3 was not given the last dose of phenylephrine (n=4 for this condition).

Table 12. Change in mean arterial pressure with intravenous phenylephrine doses following seven consecutive days of gavage with DGLA at 500 mg/kg co-administered with Aspirin at 10 mg/kg.

TABLE 11

| Treatment | | | | | | 50 mg/kg + Aspirin 10 mg/kg | | | | |
| --- | --- | --- | --- | --- | --- | --- | --- | --- | --- | --- |
| | | | | | Mean Arterial Pressure | | | | | |
| Conditions | Rat #1 | Rat #2 | Rat #3 | Rat #4 | Rat #5 | Average SAP | STED | SEM | Ttest vs Aspirin | n |
| Baseline | 136.52 | 148.19 | 176.99 | 108.14 | 77.13 | 129.4 | 38.25 | 17.11 | 0.773 | 5 |
| PHE 3 µg/kg | 154.55 | 154.66 | 185.15 | 117.40 | 81.18 | 138.6 | 40.08 | 17.93 | 0.770 | 5 |
| PHE 10 µg/kg | 192.63 | 188.72 | 193.26 | 130.48 | 94.43 | 159.9 | 45.19 | 20.21 | 0.793 | 5 |
| PHE 20 µg/kg | 196.59 | 196.00 | 196.67 | 148.23 | 141.78 | 175.9 | 28.25 | 12.64 | 0.942 | 5 |
| Baseline | 169.28 | 160.97 | 160.79 | 94.77 | 78.64 | 132.9 | 42.68 | 19.09 | 1.000 | 5 |
| Carvedilol 0.1 mg/kg | 115.29 | 97.01 | 126.33 | 59.10 | 58.93 | 91.3 † | 31.30 | 14.00 | 0.006 | 5 |
| PHE 10 µg/kg | 178.71 | 160.97 | n/d | 86.29 | 74.07 | 125.0 § | 52.51 | 26.25 | 0.043 | 4 |

TABLE 12

| Treatment | | | | 500 mg/kg + Aspirin 10 mg/kg | | | | | |
|---|---|---|---|---|---|---|---|---|---|
| | | | | Mean Arterial Pressure | | | | | |
| Conditions | Rat #1 | Rat #2 | Rat #3 | Rat #4 | Average SAP | STED | SEM | Ttest vs Aspirin | n |
| Baseline | 145.62 | 100.15 | 128.35 | 129.60 | 125.9 | 18.90 | 9.45 | 0.638 | 4 |
| PHE 3 µg/kg | 161.09 | 103.72 | 136.18 | 133.59 | 133.6 | 23.49 | 11.74 | 0.584 | 4 |
| PHE 10 µg/kg | 170.69 | 111.08 | 145.53 | 149.12 | 144.1 | 24.66 | 12.33 | 0.325 | 4 |
| PHE 20 µg/kg | 161.17 | 116.35 | 141.85 | 140.72 | 140.0 | 18.36 | 9.18 | 0.140 | 4 |
| Baseline | 120.16 | 83.43 | 88.30 | 85.82 | 94.4 | 17.27 | 8.64 | 0.182 | 4 |
| Carvedilol 0.1 mg/kg | 62.13 | 57.56 | 57.32 | 52.11 | 57.3 † | 4.10 | 2.05 | 0.014 | 4 |
| PHE 10 µg/kg | 95.50 | 65.19 | 80.39 | 58.97 | 75.0 | 16.36 | 8.18 | 0.070 | 4 |

Figure 3:
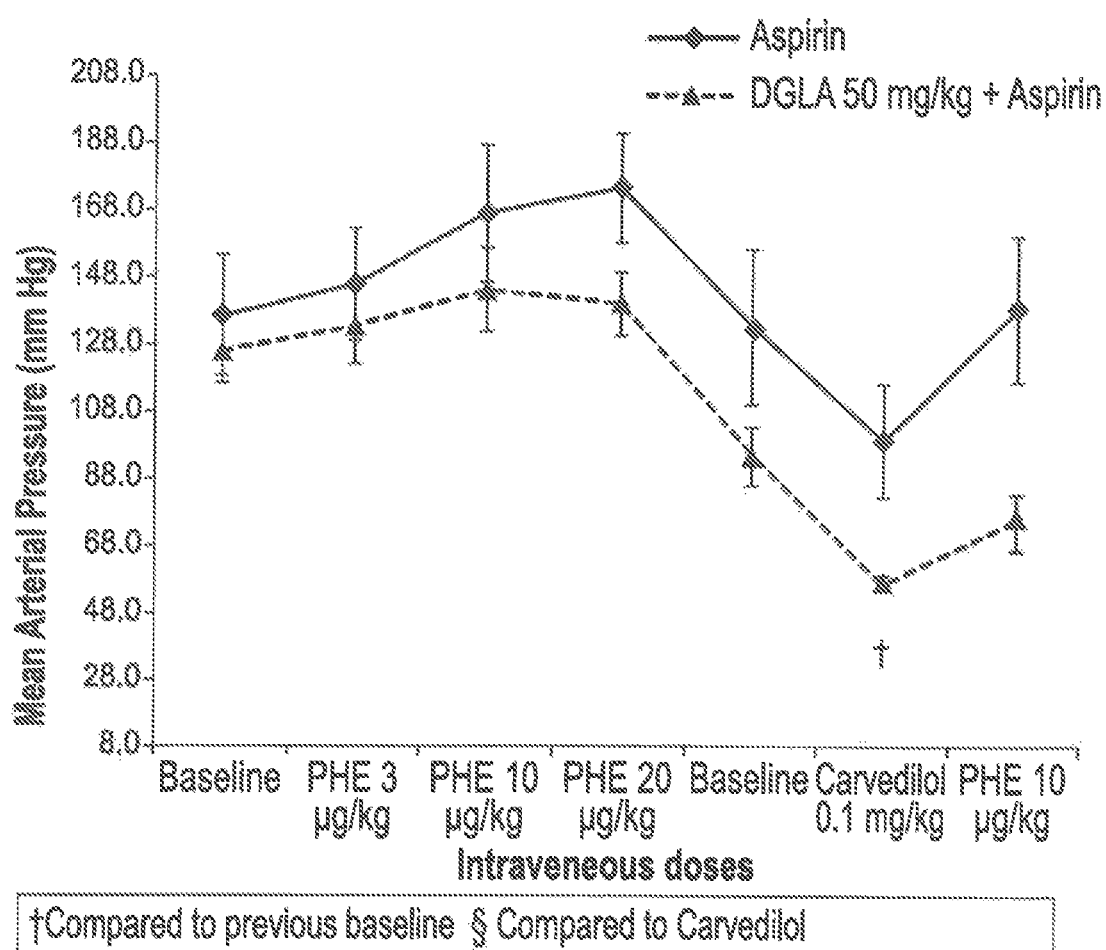
FIG. 3 shows change in mean arterial pressure (mm Hg) with intravenous doses of phenylephrine following seven consecutive days of gavage with DGLA at 500 mg/kg co-administered with Aspirin at 10 mg/kg.

FIG. 3 illustrates the changes in mean arterial pressure following intravenous doses of phenylephrine after seven consecutive days of gavage with DGLA 500 mg/kg co-administered with aspirin at 10 mg/kg in four spontaneously hypertensive rats. As with the lower dose of DGLA+ aspirin, the phenylephrine conditions were compared to those of the aspirin only group. Carvedilol was statistically compared to the baseline just before administration, while the last dose of phenylephrine (10 µg/kg) was compared to the positive control.

Despite lower mean arterial pressures observed, there was no significant statistical difference between the mean systemic arterial pressure of the rats which were fed with both DGLA and aspirin and those who were fed with aspirin only. It would thus appear that Aspirin again prevented the benefit of daily administration of 500 mg/kg DGLA. The positive control succeeded in statistically decreasing the arterial blood pressure of the animals, as observed in the other groups. The increase caused by the last dose of phenylephrine was not considered significant.

Table 13 shows mean arterial pressure at baseline following seven consecutive days with six different gavage groups.

TABLE 13

| | Mean Arterial pressure at baseline | | | | | | | | | |
|---|---|---|---|---|---|---|---|---|---|---|
| Conditions | Rat #1 | Rat #2 | Rat #3 | Rat #4 | Rat #5 | Average SAP | STED | SEM | Ttest | n |
| Vehicle | 70.64 | 77.31 | 120.52 | 93.60 | n/a | 90.5 | 22.21 | 11.10 | n/a | 4 |
| DGLA 50 mg/kg | 51.77 | 87.81 | 62.11 | 86.01 | 84.93 | 74.5 | 16.50 | 7.38 | n/a | 5 |
| DGLA 50 mg/kg + Aspirin | 136.52 | 148.19 | 176.99 | 108.14 | 77.13 | 129.4 * | 38.25 | 17.11 | 0.019 | 5 |
| DGLA 500 mg/kg | 64.81 | 91.55 | 94.41 | 66.56 | 93.64 | 82.2 | 15.12 | 6.76 | n/a | 5 |
| DGLA 500 mg/kg + Aspirin | 145.62 | 100.15 | 128.35 | 129.60 | n/a | 125.9 * | 18.90 | 9.45 | 0.006 | 4 |
| Aspirin | 86.75 | 107.64 | 160.50 | 141.36 | 187.84 | 136.8 | 40.44 | 18.09 | n/a | 5 |

Figure 4:
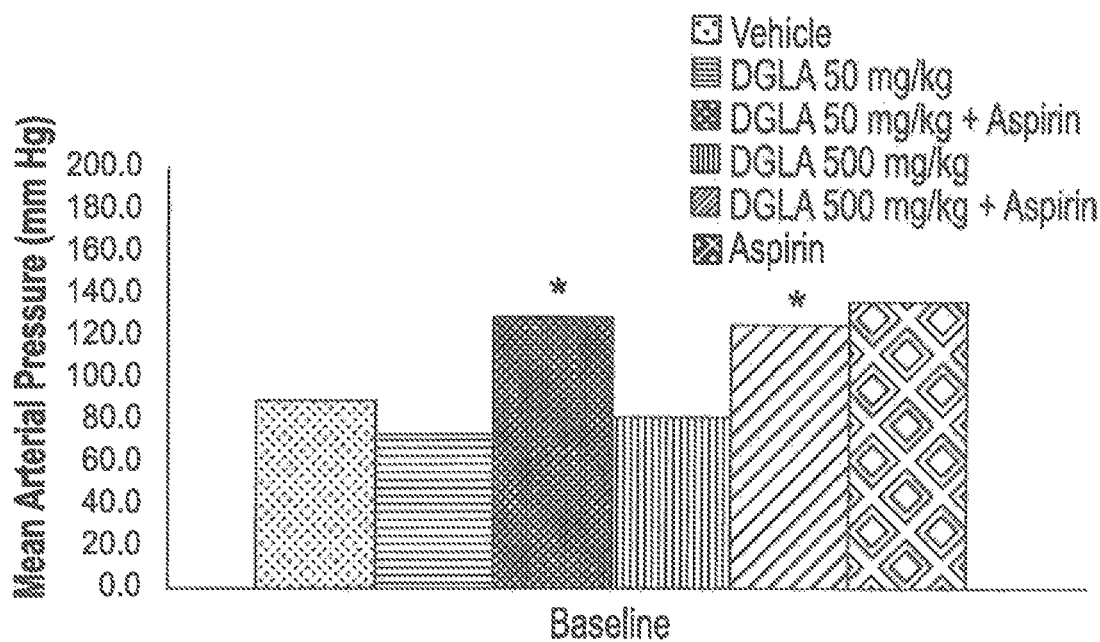
FIG. 4 shows mean arterial pressure at baseline following seven consecutive days with six different gavage groups.

FIG. 4 presents the mean arterial pressures at baseline of the six groups which were fed during the two parts of this study. The tracheotomy stabilized hemodynamics, but also caused changes in the arterial pressure of the rats. The arterial pressure of the rats who did not receive aspirin (Vehicle, DGLA 50 mg/kg and DGLA 500 mg/kg) were obtained during the first phase of this study (study #20131022-1) and those of the other groups were recorded during this present study (different batches of animals from Charles River, but same strain and size of rat). Statistical t tests were done between the groups which were administered DGLA at 50 or 500 mg/kg and their equivalent added with aspirin at 10 mg/kg. There was a statistically significant increase of the mean arterial pressure at baseline between the 50 mg/kg of DGLA alone and the 50 mg/kg of DGLA co-administered with aspirin at 10 mg/kg, as well as between the 500 mg/kg group of DGLA compared to DGLA 500 mg/kg with aspirin 10 mg/kg (significant increase marked with *).

It would thus appear that DGLA successfully decreases the arterial pressure in spontaneously hypertensive rats, an effect which is eliminated by Aspirin.

Table 14 shows mean arterial pressure with an intravenous dose of phenylephrine at 20 µk/kg following seven consecutive days with six different gavage groups.

TABLE 14

Mean Arterial pressure with an intravenous dose of Phenylephrine 20 µg/kg

| Conditions | Rat #1 | Rat #2 | Rat #3 | Rat #4 | Rat #5 | Average SAP | STED | SEM | Ttest | n |
|---|---|---|---|---|---|---|---|---|---|---|
| Vehicle | 131.99 | 130.56 | 145.47 | 137.32 | n/a | 136.3 | 6.75 | 3.37 | n/a | 4 |
| DGLA 50 mg/kg | 91.82 | 137.84 | 105.44 | 132.68 | 110.72 | 115.7 | 19.23 | 8.60 | n/a | 5 |
| DGLA 50 mg/kg + Aspirin | 196.59 | 196.00 | 196.67 | 148.23 | 141.78 | 175.9 * | 28.25 | 12.64 | 0.004 | 5 |
| DGLA 500 mg/kg | 105.21 | 119.33 | 118.12 | 97.17 | 120.82 | 112.1 | 10.43 | 4.66 | n/a | 5 |
| DGLA 500 mg/kg + Aspirin | 161.17 | 116.35 | 141.85 | 140.72 | n/a | 140.0 * | 18.36 | 9.18 | 0.023 | 4 |
| Aspirin | 149.35 | 120.84 | 202.61 | 194.76 | 203.90 | 174.3 | 37.34 | 16.70 | n/a | 5 |

Figure 5:
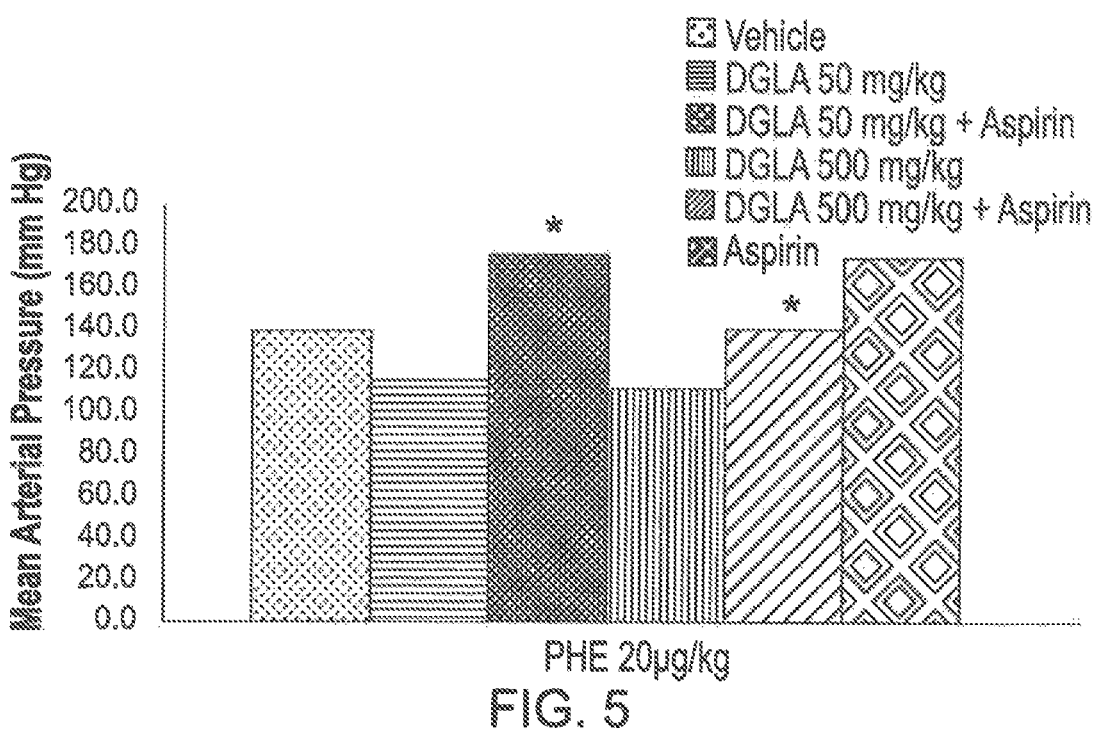
FIG. 5 shows mean arterial pressure with an intravenous dose of phenylephrine at 20 μk/kg following seven consecutive days with six different gavage groups.

FIG. 5 presents the mean arterial pressures of all the groups analyzed over the two studies investigating DGLA. These arterial pressures were obtained after an intravenous dose of phenylephrine at 20 µg/kg. As with the results acquired in baseline, each dose of DGLA was statistically compared to its equivalent condition in the aspirin only group. A significant augmentation of the mean arterial pressure was noticed between both corresponding groups (marked with *).

This study was designed to investigate the efficacy of DGLA, alone and when co-administered chronically with aspirin, to reduce the arterial pressure measured in hypertensive rats, as well as the reduction in the hypertensive response induced acutely by phenylephrine in the same strain of spontaneously hypertensive rats.

The Spontaneously Hypertensive rat (SHR) is a commonly used model in hypertension research because it produces, within each colony, uniform changes in response to direct and indirect effectors to the cardiovascular system. The rats have been selected and inbred over generations, defined as hypertensive by a systolic blood pressure of over 150 mm Hg persisting for more than one month.

The study revealed that the chronic co-administration of DGLA and aspirin prevented DGLA from lowering the mean systemic arterial blood pressure (by up to 25%) as observed previously in the spontaneous hypertensive rats treated with the DGLA.

The doses of DGLA tested (50 and 500 mg/kg) combined with aspirin at 10 mg/kg did not significantly reduce the dose-dependent elevation of the mean arterial blood pressure following phenylephrine injection, when compared to animals which were fed with aspirin alone. The two doses of DGLA caused similar effects, suggesting that the benefits of greater doses of DGLA may be minimal if Aspirin is co-administered. When both doses of DGLA were compared to their equivalent aspirin-only conditions, Aspirin caused a clear increase in the mean arterial pressure in baseline condition as well as when the rats were challenged with an intravenous dose of 20 µg/kg of phenylephrine.

In this study, Carvedilol was used as the positive control. It is a beta-blocker used to treat heart failure and high blood pressure. It acts by relaxing blood vessels and slowing heart rate, thus improving ventricular refilling, blood flow, and decreasing blood pressure. The effect of carvedilol, when injected intravenously in spontaneously hypertensive rats, confirmed its ability to decrease blood pressure after each of three doses of phenylephrine, and demonstrated the sensitivity of the test system.

Example 4

A single-center, double-blind, randomized, placebo-controlled, two part Phase one study was performed in healthy male and female subjects aged 18 to 45 years inclusive. The primary objective of this study was to assess the safety and plasma pharmacokinetics (PK) of orally administered single doses and orally administered multiple doses of DS107G capsules (once daily for 28 days) in healthy subjects.

The secondary objectives of this study were to assess the following:

The effect of food on the PK of an orally administered single dose of DS107G capsule in healthy subjects.

The PK of DGLA in human skin following multiple doses of DS107G capsule given once daily for 28 days to healthy subjects.

A total of 48 subjects were enrolled (including 32 for single dose study and 16 for multiple dose study). The single and multiple dose studies consist of 8 subjects per cohort (ideally 4 males and 4 females, but no fewer than 3 per sex).

Subjects were randomly assigned in a 3:1 ratio of DG107G to placebo by block randomization. Single dose part one of the study comprised three cohorts of eight subjects each, with the addition of Cohort four based on evaluation of the safety data of Cohort three by the Safety Monitoring Committee (SMC). A single oral dose of DS107G or matching placebo was administered to fasted subjects in Cohorts one to three (500, 1000, and 2000 mg, respectively) in parallel; subjects in Cohort four were administered a dose of 4000 mg following completion of Cohort three. Subjects in Cohort two received 1000 mg or matching placebo in the fed state at 14 days after the first dose.

Multiple dose part two of the study comprised two cohorts (Cohorts five and six) of eight subjects each, who were administered multiple doses of study drug in the fasted state for 28 days. Subjects in Cohorts five and six received DS107G 2000 or 4000 mg, respectively, or matching placebo once daily for 28 days. Cohort six was started after Cohort five safety data were evaluated by the SMC. No interim analysis was planned.

In Part one of the study, plasma PK analysis of Dihomo-Gamma-Linolenic Acid (DGLA) and 15-Hydroxyeicosatrienoic acid (15-HETrE), in fasted subjects alone, was performed for Cohorts one to four up to 312 hours post dose on study Days 1 to 5, 8, 14, and the follow-up visit. In Part two, plasma PK analysis of DGLA was performed for Cohorts five and six up to 168 hours post dose on study Days 1, 2, 3, 5, and 8. Safety assessments were monitored throughout the study.

A randomized, placebo-controlled, double blind design was used to minimize bias during the safety and tolerability assessments.

Part one of the study followed a single ascending dose design with a dose escalation to 4000 mg. With the exception of the 4000-mg dose, all of the doses in Part one of the study were previously tested in humans. Treatment-related adverse events (TEAEs) were not observed in the previously tested multiple-dose regimens such as 150 mg/day for 28 days, 450 mg/day for 28 days, 1000 mg/day for 14 days, and 2000 mg/day for 10 days. The dose selection was based on the doses of oral DGLA tested in previous clinical studies and the characterization of the PK and safety of previously tested and higher doses were observed as main objective.

The effect of food on the oral bioavailability of DGLA was also assessed.

Healthy female subjects were included in this study to assess a potential gender component on the biomarker di-hydrotestosterone as DGLA is involved in steroid metabolism.

The total duration of participation for each subject in Part one of the study was approximately 14 days, excluding the screening period. In Part 2 of the study, the duration of was approximately 42 days.

Screening procedures were conducted for both parts one and two before the start of the study on Day −1 (Baseline) by evaluating the safety assessments. Safety assessments included adverse events (AEs), clinical laboratory testing (hematology, biochemistry, virology [hepatitis B surface antigen, human immunodeficiency virus (HIV) antibodies, hepatitis C antibodies], and urine analysis), drug of abuse (DOA) test results, and pregnancy test for female subjects (urine ß human chorionic gonadotropin [ßHCG]), vital signs (blood pressure [BP], pulse, temperature), 12-lead electrocardiograms (ECGs), physical examinations, and assessment of concomitant medications (only part two of the study).

All subjects were required to have met the inclusion and exclusion criteria described below. However, minor deviations that were clinically insignificant and that posed no safety concerns had been deemed acceptable by the Investigator and the Sponsor, consistent with the protocol.

All subjects considered for study participation were required to have met the following inclusion criteria:
1. Subject was male or female.
2. Female subject and female partner of male subject:
   Must not have been pregnant (female subjects must have had a negative urine pregnancy test prior to entry into the study).
   Must not have been breast feeding.
   Must not have been planning to become pregnant during the study period or within 3 months following the study.
   Must have been adhering to an adequate form of contraception prior to entry into the study and for an additional 3 months after the follow-up visit.
3. Subject was aged between 18 and 45 years inclusive.
4. Subject had signed the informed consent form.
5. Subject's body mass index (BMI) was between 18.0 and 30.0 kg/m² inclusive.
6. Subject was considered to be in good health in the opinion of the Investigator by evaluating the safety assessments.
7. Subjects must have been able to communicate well with the Investigator, to understand and comply with the requirements of the study, and to understand and sign the written ICF. Subjects were excluded from the study if there was evidence of any of the following criteria: Subject had a clinically significant illness in the 4 weeks before screening.
8. Females of childbearing potential and female partners of male subjects who had not used a safe contraceptive measure for 3 months prior to the study and were not willing to use a safe contraceptive measure for the duration of the study; examples of a safe contraceptive measure included intra-urine device or oral contraceptives, diaphragm, or condom if used in combination with a spermicide.
9. Subject used a prescribed medication in the 2 weeks before dosing or used over-the-counter preparations (including vitamins and supplements) for 1 week before dosing (with the exception of paracetamol, which was allowed up to 48 hours before dosing), and hormonal contraceptives.
10. Subject used dietary supplements rich in omega-3 or omega-6 fatty acids.
11. Subject had a significant history of drug/solvent abuse or had positive test results at screening for DOA.
12. Subject had a history of alcohol abuse, in the opinion of the Investigator, or drank in excess of 28 units per week (males) or 21 units per week (females) at the time of screening.
13. Subject was, in the opinion of the Investigator, not suitable for participation in the study.
14. Subject had participated in another clinical study with a study drug/device within 3 months before the first day of administration of study drug.
15. Subject had a positive test result for HIV antibodies, Hepatitis B surface antigen, or Hepatitis C antibodies at screening.
16. Subject had a serious adverse reaction or significant hypersensitivity to any drug.
17. Subject had donated blood or blood products within 3 months before screening.
18. Subject had known hypersensitivity to any ingredients of the study drug.

Subjects were free to withdraw consent from the study at any time for any reason. In addition, the Investigator could withdraw a subject from study participation if, in the Investigator's opinion, it was in the best interest of the subject. A subject would be withdrawn from the study for any of the following reasons:
   Withdrawal of consent any time
   Deviations from the protocol
   Incidental illness
   An AE (adverse effect).

Although a subject was not obliged to give a reason for premature withdrawal, the Investigator was to make a reasonable effort to obtain the reason while fully respecting the subject's rights. If there was a medical reason for withdrawal of consent, the subject was to remain under the supervision of the Investigator until the subject was in satisfactory health; the Investigator was to conduct a follow-up assessment.

If the Investigator deemed it was considered in the best interest of the subject's welfare, the Investigator was to inform the subject's General Practitioner of the medical reason for the subject's withdrawal from the study. Every effort was to be made to contact a subject who failed to return to the site for any follow-up appointments in order to ensure that the subject was in satisfactory health.

In Part one of the study, subjects in Cohorts one to three were administered a single dose of study drug (either 500-, 1000-, or 2000-mg as 500-mg DS107G capsules or matching placebo capsules) in parallel on study Day 1 after at least an 8-hour fast, according to Table 15. Cohort 4 was initiated following the review of safety data from Cohort 3 by the SMC.

Food effect was evaluated in Cohort two at least 14 days after the first dose at which time a second single dose was administered. Subjects were administered a 1000-mg dose of study drug with 240 mL of water after a 10-hour fasting period and 30 minutes after starting consumption of a meal. Subjects then refrained from food intake for at least 4 hours after dosing. Food consumption was standardized for at least 12 hours after dosing using a standardized high-fat meal (800 to 1000 kcal with 500 to 600 kcal from fat and 250 kcal from carbohydrates). A typical standard test meal consisted of two eggs fried in butter, two strips of bacon, two slices of toast with butter, 120 mL of hash brown potatoes, and 240 mL of whole milk.

In Part two of the study (Cohorts five and six), subjects were administered study drug (500-mg DS107G capsules or matching placebo capsules) once daily in the fasted state for 28 days. Subjects in Cohort five received study drug first and, if they tolerated the 2000-mg daily dose for the first 14 days, subjects in Cohort six were started on the 4000-mg daily dose for 28 days.

TABLE 15

Treatment Cohorts

| Cohort | Subjects | Dose (mg) | Number of capsules | Fasted or Fed State |
|---|---|---|---|---|
| Part 1: Single Ascending Doses ||||| 
| 1 | 8 | 500-mg DGLA or placebo capsules | 1 | Fasted |
| 2 | 8 | 1000-mg DGLA or placebo capsules | 2 | Fasted |
|   | 8 | 1000-mg DGLA or placebo capsules | 2 | Fed |
| 3 | 8 | 2000-mg DGLA or placebo capsules | 4 | Fasted |
| 4 | 8 | 4000-mg DGLA or placebo capsules | 8 | Fasted |
| Part 2: Multiple Ascending Doses for 28 Consecutive Days ||||| 
| 5 | 8 | 2000-mg DGLA or placebo capsules | 4 | Fasted |
| 6 | 8 | 4000-mg DGLA or placebo capsules | 8 | Fasted |

Note:
Each DS107G capsule contained 500 mg DGLA.

Any escalation in the dose level or commencement of a subsequent cohort was decided by the Principal Investigator. A minimum of 5 subjects with evaluable safety data from Cohort three (2000-mg dose) was required before commencing Cohort four (4000-mg dose). In Part 2, a minimum of 5 subjects with 14 days of evaluable safety data from Cohort 5 (2000 mg/day) was required before commencing Cohort six (4000 mg/day).

One strength of DS107G DGLA capsule was developed containing 500 mg of DGLA free fatty acid (FFA). Capsules included the following excipients: DGLA FFA (stabilized with a nominal 2000 ppm dl-alpha tocopherol). All excipients in the capsule shell were commonly used in soft gelatin products and include a transmissible spongiform encephalopathy (TSE) certified gelatin shell containing the following ingredients: purified water, the plasticizer glycerol, the colorant titanium dioxide, and the processing aids lecithin and medium chain triglyceride. The placebo capsule (DS107G Placebo capsule) for clinical studies consisted of liquid paraffin encapsulated in a soft gelatin shell and was identical in appearance to the DGLA capsule.

Subjects meeting the eligibility criteria were randomly assigned to receive DGLA (500, 1000, 2000, 4000 mg doses) or matching placebo capsules using a randomization schedule. The randomization was block randomization with an active treatment to placebo ratio of 3:1. The randomization schedule was generated by Planimeter using SAS® 9.1.3 SP4.

Subjects were not permitted to use prescribed medication during the 2 weeks prior to dosing or to use over-the-counter preparations (including vitamins and supplements) and hormonal contraceptives for 1 week before dosing, with the exception of paracetamol, which was allowed up to 48 hours before dosing. In addition, subjects were not allowed to use dietary supplements rich in omega-3 or omega-6 fatty acids. Subjects were not permitted to consume alcohol in excess of 28 units per week (male subjects) or 21 units per week (female subjects).

Subjects were advised to avoid consuming food supplements rich in omega-3 or omega-6 fatty acids (e.g., cod liver oil capsules) for 4 weeks prior to Screening and during the study.

Subjects were advised to avoid eating poppy seeds and food containing poppy seeds for at least 24 hours before urine sample collection for testing DOA as poppy seeds can sometimes cause a positive test result.

Subjects in Cohort two undergoing evaluation of the food effect on oral 1000 mg DGLA capsules were restricted from food consumption for at least 4 hours after dosing. Food consumption was standardized for at least 12 hours post dose using a standardized high-fat meal.

Subjects were to refrain from taking any systemic or over-the-counter medication (including vitamins and supplements) during the study with the exception of hormonal contraceptives. Paracetamol (at a dose up to 4 g/day) was allowed up to 48 hours before dosing. Subjects were also to refrain from alcohol consumption from 48 hours prior to the first administration of study drug (Day 1) until the follow-up visit.

There were no restrictions on caffeine intake or tobacco use prior to or during the study.

Subjects were required to avoid exercise and strenuous physical activity for at least 3 to 4 hours before the blood was collected for the clinical laboratory test.

Analysis of plasma concentrations of DGLA (free and total) and free 15-HETrE were performed in blood samples obtained from the subjects. In addition, skin blister fluids were obtained at days 1, 7, 14, and 28 for analysis of free and total DGLA.

Plasma concentrations of dihydroxytestosterone (DHT) were assessed in Part 2 as a biomarker or exploratory efficacy endpoint.

Analysis of all plasma and skin blister fluid samples was performed using validated methods. Concentrations of free and total DGLA were measured in plasma and skin blister fluid by liquid chromatography with tandem mass spectrometry (LC/MS/MS); the quantitation range was 100 to 10,000 ng/mL for free DGLA and 5000 to 500,000 ng/mL for total DGLA. Plasma concentrations of free 15-HETrE were measured by LC/MS/MS with a quantitation range of 100 to 10,000 ng/mL. Plasma concentrations of DHT were measured by LC/MS with a quantitation range of 0.02 to 1.5 ng/mL.

Subjects were monitored throughout confinement at the Phase 1 unit for adverse reactions to the study drug and/or procedures.

The pharmacokinetic assessments used in this study were standard for evaluation of potential therapeutic agents. The safety assessments included methods that were considered to be standard for a Phase 1 clinical study.

The study was exploratory, and no formal power calculations were performed. The number of subjects planned for each cohort (8 subjects) was considered sufficient to allow assessment of the safety and systemic exposure of DS107G capsule.

Analysis of populations included the following:

The Intention-to-Treat (ITT) population consists of all randomized subjects who had been administered at least 1 dose of study drug.

The Per Protocol (PP) population consists of all subjects in the ITT population who had no major protocol violation, as defined in the SAP.

The PK population contains all subjects included in the PP population who had evaluable PK data derived from plasma. A plasma concentration observation was considered a valid, evaluable measurement if the following data were available: study identification number, randomization number, date and time of sampling, dose and concentration. A series of such measurements from the same sample were considered complete if each protocol prescribed concentration was evaluable. Plasma PK data were evaluable by definition if the data contained a complete series of observations. Any missing plasma PK observation would result in incomplete PK data, thus a subject with any missing plasma PK observation was excluded from the PK population. Subjects randomized to placebo were also excluded from the PK population.

The populations defined above were generated separately for study Part 1 and Part 2 data. Safety analysis was performed on the ITT population.

Safety analyses were performed on the safety population tabulated by treatment arm, cohort, and visit. All safety data were characterized by descriptive statistical tools. No hypothesis was set to investigate in the study protocol. Evaluation of safety assessments was performed in a descriptive manner. Continuous variables were characterized by their mean, standard deviation (SD), median, minimum and maximum values; discrete variables were characterized by their absolute (frequency) and relative (percentage [%]) distribution. Treatment groups were also Primary endpoints (PK characteristics derived from single and multiple oral doses of DS107G capsule) were derived with the help of non-compartmental PK modeling. Secondary endpoints consisted of characterizing the effect of food on the PK of a single oral dose of DS107G capsule and characterizing the PK of DGLA in human skin following multiple oral doses of DS107G capsule).

The secondary endpoints were reported using the following descriptive analytical tools: number of valid observations, mean, standard deviation (SD), median, minimum, and maximum values derived for continuous parameters grouped by treatment arm, visit and cohort.

No formal hypothesis testing was performed during evaluation of study data. In Part 1 (single ascending dose), the extent of exposure was 1 day by definition (in case of successful administration of the study drug). In Part 2 (multiple ascending doses), the extent of exposure was calculated as the day of last study drug intake minus the day of first study drug intake+1 (when no interruption in study drug administration was documented). In case of interruption(s) the result of the above formula was decreased with the number of interruption(s).

Statistical analysis of the PK data was performed using SAS Software (Version 9.1.3). No pharmacodynamics analysis was performed.

Plasma PK parameters of DGLA and of 15-HETrE were estimated using model-independent techniques (non-compartmental analysis) and included: Cmax, tmax, Clast, Tlast, AUC0-24, AUC0-inf, AUClast, λz, CL, V, and t½ for Parts 1 and 2, and tmin, cm in, CLss, Vss, Cavg, and % PTF for only Part 2 (steady-state) data.

All PK parameters were summarized descriptively, no formal statistical testing was performed due to the exploratory nature of the study.

In the single-dose setting (Part 1), study drug discontinuation was not a potential outcome in Cohorts one, three and four; therefore, no reporting activity was required for these cohorts. For Cohort 2, the enrolled subjects received study drug twice: a single dose administered in the fasted state and a second single dose administered in the fed state.

The following amendments were also made to the protocol.

Table of Clinical Studies added, to clarify previous clinical studies with oral DGLA and their safety conclusions.

Risk/benefit assessment added, to clarify the assessed risks and benefits of the proposed trial for the benefit of the Investigator and Ethics Committee.

Enrollment criteria were changed, such that subjects who were enrolled in Part 1 of the study (single-dose cohorts) could be brought back and re-enrolled in Part 2 (multiple-dose cohorts), provided they had no AEs related to study drug and they had a washout period of at least 14 days before starting the multiple-dose regimen. The rationale for this change was to aid recruitment without compromising the safety of the volunteers.

Clinical laboratory tests for coagulation (prothrombin time and activated partial prothrombin time [APTT]) were added as assessments at all clinical laboratory assessment timepoints in Part 2 of the study (multiple-dose Cohorts 5 and 6). These assessments were added to monitor any potential changes in clotting factors as an exploratory biomarker for future studies.

Ambiguous wording was replaced to clarify that single ECG recordings would be obtained.

15-HETrE was removed as an analyte for testing in Part 2 (multiple-dose cohorts), as preliminary PK data from Part 1 cohorts revealed that all samples for 15-HETrE were below the limit of quantification (BLQ).

In addition to free (unesterified) DGLA, the quantification of "total" DGLA was added to all analyses, as the plasma PK profile of the "total" may differ from the "free."

Also, changes to the planned analyses were included to provide additional analyses and statistical output.

Results

Single Dose Study.

Forty subjects were screened; of those 40, 4 subjects were excluded for not fulfilling inclusion/exclusion requirements, and 4 subjects withdrew consent. Disposition of the 32 subjects randomized to study drug is presented in Table 16.

TABLE 16

Summary of Subject Disposition - ITT population (Single Dose).

| | Dose Level of DS107G | | | | | |
|---|---|---|---|---|---|---|
| | 500 mg (N = 6) n (%) | 1000 mg (N = 6) n (%) | 2000 mg (N = 6) n (%) | 4000 mg (N = 6) n (%) | Placebo[1] (N = 8) n (%) | Overall (N = 32) n (%) |
| Total number of subjects | 6 (100) | 6 (100) | 6 (100) | 6 (100) | 8 (100) | 32 (100) |
| Randomized | 6 (100) | 6 (100) | 6 (100) | 6 (100) | 8 (100) | 32 (100) |
| Treated | 6 (100) | 6 (100) | 6 (100) | 6 (100) | 8 (100) | 32 (100) |
| Completed | 6 (100) | 6 (100) | 6 (100) | 6 (100) | 8 (100) | 32 (100) |
| Premature discontinuation | 0 | 0 | 0 | 0 | 0 | 0 |

ITT = intent-to-treat
[1]Of the 8 subjects who received placebo, 2 subjects were randomized to each of the DS107G dosing cohorts.

Plasma concentrations of free and total DGLA at baseline, before administration of DS107G, were summarized in Table 17. These concentrations were generally highly variable.

TABLE 17

Baseline Plasma Concentrations of DGLA (Single Dose, Pharmacokinetic Population)

| | | Dose Level of DS107G | | | | |
|---|---|---|---|---|---|---|
| | | 500 mg | 1000 mg | | 2000 mg | 4000 mg |
| Analyte (unit) | | Fasted (n = 5) | Fasted (n = 6) | Fed (n = 6) | Fasted (n = 6) | Fasted (n = 6) |
| Free DGLA (ng/mL) | Mean | 237.0 | 302.3 | 262.3 | 172.8 | 378.2 |
| | (SD) | (76.95) | (29.80) | (70.22) | (29.67) | (101.18) |
| | Min, Max | 150, 357 | 268, 347 | 133, 327 | 134, 204 | 241, 538 |
| Total DGLA (ng/mL) | Mean | 37740.0 | 40583.3 | 42550.0 | 33083.3 | 29900.0 |
| | (SD) | (14371.60) | (13664.47) | (16206.02) | (8247.52) | (10164.05) |
| | Min, Max | 22000, 57100 | 26700, 63900 | 28400, 66600 | 22700, 43200 | 19100, 45500 |

Figure 6:
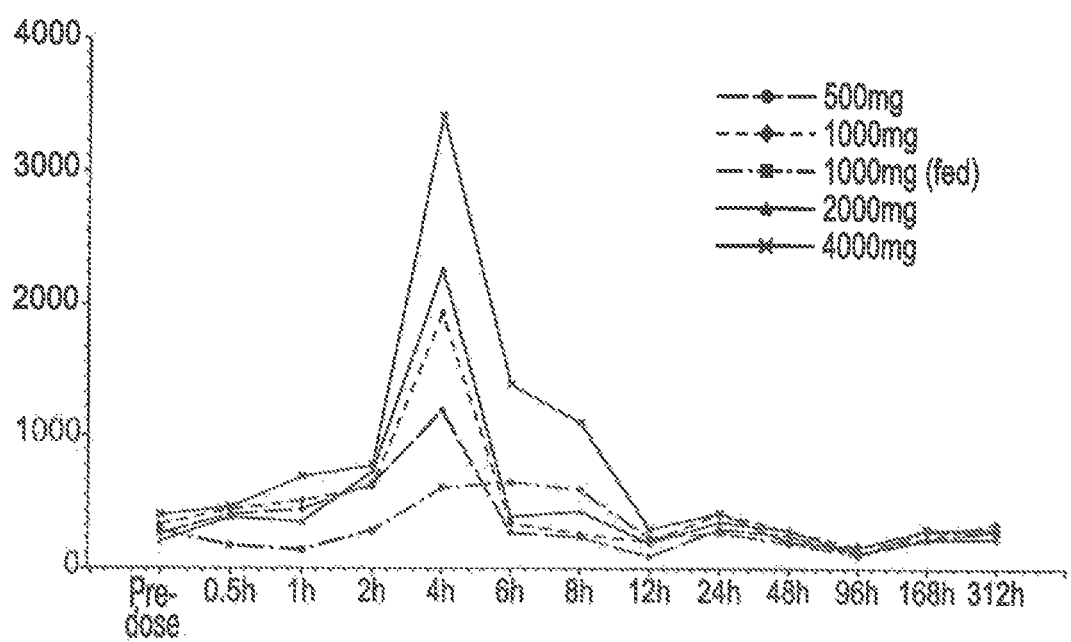
FIG. 6 shows mean plasma free DGLA concentration (ng/mL, linear plot), by dose cohort (Single Dose, PK Population).
Figure 7:
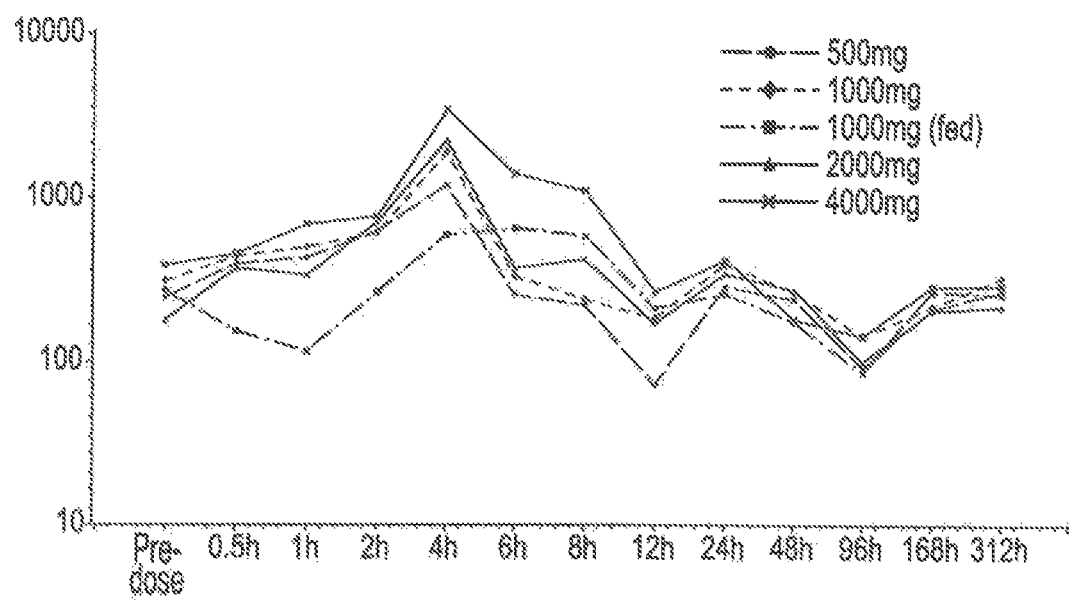
FIG. 7 shows mean plasma free DGLA concentration (ng/mL, log-linear plot), by dose cohort (Single Dose, PK Population).
Figure 8:
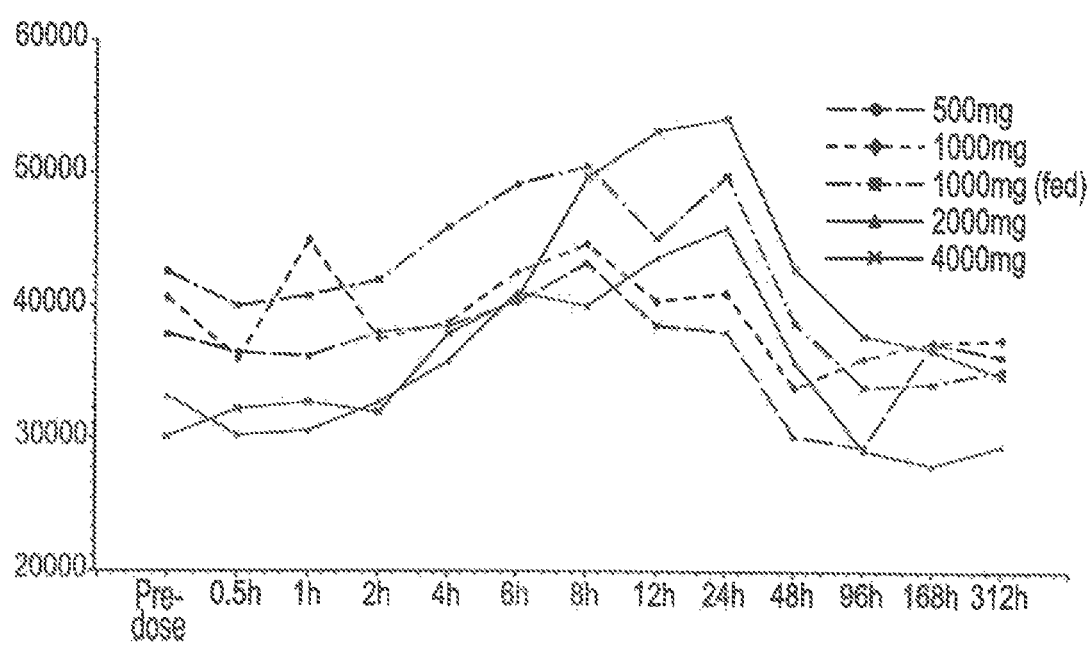
FIG. 8 shows mean plasma total DGLA concentration (ng/mL, linear plot), by dose cohort (Single Dose, PK Population).
Figure 9:
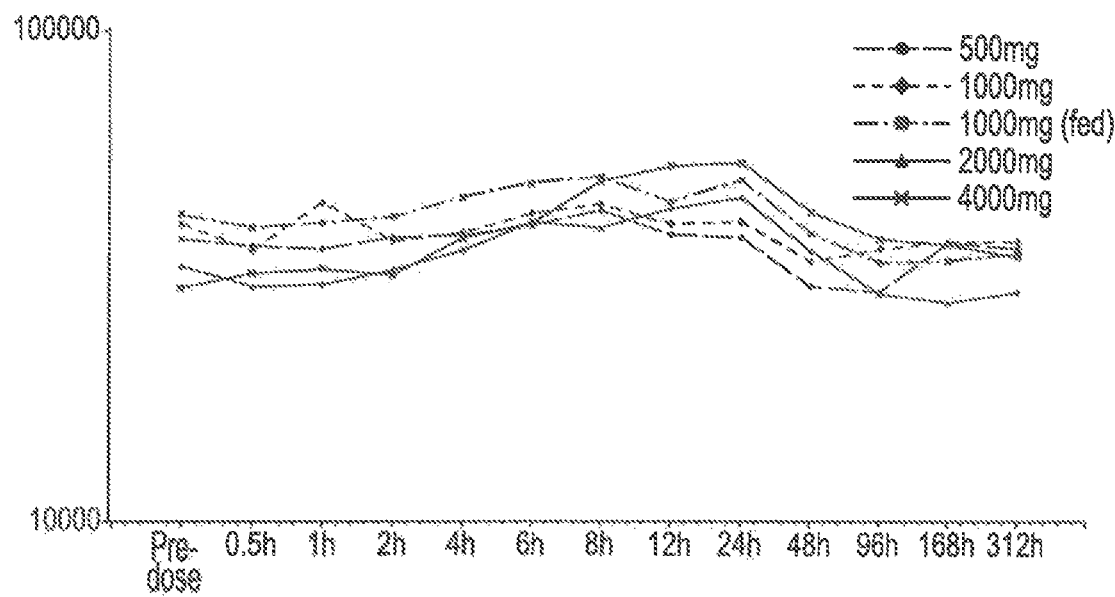
FIG. 9 shows mean plasma total DGLA concentration (ng/mL, log-linear plot), by dose cohort (Single Dose, PK Population).

DGLA = dihomo-gamma-linolenic acid;
Max = maximum;
mean = arithmetic mean;
min = minimum;
N = number of subjects providing data;
SD = standard deviation Mean plasma concentrations after a single dose of DS107G are shown graphically by dose cohort for free DGLA in FIG. 6 (linear plot) and FIG. 7 (log-linear plot), and for total DGLA in FIG. 8 (linear plot) and FIG. 9 (log-linear plot).

After a single dose of DS107G capsules (500, 1000, 2000, and 4000 mg), inter-subject variability (measured by SD) of free and total DGLA was high for both plasma concentrations and baseline-corrected PK parameters. Under fasted conditions, mean baseline-corrected $C_{max}$ and AUC0-24 for both free and total DGLA increased in a linear manner (Table 18, Table 19). The median time to maximum concentration ($T_{max}$) was 4 hour for free DGLA (Table 18) and not consistent across the dose, with values of 8 hours at the 2 lower doses and 18 hours at the 2 higher doses (Table 19). Although baseline-corrected elimination PK parameters could be determined for less than half the subjects in some cohorts, there was no evidence of nonlinear pharmacokinetics in elimination half-life or clearance for either free or total DGLA (Table 19 and Table 20). Although not evaluated statistically, administration of a single 1000-mg dose of DS107G under fasted conditions resulted in an approximately 50% higher rate and extent of total DGLA absorption based on baseline corrected mean Cmax and AUC0-24 (Table 19).

TABLE 18

Baseline-corrected Plasma Pharmacokinetic Parameters for Free DGLA after Fasted Administration (Single Dose, Pharmacokinetic Population)

| | | Dose Level of DS107G | | | |
|---|---|---|---|---|---|
| Parameter (unit) | Statistic | 500 mg (n = 5) | 1000 mg (n = 6) | 2000 mg (n = 6) | 4000 mg (n = 6) |
| $t_{max}$ (h) | N | 5 | 6 | 6 | 6 |
| | Median | 4.00 | 4.00 | 4.00 | 4.00 |
| | Min, Max | 4.0, 4.0 | 4.0, 4.0 | 4.0, 8.0 | 4.0, 6.0 |

TABLE 18-continued

Baseline-corrected Plasma Pharmacokinetic Parameters for Free DGLA after Fasted Administration (Single Dose, Pharmacokinetic Population)

| Parameter (unit) | Statistic | Dose Level of DS107G | | | |
|---|---|---|---|---|---|
| | | 500 mg (n = 5) | 1000 mg (n = 6) | 2000 mg (n = 6) | 4000 mg (n = 6) |
| $C_{max}$ (ng/mL) | N | 5 | 6 | 6 | 6 |
| | Mean | 934.6 | 1602.8 | 2074.0 | 3021.8 |
| | SD | 776.87 | 1202.43 | 1276.03 | 1581.97 |
| $C_{max}$/Dose (1/kL) | N | 5 | 6 | 6 | 6 |
| | Mean | 1.869 | 1.603 | 1.037 | 0.755 |
| | SD | 1.5537 | 1.2024 | 0.6380 | 0.3955 |
| $AUC_{0-24}$ (ng·h/mL) | N | 5 | 6 | 6 | 6 |
| | Mean | 2728.1 | 3998.5 | 6429.0 | 9436.8 |
| | SD | 2253.49 | 1885.27 | 2119.39 | 2227.25 |
| $AUC_{0-24}$/Dose (h/kL) | N | 5 | 6 | 6 | 6 |
| | Mean | 5.46 | 4.00 | 3.21 | 2.36 |
| | SD | 4.507 | 1.885 | 1.060 | 0.557 |
| $\lambda_z$ (1/h) | N | 2 | 5 | 5 | 5 |
| | Mean | 0.0035 | 0.0487 | 0.0200 | 0.0603 |
| | SD | 0.00101 | 0.05133 | 0.02445 | 0.10642 |
| $t_{1/2}$ (h) | N | 2 | 5 | 5 | 5 |
| | Median | 206.33 | 28.30 | 57.33 | 67.53 |
| | Min, Max | 164.3, 248.4 | 6.2, 3226.3 | 11.0, 181.1 | 2.8, 80.9 |
| $AUC_{0-inf}$ (ng·h/mL) | N | 2 | 5 | 5 | 5 |
| | Mean | 21483.3 | 218955.6 | 26877.0 | 17113.6 |
| | SD | 14902.37 | 474291.75 | 19394.67 | 3545.72 |
| $AUC_{0-inf}$/Dose (h/kL) | N | 2 | 5 | 5 | 5 |
| | Mean | 42.97 | 218.96 | 13.44 | 4.28 |
| | SD | 29.805 | 474.292 | 9.697 | 0.886 |
| CL/F (kL/h) | N | 2 | 5 | 5 | 5 |
| | Mean | 0.0306 | 0.1866 | 0.1339 | 0.2420 |
| | SD | 0.02126 | 0.18154 | 0.11952 | 0.05066 |
| Vz/F (kL) | N | 2 | 5 | 5 | 5 |
| | Mean | 10.035 | 7.356 | 8.977 | 17.460 |
| | SD | 8.9574 | 9.1148 | 4.0610 | 11.5516 |

Max = maximum;
mean = arithmetic mean;
min = minimum;
N = number of subjects providing data;
SD = standard deviation
Note:
Predose DGLA concentration was subtracted from subsequent concentrations before parameter calculation; negative values were replaced by zero.

TABLE 19

Baseline-corrected Plasma Pharmacokinetic Parameters for Total DGLA after Fasted Administration (Single Dose, Pharmacokinetic Population)

| Parameter (unit) | Statistic | Dose Level of DS107G | | | |
|---|---|---|---|---|---|
| | | 500 mg (n = 5) | 1000 mg (n = 6) | 2000 mg (n = 6) | 4000 mg (n = 6) |
| $t_{max}$ (h) | N | 5 | 6 | 6 | 6 |
| | Median | 8.00 | 8.00 | 18.00 | 18.00 |
| | Min, Max | 6.0, 312.0 | 0.0, 312.0 | 6.0, 24.0 | 8.0, 24.0 |
| $C_{max}$ (ng/mL) | N | 5 | 6 | 6 | 6 |
| | Mean | 7200.0 | 15750.0 | 17733.3 | 25883.3 |
| | SD | 2801.79 | 16326.02 | 9867.66 | 13658.32 |
| $C_{max}$/Dose (1/kL) | N | 5 | 6 | 6 | 6 |
| | Mean | 14.400 | 15.750 | 8.867 | 6.471 |
| | SD | 5.6036 | 16.3260 | 4.9338 | 3.4146 |
| $AUC_{0-24}$ (ng·h/mL) | N | 5 | 4 | 6 | 6 |
| | Mean | 39556.6 | 215369.7 | 210508.9 | 437754.0 |
| | SD | 37969.05 | 346249.37 | 167660.31 | 278838.30 |
| $AUC_{0-24}$/Dose (h/kL) | N | 5 | 4 | 6 | 6 |
| | Mean | 79.11 | 215.37 | 105.25 | 109.44 |
| | SD | 75.938 | 346.249 | 83.830 | 69.710 |
| $\lambda_z$ (1/h) | N | 2 | 2 | 2 | 5 |
| | Mean | 0.0013 | 0.0136 | 0.0084 | 0.0102 |
| | SD | 0.00042 | 0.01381 | 0.00301 | 0.00993 |

TABLE 19-continued

Baseline-corrected Plasma Pharmacokinetic Parameters for Total DGLA
after Fasted Administration (Single Dose, Pharmacokinetic Population)

| Parameter (unit) | | Dose Level of DS107G | | | |
|---|---|---|---|---|---|
| | | 500 mg (n = 5) | 1000 mg (n = 6) | 2000 mg (n = 6) | 4000 mg (n = 6) |
| $t_{1/2}$ (h) | N | 2 | 2 | 2 | 5 |
| | Median | 552.07 | 105.42 | 88.04 | 71.03 |
| | Min, Max | 428.3, 675.9 | 29.7, 181.2 | 65.8, 110.3 | 26.7, 464.7 |
| $AUC_{0-inf}$ (ng · h/mL) | N | 2 | 2 | 2 | 5 |
| | Mean | 4415966.6 | 4031410.9 | 2276495.1 | 5973518.8 |
| | SD | 723917.02 | 5304874.41 | 1948487.62 | 7261476.90 |
| $AUC_{0-inf}$/Dose (h/kL) | N | 2 | 2 | 2 | 5 |
| | Mean | 8831.93 | 4031.41 | 1138.25 | 1493.38 |
| | SD | 1447.834 | 5304.874 | 974.244 | 1815.369 |
| CL/F (kL/h) | N | 2 | 2 | 2 | 5 |
| | Mean | 0.0001 | 0.0018 | 0.0014 | 0.0036 |
| | SD | 0.00002 | 0.00243 | 0.00119 | 0.00519 |
| Vz/F (kL) | N | 2 | 2 | 2 | 5 |
| | Mean | 0.089 | 0.093 | 0.203 | 0.275 |
| | SD | 0.0140 | 0.0843 | 0.2136 | 0.1569 |

Max = maximum;
mean = arithmetic mean;
min = minimum;
N = number of subjects providing data;
SD = standard deviation
Note:
Predose DGLA concentration was subtracted from subsequent concentrations before parameter calculation; negative values were replaced by zero.

The effect of food on the single-dose baseline-corrected PK of free and total DGLA using the 1000-mg dose (Cohort two) was evaluated and reported in Table 21. Briefly, the mean baseline-corrected free DGLA Cmax was about 3 fold higher and occurred 1 hour (median) sooner under fasted conditions than under fed conditions (Table 21). Mean free DGLA baseline-corrected AUC0-24 under fasted conditions was about 2 fold higher than the value under fed conditions. Thus an increased rate and extent of DGLA absorption under fasted conditions was observed. There were no clear differences for fasted vs fed conditions in elimination of free DGLA (Table 20).

For total DGLA, mean baseline-corrected Cmax was about 1.5-fold higher and tmax occurred about 50% sooner (median, 8 vs 15 h) under fasted conditions than under fed conditions (Table 20). Mean baseline-corrected AUC0-24 under fasted conditions was about 1.8-fold higher than under fed conditions. Just under half of the subjects (⅔ fasted, ⅜ fed) had sufficient data to estimate total DGLA λz, t½, clearance, and volume of distribution. These data suggest an increased rate and extend of total DGLA absorption under fasted condition. No reliable conclusion regarding total DGLA elimination or volume distribution due to small data population.

Based on the PK parameters shown in Table 20, mean baseline-corrected Cmax was ~10 fold (fasted) and ~20-fold (fed) higher for total DGLA than for free DGLA. Mean baseline-corrected AUC0-24 was ~54-fold (fasted) and ~56-fold (fed) higher for total DGLA than for free DGLA.

TABLE 20

Baseline-corrected Plasma Pharmacokinetic Parameters for DGLA, After Fasted
vs Fed Administration (Single Dose, Pharmacokinetic Population)

| Parameter (unit) | Statistic | 1000 mg DS107G | | | |
|---|---|---|---|---|---|
| | | Free DGLA | | Total DGLA | |
| | | Fasted (n = 6) | Fed (n = 6) | Fasted (n = 6) | Fed (n = 6) |
| $t_{max}$ (h) | N | 6 | 6 | 6 | 6 |
| | Median | 4.00 | 5.00 | 8.00 | 15.00 |
| | Min, Max | 4.0, 4.0 | 4.0, 8.0 | 0.0, 312.0 | 6.0, 24.0 |
| $C_{max}$ (ng/mL) | N | 6 | 6 | 6 | 6 |
| | Mean | 1602.8 | 520.2 | 15750.0 | 10316.7 |
| | SD | 1202.43 | 235.54 | 16326.02 | 2043.93 |
| $C_{max}$/Dose (1/kL) | N | 6 | 6 | 6 | 6 |
| | Mean | 1.603 | 0.520 | 15.750 | 10.317 |
| | SD | 1.2024 | 0.2355 | 16.3260 | 2.0439 |
| $AUC_{0-24}$ (ng · h/mL) | N | 6 | 6 | 4 | 6 |
| | Mean | 3998.5 | 2102.7 | 215369.7 | 117389.7 |
| | SD | 1885.27 | 1174.23 | 346249.37 | 70263.85 |
| $AUC_{0-24}$/Dose (h/kL) | N | 6 | 6 | 4 | 6 |
| | Mean | 4.00 | 2.10 | 215.37 | 117.39 |
| | SD | 1.885 | 1.174 | 346.249 | 70.264 |

TABLE 20-continued

Baseline-corrected Plasma Pharmacokinetic Parameters for DGLA, After Fasted
vs Fed Administration (Single Dose, Pharmacokinetic Population)

| | | 1000 mg DS107G | | | |
|---|---|---|---|---|---|
| | | Free DGLA | | Total DGLA | |
| Parameter (unit) | Statistic | Fasted (n = 6) | Fed (n = 6) | Fasted (n = 6) | Fed (n = 6) |
| $\lambda_z$ (1/h) | N | 5 | 3 | 2 | 3 |
| | Mean | 0.0487 | 0.0403 | 0.0136 | 0.0805 |
| | SD | 0.05133 | 0.06154 | 0.01381 | 0.06155 |
| $t_{1/2}$ (h) | N | 5 | 3 | 2 | 3 |
| | Median | 28.30 | 140.86 | 105.42 | 6.62 |
| | Min, Max | 6.2, 3226.3 | 6.2, 149.4 | 29.7, 181.2 | 5.5, 66.0 |
| $AUC_{0-inf}$ (ng · h/mL) | N | 5 | 3 | 2 | 3 |
| | Mean | 218955.6 | 29150.8 | 4031410.9 | 267053.2 |
| | SD | 474291.75 | 23323.42 | 5304874.41 | 335666.87 |
| $AUC_{0-inf}$/Dose (h/kL) | N | 5 | 3 | 2 | 3 |
| | Mean | 218.96 | 29.15 | 4031.41 | 267.05 |
| | SD | 474.292 | 23.323 | 5304.874 | 335.667 |
| CL/F (kL/h) | N | 5 | 3 | 2 | 3 |
| | Mean | 0.1866 | 0.1658 | 0.0018 | 0.0096 |
| | SD | 0.18154 | 0.24651 | 0.00243 | 0.00702 |
| Vz/F (kL) | N | 5 | 3 | 2 | 3 |
| | Mean | 7.356 | 4.623 | 0.093 | 0.128 |
| | SD | 9.1148 | 0.5166 | 0.0843 | 0.0209 |

Max = maximum;
mean = aritnmetic mean;
min = minimum;
N = number of subjects providing data;
SD = standard deviation
Note:
Predose DGLA concentration was subtracted from subsequent concentrations before parameter calculation; negative values were replaced by zero.

DS107G was well tolerated as single dose at amounts 500, 1000, 2000, or 4000 mg to healthy volunteers. The most common TEAE reported were mild to moderate diarrhea (reported term: loose stool), by a similar percentage of subjects between the active-treatment and placebo-control subjects (incidence: 5/24 [20.8%] active-treated subjects vs 2/8 [25.0%] placebo-control subjects). The diarrhea events were of relatively short duration, and all (including those occurring in placebo-control subjects) were considered by the Investigator to be possibly related to study drug. Of note, subjects who received a second single dose of DS107G and who had TEAEs of diarrhea in the fasted state did not have a recurrence of diarrhea All other TEAEs occurred in only 1 subject each and only in the active-treatment groups, including: mild infection, oropharyngeal pain, and pharyngitis; and moderately severe pyrexia and urinary tract infection after dosing in the fed state.

Multiple-Dose Results—Study Part 2

Figure 10:
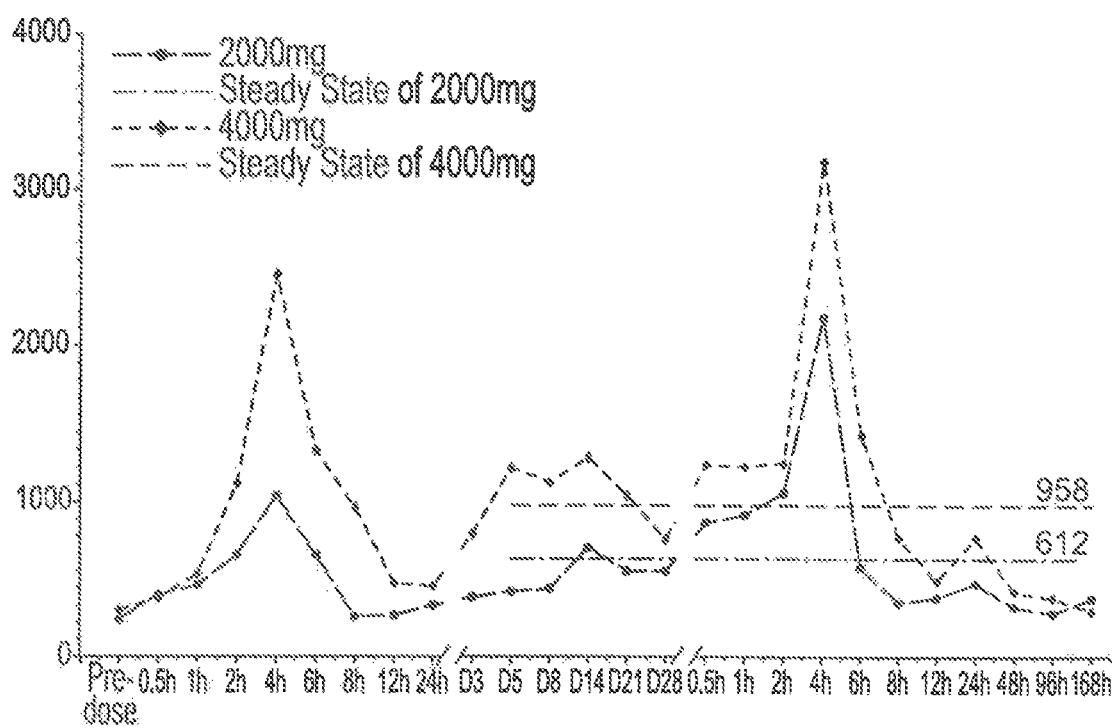
FIG. 10 shows mean plasma free DGLA concentration (ng/mL, linear plot), by dose cohort (Multiple-dose, PK Population).
Figure 11:
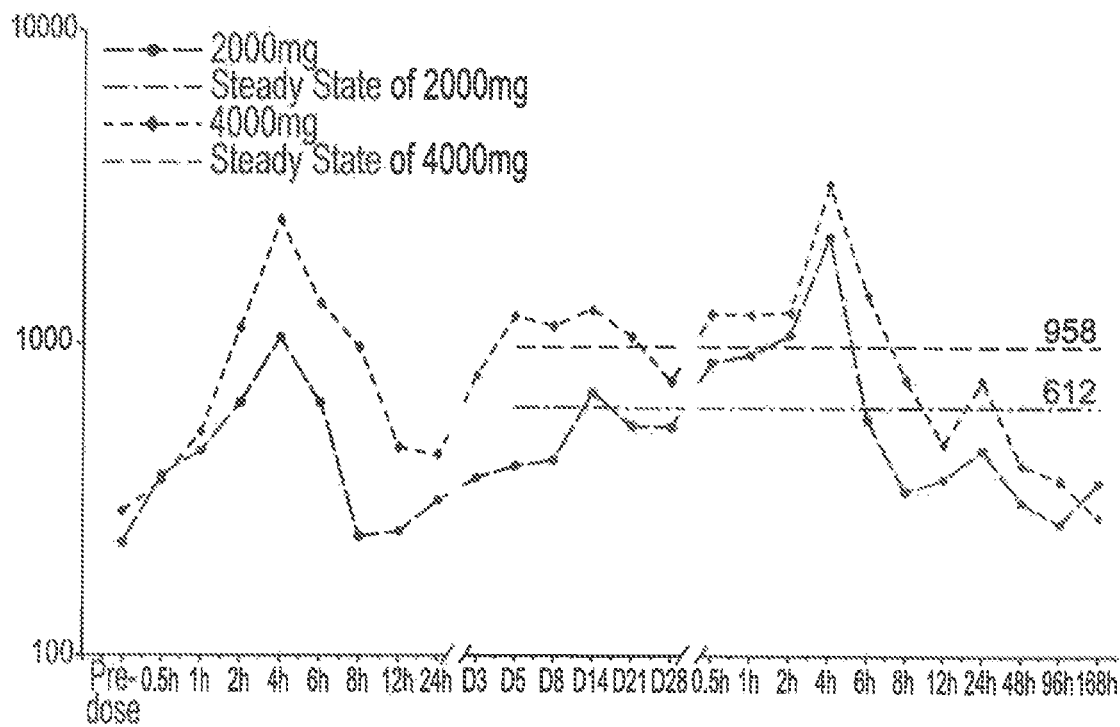
FIG. 11 shows mean plasma free DGLA Concentration (ng/mL, log-linear plot), by dose cohort (Multiple-dose, PK Population).
Figure 12:
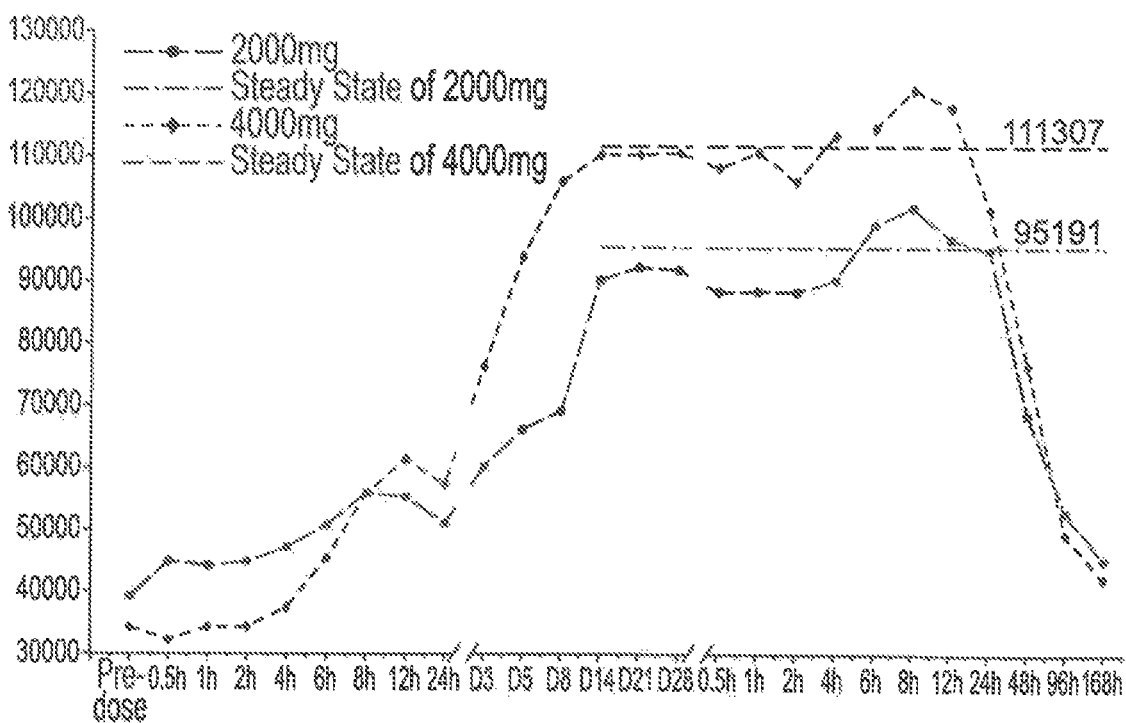
FIG. 12 shows mean plasma total DGLA concentration (ng/mL, linear plot), by dose cohort (Multiple-dose, PK Population).
Figure 13:
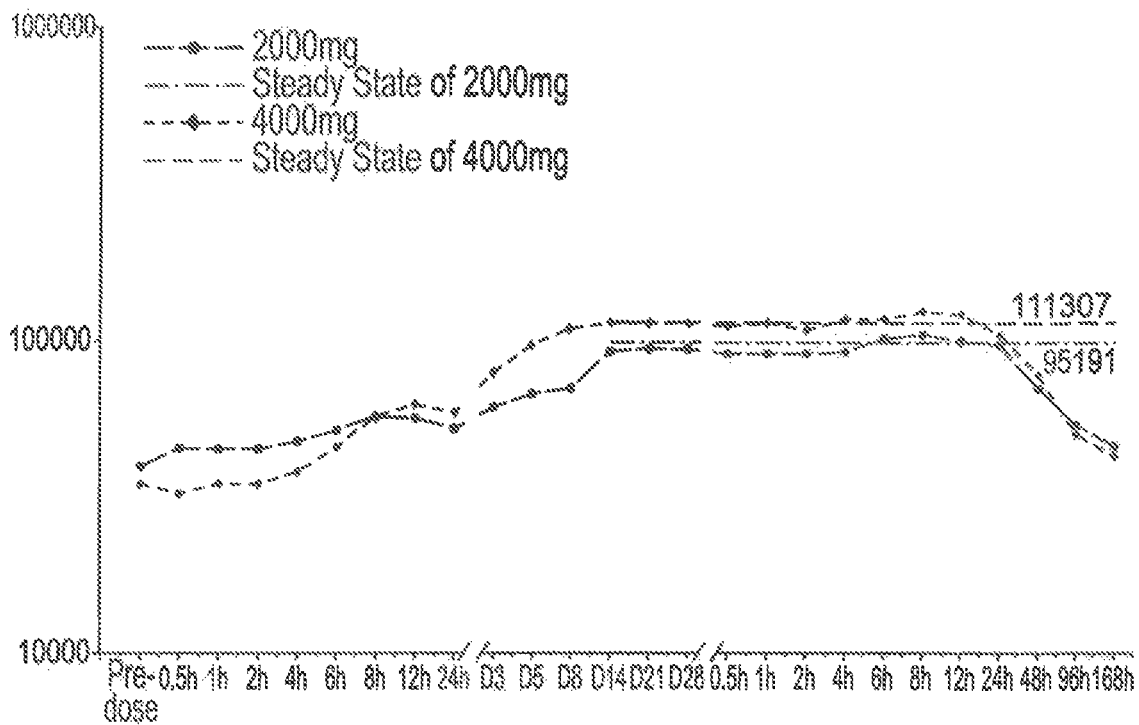
FIG. 13 shows mean plasma total DGLA concentration (ng/mL, log-linear plot), by dose cohort (Multiple-dose, PK Population).

Mean plasma concentrations and the average concentration at steady-state for Part 2 are shown graphically by dose cohort for free DGLA in FIG. 10 (linear plot) and FIG. 11 (log-linear plot), and for total DGLA in FIG. 12 (linear plot) and FIG. 13 (log-linear plot). On Days 1 and 28, mean concentrations of free DGLA peaked at about 4 hours after dosing, whereas no mean peak concentration was evident for total DGLA. Mean concentrations of both free and total DGLA increased over time with repeated dosing, though the increase for total DGLA was more pronounced. Plasma concentrations appeared to reach steady-state by around Day 14 for both doses (2000 and 4000 mg daily) and analytes (free and total DGLA) based on visual inspection of the mean concentration plots. When the dose doubled from 2000 to 4000 mg daily, the average concentration at steady state increased 1.6-fold for free DGLA but only 1.2-fold for total DGLA, suggesting one or more saturable processes at the higher dose.

PK parameter was computed after correcting the dosed DGLA concentrations with baseline DGLA concentrations.

The plasma baseline corrected pharmacokinetics for free DGLA is reported in Table 21. Briefly, mean free DGLA baseline-corrected $C_{max}$ and AUC were higher in the higher DS107G dose cohort on both days evaluated. Mean baseline-corrected $C_{max}$ for the 4000 mg dose was ~3-fold higher than for the 2000 mg dose on Day 1 but only ~1.4 fold higher on Day 28. Mean baseline-corrected AUC0-24 for the 4000 mg dose was ~2.5 fold higher than for the 2000 mg dose on Day 1 and only ~1.7-fold higher on Day 28. The changes with dose were linear for baseline-corrected $C_{max}$ and AUC0-24 on Day 1, but only for baseline-corrected AUC0-24 on Day 28. High inter-subject variability might have caused this inconsistency. Median $t_{max}$ was similar for both dose cohorts on Day 1 and Day 28, with values of 4 or 5 hours. Median elimination t½ was longer on Day 28 than on Day 1, with the value on Day 28 dependent on the time interval evaluated. Mean clearance decreased and mean volume of distribution increased with multiple doses.

TABLE 21

Plasma Baseline-corrected Pharmacokinetic Parameters for Free DGLA (Multiple-dose, Pharmacokinetic Population)

| Parameter (unit) | Statistic | Day 1 0 to 24 hours 2000 mg (n = 6) | Day 1 0 to 24 hours 4000 mg (n = 6) | Day 28 0 to 24 hours 2000 mg (n = 6) | Day 28 0 to 24 hours 4000 mg (n = 6) | Day 28 0 to 168 hours 2000 mg (n = 6) | Day 28 0 to 168 hours 4000 mg (n = 6) |
|---|---|---|---|---|---|---|---|
| $t_{max}$ (h) | N | 6 | 6 | 6 | 6 | 6 | 6 |
| | Median | 4.00 | 5.00 | 4.00 | 4.00 | 4.00 | 4.00 |
| | Min, Max | 4.0, 6.0 | 2.0, 8.0 | 2.0, 4.0 | 4.0, 4.0 | 2.0, 4.0 | 4.0, 4.0 |
| $C_{max}$ (ng/mL) | N | 6 | 6 | 6 | 6 | 6 | 6 |
| | Mean | 850.5 | 2641.5 | 1999.3 | 2873.2 | 1999.3 | 2873.2 |
| | SD | 458.84 | 1734.46 | 1003.19 | 1246.97 | 1003.19 | 1246.97 |
| $C_{max}$/Dose (1/kL) | N | 6 | 6 | 6 | 6 | 6 | 6 |
| | Mean | 0.425 | 0.660 | 1.000 | 0.718 | 1.000 | 0.718 |
| | SD | 0.2294 | 0.4336 | 0.5016 | 0.3117 | 0.5016 | 0.3117 |
| $AUC_{0-24}$ (ng·h/mL) | N | 6 | 6 | 6 | 6 | 6 | 6 |
| | Mean | 4548.7 | 11441.4 | 9248.1 | 16155.2 | 9248.1 | 16155.2 |
| | SD | 3330.51 | 5313.29 | 2559.31 | 6367.97 | 2559.31 | 6367.97 |
| $AUC_{0-24}$/Dose (h/kL) | N | 6 | 6 | 6 | 6 | 6 | 6 |
| | Mean | 2.27 | 2.86 | 4.62 | 4.04 | 4.62 | 4.04 |
| | SD | 1.665 | 1.328 | 1.280 | 1.592 | 1.280 | 1.592 |
| $\lambda_z$ (1/h) | N | 2 | 6 | 3 | 5 | 5 | 6 |
| | Mean | 0.2133 | 0.1504 | 0.1282 | 0.0596 | 0.0250 | 0.0404 |
| | SD | 0.16812 | 0.10843 | 0.15619 | 0.02019 | 0.02983 | 0.05960 |
| $t_{1/2}$ (h) | N | 2 | 6 | 3 | 5 | 5 | 6 |
| | Median | 4.71 | 5.92 | 14.04 | 12.72 | 63.59 | 48.18 |
| | Min, Max | 2.1, 7.3 | 2.0, 18.3 | 2.2, 25.6 | 7.5, 16.5 | 9.0, 132.1 | 4.3, 65.7 |
| $AUC_{0-inf}$ (ng·h/mL) | N | 2 | 6 | 3 | 5 | 5 | 6 |
| | Mean | 5955.6 | 13900.3 | 10389.0 | 22926.3 | 43024.8 | 43184.3 |
| | SD | 5216.07 | 4993.97 | 2677.43 | 6485.37 | 35641.74 | 21443.83 |
| $AUC_{0-inf}$/Dose (h/kL) | N | 2 | 6 | 3 | 5 | 5 | 6 |
| | Mean | 2.98 | 3.48 | 5.19 | 5.73 | 21.51 | 10.80 |
| | SD | 2.608 | 1.248 | 1.339 | 1.621 | 17.821 | 5.361 |
| CL/F (kL/h) | N | 2 | 6 | 3 | 5 | 5 | 6 |
| | Mean | 0.5448 | 0.3325 | 0.2002 | 0.1865 | 0.0949 | 0.1266 |
| | SD | 0.47711 | 0.16310 | 0.04493 | 0.05432 | 0.08636 | 0.08671 |
| Vz/F (kL) | N | 2 | 6 | 3 | 5 | 5 | 6 |
| | Mean | 2.426 | 3.063 | 3.592 | 3.493 | 4.470 | 5.273 |
| | SD | 0.3245 | 1.9716 | 2.5139 | 1.5255 | 1.5179 | 2.1568 |

Max = maximum;

mean = arithmetic mean;

min = minimum;

N = number of subjects providing data;

SD = standard deviation

Note:

Predose DGLA concentration was subtracted from subsequent concentrations before parameter calculation; negative values were replaced by zero.

The steady state plasma baseline corrected pharmacokinetics for free DGLA is reported in Table 22. Briefly, the plasma concentrations of free and total DGLA increased with repeated dosing, and achieved steady-state at approximately Day 14. When at steady state, evaluated on Day 28 (0-24 hours), Peak Trough Fluctuation (PTF) was quite high for both dose cohorts (mean, ~430% and ~490%; Table 9).

The mean accumulation ratio (AR) was greater for the 2000 mg than the 4000 mg dose cohort for both $C_{max}$ and AUC (ARs of ~2.8 and ~3.3 for 2000 mg vs ~1.4 and ~1.6 for 4000 mg. The data suggest saturable kinetics and/or presence of change in the distribution volume with repeated dosing of free DGLA.

TABLE 22

Steady-state Plasma Baseline-corrected Pharmacokinetic Parameters for Free DGLA (Multiple-dose, Pharmacokinetic Population)

| Parameter (unit) | | Day 28: 0 to 24 hours Dose Level of DS107G | |
|---|---|---|---|
| | | 2000 mg (n = 6) | 4000 mg (n = 6) |
| $t_{min}$ (h) | N | 6 | 6 |
| | Median | 8.00 | 8.00 |
| | Min, Max | 6.0, 24.0 | 0.0, 12.0 |
| $C_{min}$ (ng/mL) | N | 6 | 6 |
| | Mean | 100.8 | 147.0 |
| | SD | 103.34 | 230.37 |
| $CL_{ss}/F$ (kL/h) | N | 6 | 6 |
| | Mean | 0.2295 | 0.2858 |
| | SD | 0.05874 | 0.12493 |
| $Vz_{ss}/F$ (kL) | N | 3 | 5 |
| | Mean | 5.3096 | 5.7563 |
| | SD | 4.02532 | 3.12495 |
| $C_{avg}$ (ng/mL) | N | 6 | 6 |
| | Mean | 385.3 | 673.1 |
| | SD | 106.64 | 265.33 |
| % PTF (%) | N | 6 | 6 |
| | Mean | 492.54 | 431.97 |
| | SD | 212.957 | 207.312 |
| $AR(C_{max})$ | N | 6 | 6 |
| | Mean | 2.796 | 1.385 |
| | SD | 1.7385 | 0.7726 |
| AR(AUC) | N | 6 | 6 |
| | Mean | 3.340 | 1.561 |
| | SD | 2.4958 | 0.6377 |

AR = accumulation ratio;
Max = maximum;
mean = arithmetic mean;
min = minimum;
N = number of subjects providing data;
PTF = peak trough fluctuation;
SD = standard deviation
Note:
Predose DGLA concentration was subtracted from subsequent concentrations before parameter calculation; negative values were replaced by zero.

The plasma baseline corrected pharmacokinetics for total DGLA is reported in Table 23. Briefly, mean total DGLA baseline-corrected $C_{max}$ and AUC0-24 were higher in the higher DS107G dose cohort on both days evaluated, as expected. Mean baseline-corrected $C_{max}$ and AUC0-24 for the 4000 mg dose were ~1.5- and ~1.5-fold higher, respectively, than for the 2000 mg dose on Day 1 but only ~1.2- and ~1.4-fold higher than for the 2000 mg dose on Day 28.

The changes with dose in baseline-corrected $C_{max}$ and AUC4 were not linear for total DGLA on either day evaluated. High inter-subject variability might have caused this inconsistency. Median T occurred sooner with multiple doses (8-10 h) than with a single dose (10 18 h) in both dose cohorts. Median total DGLA elimination t½ for the 2000 mg dose cohort was 34.4 to 44.0 hours when assessed over 24 hours (Days 1 and 28, respectively), and 62.6 hours on Day 28 when evaluated over 0 to 168 hours. Mean clearance and volume of distribution decreased with multiple doses.

TABLE 23

Plasma Baseline-corrected Pharmacokinetic Parameters for Total DGLA (Multiple-dose, Pharmacokinetic Population)

| Parameter (unit) | Statistic | Day 1 0 to 24 hours | | Day 28 0 to 24 hours | | Day 28 0 to 168 hours | |
|---|---|---|---|---|---|---|---|
| | | 2000 mg (n = 6) | 4000 mg (n = 6) | 2000 mg (n = 6) | 4000 mg (n = 6) | 2000 mg (n = 6) | 4000 mg (n = 6) |
| $t_{max}$ (h) | N | 6 | 6 | 6 | 6 | 6 | 6 |
| | Median | 10.00 | 18.00 | 8.00 | 10.00 | 8.00 | 10.0 |
| | Min, Max | 8.0, 12.0 | 12.0, 24.0 | 6.0, 24.0 | 8.0, 24.0 | 6.0, 24.0 | 8.0, 24.0 |
| $C_{max}$ (ng/mL) | N | 6 | 6 | 6 | 6 | 6 | 6 |
| | Mean | 18100.0 | 27866.7 | 75583.3 | 90866.7 | 75583.3 | 90866.7 |
| | SD | 15113.44 | 10391.66 | 30385.55 | 33000.16 | 30385.55 | 33000.16 |
| $C_{max}$/Dose (1/kL) | N | 6 | 6 | 6 | 6 | 6 | 6 |
| | Mean | 9.050 | 6.967 | 37.792 | 22.717 | 37.792 | 22.717 |
| | SD | 7.5567 | 2.5979 | 15.1928 | 8.2500 | 15.1928 | 8.2500 |
| $AUC_{0-24}$ (ng · h/mL) | N | 6 | 6 | 6 | 6 | 6 | 6 |
| | Mean | 298184.2 | 456199.5 | 1351372.5 | 1860574.3 | 1351372.5 | 1860574.3 |
| | SD | 336969.41 | 151586.31 | 379053.12 | 760386.93 | 379053.12 | 760386.93 |
| $AUC_{0-24}$/Dose (h/kL) | N | 6 | 6 | 6 | 6 | 6 | 6 |
| | Mean | 149.09 | 114.05 | 675.69 | 465.14 | 675.69 | 465.14 |
| | SD | 168.485 | 37.897 | 189.527 | 190.097 | 189.527 | 190.097 |
| $\lambda_z$ (1/h) | N | 3 | 0 | 4 | 3 | 6 | 6 |
| | Mean | 0.221 | | 0.0199 | 0.0471 | 0.0169 | 0.0194 |
| | SD | 0.02180 | | 0.00966 | 0.05409 | 0.01064 | 0.00927 |
| $t_{1/2}$ (h) | N | 3 | 0 | 4 | 3 | 6 | 6 |
| | Median | 44.04 | | 34.40 | 36.57 | 62.64 | 39.21 |
| | Min, Max | 14.9, 162.5 | | 22.2, 89.2 | 6.3, 53.8 | 20.0, 74.9 | 19.7, 70.9 |

TABLE 23-continued

Plasma Baseline-corrected Pharmacokinetic Parameters for Total DGLA (Multiple-dose, Pharmacokinetic Population)

| | | Dose Level of DS107G | | | | | |
|---|---|---|---|---|---|---|---|
| | | Day 1 0 to 24 hours | | Day 28 0 to 24 hours | | Day 28 0 to 168 hours | |
| Parameter (unit) | Statistic | 2000 mg (n = 6) | 4000 mg (n = 6) | 2000 mg (n = 6) | 4000 mg (n = 6) | 2000 mg (n = 6) | 4000 mg (n = 6) |
| $AUC_{0-inf}$ | N | 3 | 0 | 4 | 3 | 6 | 6 |
| (ng · h/mL) | Mean | 4161212.0 | | 5159152.1 | 4779645.9 | 5027822.8 | 6303903.1 |
| | SD | 6203131.92 | | 4269186.29 | 2974257.92 | 2286762.41 | 4913744.09 |
| $AUC_{0-inf}$/Dose | N | 3 | 0 | 4 | 3 | 6 | 6 |
| (h/kL) | Mean | 2080.61 | | 2579.58 | 1194.91 | 2513.91 | 1575.98 |
| | SD | 3101.566 | | 2134.593 | 743.564 | 1143.381 | 1228.436 |
| CL/F | N | 3 | 0 | 4 | 3 | 6 | 6 |
| (kL/h) | Mean | 0.0027 | | 0.0006 | 0.0012 | 0.0005 | 0.0009 |
| | SD | 0.00266 | | 0.00041 | 0.00099 | 0.00027 | 0.00056 |
| Vz/F | N | 3 | 0 | 4 | 3 | 6 | 6 |
| (kL) | Mean | 0.106 | | 0.029 | 0.035 | 0.032 | 0.046 |
| | SD | 0.0597 | | 0.0095 | 0.0114 | 0.0133 | 0.0133 |

Max = maximum;
mean = arithmetic mean;
min = minimum;
N = number of subjects providing data;
SD = standard deviation
Note:
Predose DGLA concentration was subtracted from subsequent concentrations before parameter calculation; negative values were replaced by zero.

The steady state plasma baseline corrected pharmacokinetics for free DGLA is reported in Table 24. Briefly, at steady-state, evaluated on Day 28 (0-24 hours), Peak Trough Fluctuation (PTF) was quite high for both dose cohorts (mean, 62.5% and 44.9%). The mean AR was greater for the 2000 mg than the 4000 mg dose cohort for both $C_{max}$ and AUC. The data suggest saturable kinetics and/or presence of change in the distribution volume with repeated dosing of total DGLA.

TABLE 24

Steady-state Plasma Baseline-corrected Pharmacokinetic Parameters for Total DGLA (Multiple-dose, Pharmacokinetic Population)

| | | Day 28: 0 to 24 hours Dose Level of DS107G | |
|---|---|---|---|
| Parameter (unit) | Statistic | 2000 mg (n = 6) | 4000 mg (n = 6) |
| $t_{min}$ | N | 6 | 6 |
| (h) | Median | 1.50 | 2.00 |
| | Min, Max | 0.0, 6.0 | 2.0, 24.0 |
| $C_{min}$ | N | 6 | 6 |
| (ng/mL) | Mean | 37933.3 | 59216.7 |
| | SD | 10890.12 | 37002.29 |
| $CL_{ss}/F$ | N | 6 | 6 |
| (kL/h) | Mean | 0.0016 | 0.0025 |
| | SD | 0.00051 | 0.00107 |
| $Vz_{ss}/F$ | N | 4 | 3 |
| (kL) | Mean | 0.0980 | 0.1047 |
| | SD | 0.04161 | 0.07339 |
| $C_{avg}$ | N | 6 | 6 |
| (ng/mL) | Mean | 56307.2 | 77523.9 |
| | SD | 15793.88 | 31682.79 |
| % PTF | N | 6 | 6 |
| (%) | Mean | 62.50 | 44.90 |
| | SD | 31.403 | 38.967 |
| $AR(C_{max})$ | N | 6 | 6 |
| | Mean | 5.156 | 3.440 |
| | SD | 2.2542 | 1.2090 |

TABLE 24-continued

Steady-state Plasma Baseline-corrected Pharmacokinetic Parameters for Total DGLA (Multiple-dose, Pharmacokinetic Population)

| | | Day 28: 0 to 24 hours Dose Level of DS107G | |
|---|---|---|---|
| Parameter (unit) | Statistic | 2000 mg (n = 6) | 4000 mg (n = 6) |
| AR(AUC) | N | 6 | 6 |
| | Mean | 7.991 | 4.163 |
| | SD | 5.9537 | 1.2331 |

Figure 14:
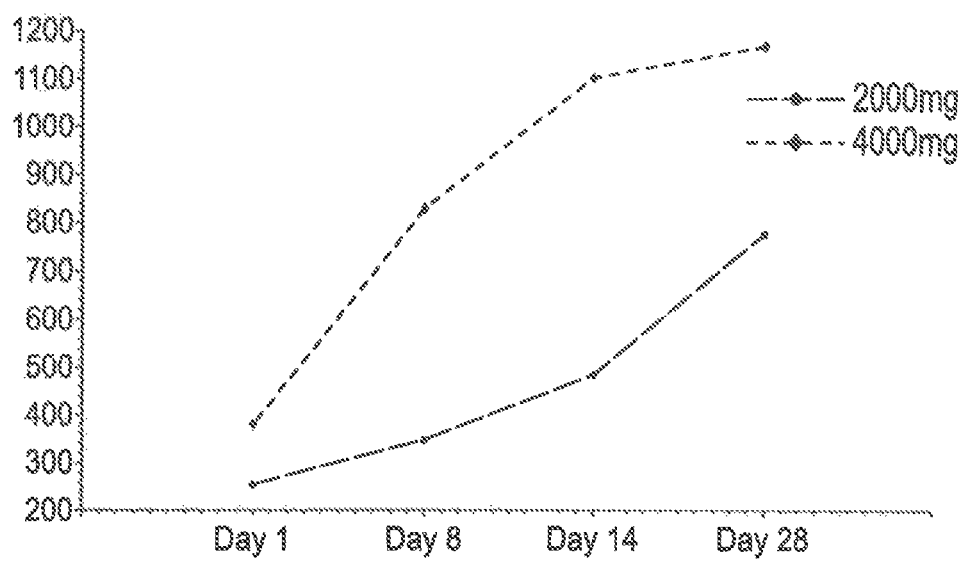
FIG. 14 shows mean skin blister fluid concentration of Free DGLA (ng/mL, linear plot), by dose cohort (Multiple-dose, PK Population).
Figure 15:
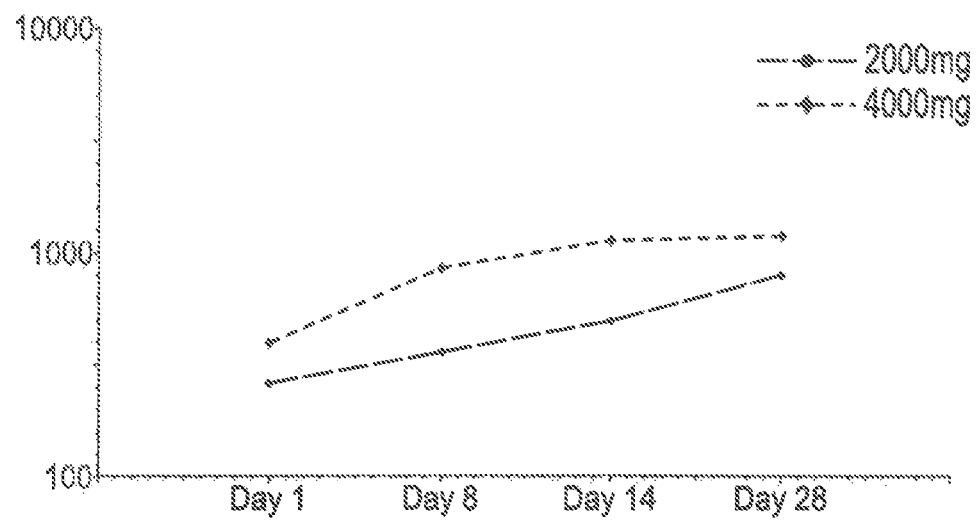
FIG. 15 shows mean skin blister fluid concentration of free DGLA (ng/mL, log-linear plot), by dose cohort (Multiple-dose, PK Population).

Mean free DGLA concentrations in skin blister fluid are shown by dose cohort in FIG. 14 (linear plot) and FIG. 15 (log-linear plot). Mean concentrations approximately doubled with a doubling in dose (based on concentrations from Days 1, 8, 14, and 28), and accumulated with repeated doses in both regimens. Mean free DGLA concentrations on Day 28 were about 3-fold higher than those on Day 1 for both 2000 and 4000 mg daily.

Figure 16:
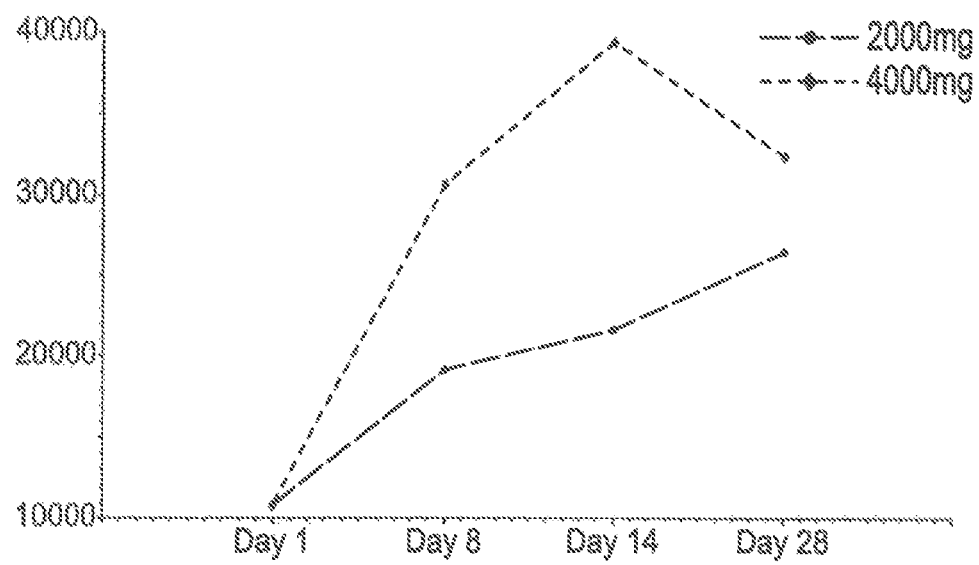
FIG. 16 shows mean skin blister fluid concentration of total DGLA (ng/mL, linear plot), by dose cohort (Multiple-dose, PK Population).
Figure 17:
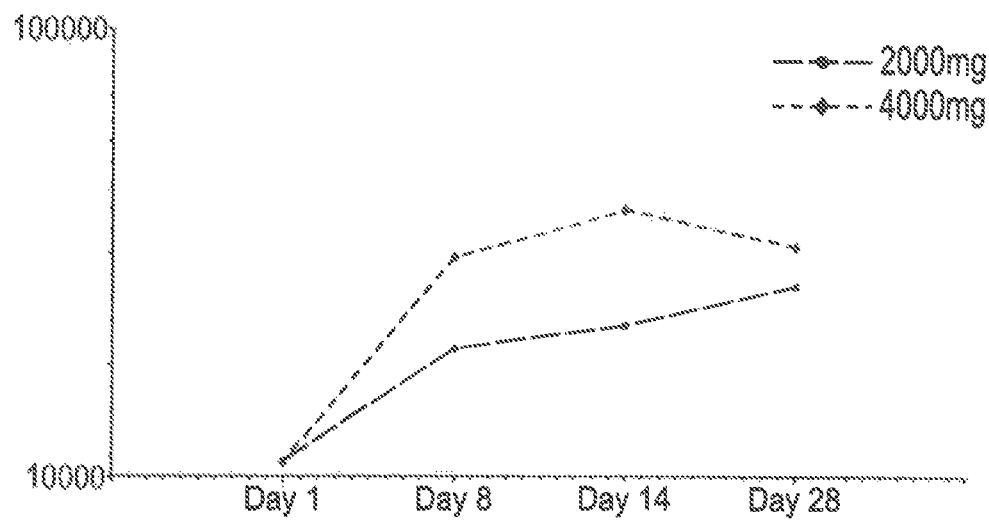
FIG. 17 shows mean skin blister fluid concentration of total DGLA (ng/mL, log-linear plot), by dose cohort (Multiple-dose, PK Population)

Mean total DGLA concentrations in skin blister fluid are shown by dose cohort in FIG. 16 (linear plot) and FIG. 17 (log-linear plot). Mean concentrations of total DGLA increased about 1.4-fold with a doubling in dose (based on concentrations from Days 1, 8, 14, and 28). Mean total DGLA concentrations on Day 28 were about 2.5- and 3-fold higher than those on Day 1 for 2000 and 4000 mg daily, respectively.

Figure 18:
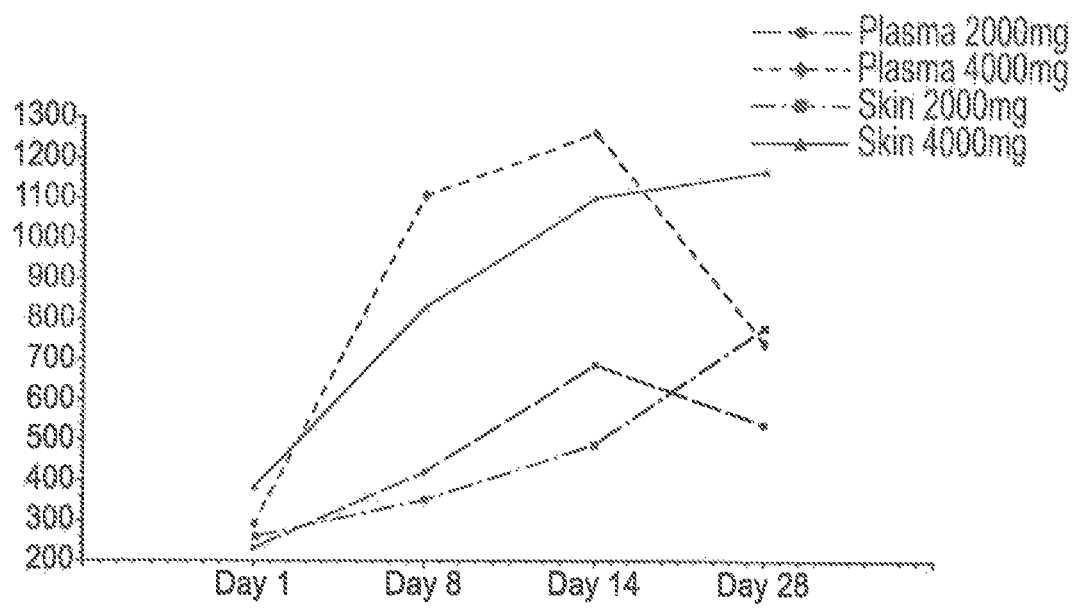
FIG. 18 shows mean free DGLA concentration (ng/mL, linear plot) in plasma and skin blister fluid, by dose cohort (Multiple-dose, PK Population).
Figure 19:
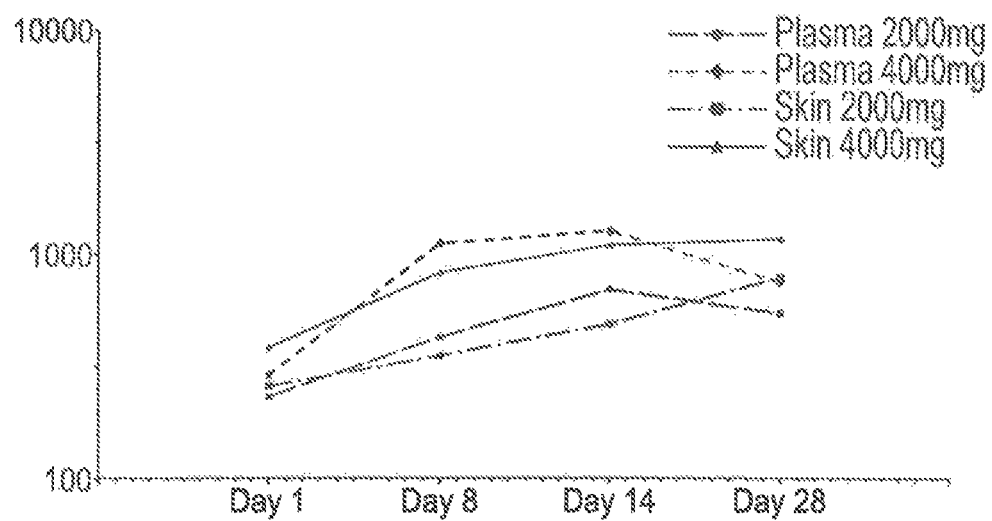
FIG. 19 shows mean free DGLA concentration (ng/mL, log-linear plot) in plasma and skin blister fluid, by dose cohort (Multiple-dose, PK Population).

The concentration profiles in plasma and skin blister fluid were overlaid and mean concentrations of free DGLA were somewhat similar in plasma and skin blister fluid for the same DS107G dose at Day 8 and Day 14 (but not Day 28). FIG. 18 [linear plot] and FIG. 19 [log-linear plot]), suggest that free DGLA distributes into plasma and skin similarly.

Figure 20:
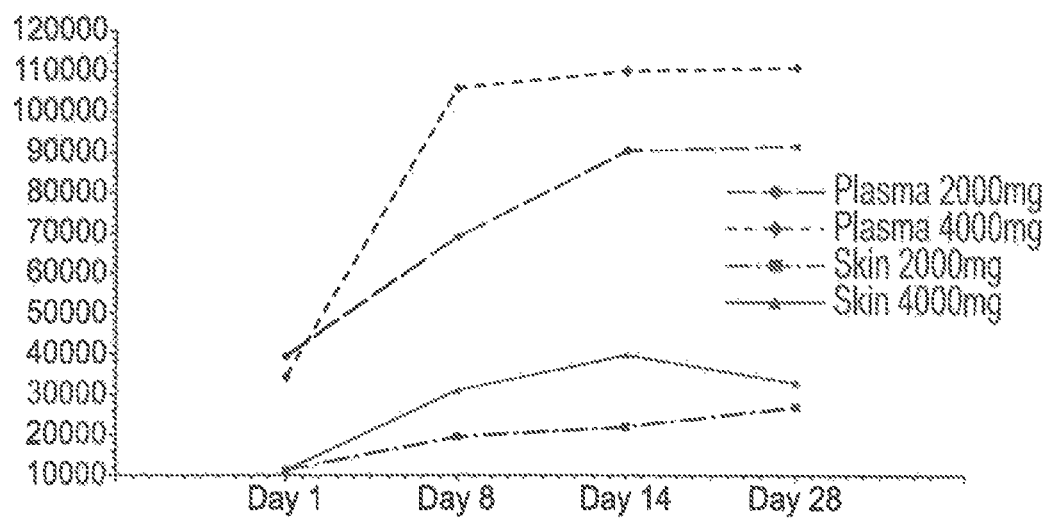
FIG. 20 shows mean total DGLA concentration (ng/mL, linear plot) in plasma and skin blister fluid, by dose cohort (Multiple-dose, PK Population).
Figure 21:
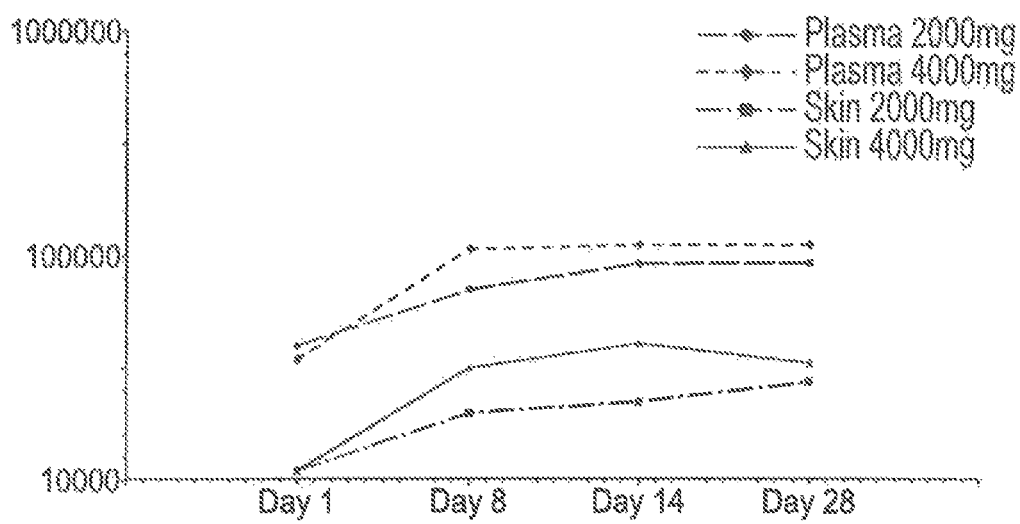
FIG. 21 shows mean total DGLA concentration (ng/mL, log-linear plot) in plasma and skin blister fluid, by dose cohort (Multiple-dose, PK Population).

For total DGLA, mean concentrations were much higher in plasma than in skin blister fluid for the same DS107G dose after Day 1 (FIG. 20 [linear plot] and FIG. 21 [log-linear plot]), indicating that total DGLA is found more readily in plasma than into skin. The mechanism for limited distribution of total DGLA into skin is most likely related to the lower quantity of lipids in the skin compared with plasma.

Figure 22:
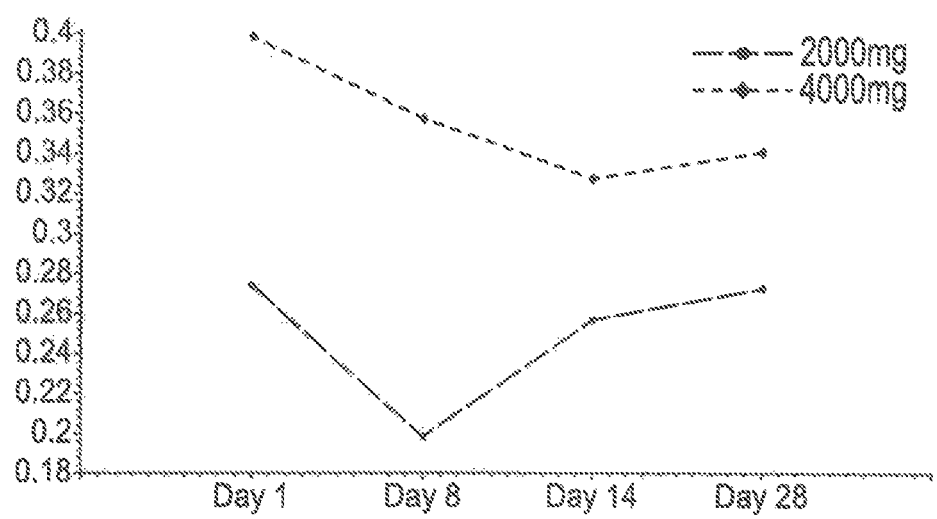
FIG. 22 shows mean plasma dihydrotestosterone concentration (ng/mL, linear plot), by dose cohort (Multiple-dose, PK Population).
Figure 23:
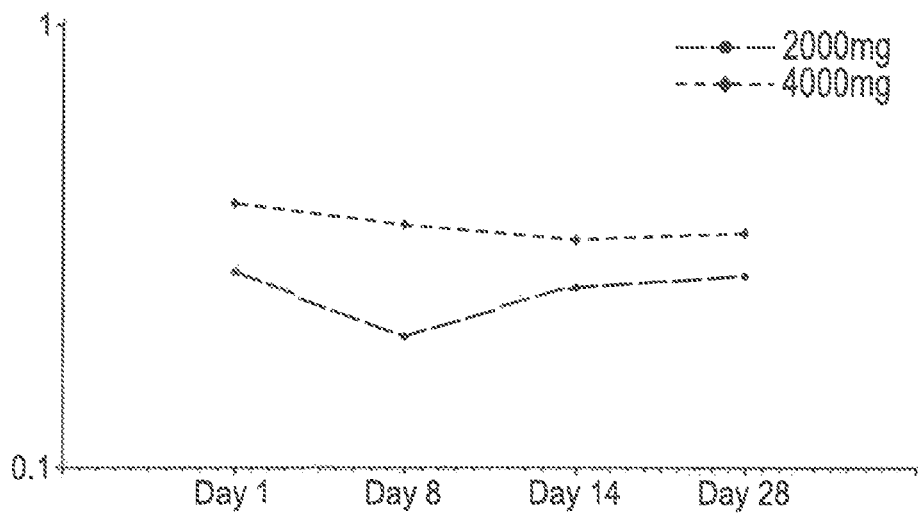
FIG. 23 shows mean plasma dihydrotestosterone concentration (ng/mL, log-linear plot), by dose cohort (Multiple-dose, PK Population).

Plasma dihydrotestosterone (DHT) concentrations were quantified as an exploratory efficacy endpoint or biomarker. Inter-subject variability in the concentration data was high based on the SD at most time points. Mean plasma concentrations of DHT are shown by dose cohort in FIG. 22 (linear) and FIG. 23 (log-linear).

None of the samples had measurable free 15-HETrE concentrations; all concentrations were below the LLOQ (100 ng/m L).

There were no deaths for the multi-dose study. When administered to healthy volunteers as 2000- or 4000-mg doses once daily for 28 consecutive days, DS107G was tolerated well, with the worst TEAE being mild to moderate diarrhea (reported term: loose stool) of relatively short duration. A majority of the events of diarrhea (incidence 7/12 [43.8%] active-treated subjects vs 0/4 [0.0%] placebo-control subjects) were considered by the Investigator to be possibly related to study drug. A higher proportion of subjects reported diarrhea in the 4000-mg group (4/6 [66.7%]) than in the 2000-mg group (3/6 [50%]). The incidence of TEAEs among active-treated subjects was much higher than that of the placebo-control subjects (11/12 [91.73%] subjects reporting a total of 52 TEAEs vs 1/4 [25.0%] subjects reporting a total of I TEAE, respectively). There were no severe TEAEs, and other than TEAEs of diarrhea, all events were considered to be either not or unlikely related to study drug. Nausea was the next most commonly reported TEAE (10 events among 4/6 [66.7%] subjects in the 4000-mg treatment group); 9/10 of the events of nausea were mild and the other was moderate in severity. Other than diarrhea, all remaining TEAEs were reported in 2 subjects each (bronchitis and nasopharyngitis) or 1 subject each (abdominal pain, asthenia, pyrexia, blood CPK increased, CRP increased, WBC count decreased, dizziness, headache, cough, and haematoma), the majority of which were considered by the Investigator to be unlikely or not related to study drug. Other TEAEs considered to be possibly related to study drug were abdominal pain and asthenia (Reported Term "weakness"), both of which had temporal associations with events of loose stool.

No clinically significant abnormalities in the vital sign or ECG observed in any patients in multiple dose study.

We claim:

1. A pharmaceutical composition comprising at least about 80% dihomo gamma linolenic acid (DGLA), by weight of total fatty acids, encapsulated in a capsule shell.

2. The pharmaceutical composition of claim 1, wherein the DGLA is at least about 90%, by weight of total fatty acids, encapsulated in a capsule shell.

3. The pharmaceutical composition of claim 1, wherein the DGLA is at least about 95%, by weight of total fatty acids, encapsulated in a capsule shell.

4. The pharmaceutical composition of claim 1 further comprising eicosatetraenoic acid.

5. The pharmaceutical composition of claim 1 further comprising oleic acid.

6. The pharmaceutical composition of claim 1, wherein up to about 1 g of the composition is encapsulated in the capsule shell.

7. The pharmaceutical composition of claim 4, wherein up to about 1 g of the composition is encapsulated in the capsule shell.

8. The pharmaceutical composition of claim 5, wherein up to about 1 g of the composition is encapsulated in the capsule shell.

9. The pharmaceutical composition of claim 1, comprising up to about 1 g of DGLA and wherein the composition comprises not more than 5%, by weight of total fatty acids, of any individual fatty acid other than DGLA.

10. The pharmaceutical composition of claim 1, wherein upon oral administration of multiple daily doses of the composition comprising about 500 mg of DGLA encapsulated in a gelatin shell to a fasted subject the subject exhibits one or more of the following outcomes:
    (a) a free DGLA Cmax of about 700 ng/ml to about 3200 ng/ml;
    (b) a free DGLA AUC0-24 of about 2500 ng·h/ml to about 10000 ng·h/ml;
    (c) a free DGLA AUC0-24/dose of about 2 to about 6 h/kL;
    (d) a free DGLA tmax (h) of about 3 to about 8 hours;
    (e) a total DGLA Cmax of about 7000 ng/ml to about 32000 ng/ml;
    (f) a total DGLA AUC0-24 of about 25,000 ng·h/ml to about 225,000 ng·h/ml;
    (g) a total DGLA AUC0-24/dose 70 to about 225 h/kL;
    (h) a total DGLA tmax (h) of about 3 to about 20 hours;
    (i) a total DGLA Cmax/dose of about 2 (1/kL) to about 25 (1/kl), about 4 (1/kl) to about 20 (1/kl) or about 5 (1/kl) to about 17 (1/kl);
    (j) a free DGLA Cmax/dose of about 0.3 (1/kL) to about 2.5 (1/kL)
    (k) a ratio of total DGLA Cmax to free DGLA Cmax of about 7:1 to about 9:1; and/or
    (1) a ratio of free DGLA plasma to DGLA skin as measured in skin blister fluid from about 0.6:1 to about 1.5:1.

11. The pharmaceutical composition of claim 1, wherein upon oral administration of multiple daily doses of the composition to a fasted subject for a period of about 2 to about 30 days, each daily dose comprising about 500 mg of DGLA encapsulated in a gelatin shell, the subject exhibits one or more of the following outcomes:
    (a) a steady state free DGLA plasma level ($C_{avg}$) of up to about 2000 ng/ml, up to about 750 ng/ml, or up to about 350 ng/ml;
    (b) a steady state total DGLA plasma level ($C_{avg}$) of up to 250,000 ng/ml, up to 180,000 ng/ml, up to 150,000 ng/ml, up to 125,000 ng/ml or up to 100,000 ng/ml; and/or
    (c) a ratio of free DGLA plasma to DGLA as measured in skin blister fluid from about 0.2:1 to about 5:1, about 0.5:1 to about 2.5:1 or about 0.6:1 to about 1.5:1.

12. The pharmaceutical composition of claim 1, wherein upon oral administration of multiple daily doses of the composition to a fasted subject and to a fed subject for a period of about 2 to about 30 days, each daily dose comprising about 500 mg of DGLA encapsulated in a gelatin shell, the subjects exhibit:
    (a) a ratio of free DGLA Cmax fasted:fed of between 1:1 to 5:1; of about 2.5:1, of about 3:1 or of about 3.5:1;
    (b) a ratio of free DGLA AUC0-24 fasted:fed of between 1:1 to 5:1; of about 1.5:1, of about 2:1 or of about 2.5:1;
    (c) a ratio of total DGLA Cmax fasted:fed of between 1:1 to 5:1; of about 1:1, of about 1.5:1 or of about 2:1; and/or (d) a ratio of total DGLA AUC0-24 fasted:fed of between 1:1 to 5:1; of about 1.5:1, of about 2:1 or of about 2.5:1.

* * * * *